United States Patent
Weiner et al.

(10) Patent No.: US 12,419,945 B2
(45) Date of Patent: *Sep. 23, 2025

(54) VACCINES AGAINST ZIKA VIRUS

(71) Applicants: The Trustees of the University of Pennsylvania, Philadelphia, PA (US); The Wistar Institute of Anatomy and Biology, Philadelphia, PA (US)

(72) Inventors: David Weiner, Merion, PA (US); Kar Muthumani, Cherry Hill, NJ (US)

(73) Assignees: The Wistar Institute of Anatomy and Biology, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/318,061

(22) Filed: May 16, 2023

(65) Prior Publication Data

US 2024/0115689 A1    Apr. 11, 2024

Related U.S. Application Data

(63) Continuation of application No. 16/078,270, filed as application No. PCT/US2017/019407 on Feb. 24, 2017, now Pat. No. 11,648,303.

(60) Provisional application No. 62/462,249, filed on Feb. 22, 2017, provisional application No. 62/417,100, filed on Nov. 3, 2016, provisional application No. 62/396,742, filed on Sep. 19, 2016, provisional application No. 62/305,183, filed on Mar. 8, 2016, provisional application No. 62/300,030, filed on Feb. 25, 2016.

(51) Int. Cl.
| | | |
|---|---|---|
| A61K 39/12 | (2006.01) | |
| A61K 39/00 | (2006.01) | |
| C07K 14/18 | (2006.01) | |
| C07K 14/54 | (2006.01) | |
| C12N 7/00 | (2006.01) | |

(52) U.S. Cl.
CPC .......... *A61K 39/12* (2013.01); *C07K 14/1816* (2013.01); *C12N 7/00* (2013.01); *A61K 2039/53* (2013.01); *C07K 14/54* (2013.01); *C07K 2319/02* (2013.01); *C12N 2770/24034* (2013.01)

(58) Field of Classification Search
CPC ................ A61K 39/12; A61K 2039/53; C07K 14/1816; C07K 14/54; C07K 2319/02; C07K 14/005; C12N 7/00; C12N 2770/24034; C12N 2770/24122; C12N 2770/24134; C12N 2770/24171; A61P 31/14; A61P 37/04; A61P 43/00; Y02A 50/30
See application file for complete search history.

(56) References Cited

U.S. PATENT DOCUMENTS

| | | |
|---|---|---|
| 8,691,961 B1 | 4/2014 | Puffer |
| 2007/0292453 A1 | 12/2007 | Floyd |
| 2011/0236421 A1 | 9/2011 | Brown |
| 2014/0274762 A1 | 9/2014 | Manuguerra |
| 2017/0014502 A1 | 1/2017 | Sumathy |
| 2017/0340724 A1 | 11/2017 | Ciaramella |
| 2019/0358314 A1 | 11/2019 | Weissman |
| 2021/0205434 A1 | 7/2021 | Petsch |

FOREIGN PATENT DOCUMENTS

| | | |
|---|---|---|
| BR | 112018000862 | 9/2018 |
| CN | 101909635 | 12/2010 |
| CN | 102292345 | 12/2011 |
| CN | 103476928 | 12/2013 |
| WO | 2009099716 | 8/2009 |
| WO | 2010057159 A2 | 5/2010 |
| WO | 2011054011 A2 | 5/2011 |
| WO | 2011115583 A1 | 9/2011 |
| WO | 2012106377 | 8/2012 |
| WO | 2012106377 A2 | 8/2012 |
| WO | 2014144786 | 9/2014 |
| WO | 2017015463 A2 | 1/2017 |
| WO | 2017147458 | 8/2017 |
| WO | 2018014113 | 1/2018 |
| WO | 2018053478 | 3/2018 |

OTHER PUBLICATIONS

Dyer O. "Zika vaccine could be in production by year's end, says maker." BMJ 2016;352:i630. Published Feb. 1, 2016. (Year: 2016).*
Inovio Pharm. "Inovio Pharmaceutical's DNA Vaccine for Zika Virus Induces Robust Immune Responses in Preclinical Study." Feb. 17, 2016. https://ir.inovio.com/news-releases/default.aspx (Year: 2016).*
Tajima S, et al. Polyprotein [Zika virus]. GenBank: BAP47441.1, Dep. Sep. 12, 2014. (Year: 2014).*
B. D. Cox et al: "Predicting Zika virus structural biology: Challenges and opportunities for intervention", Antiviral Chemistry & Chemotherapy., vol. 24, No. 3-4, Aug. 1, 2015 (Aug. 1, 2015), pp. 118-126, XP055328128, GB, ISSN: 0956-3202, DOI: 10.1177/2040206616653873.
Dar et al., "Prediction of promiscuous T-cell epitopes in the Zika virus polyprotein: An in silico approach", Asian Pac J Trop Med, (Jul. 26, 2016), vol. 9, pp. 844-850, XP029724754.

(Continued)

*Primary Examiner* — Rachel B Gill
(74) *Attorney, Agent, or Firm* — Riverside Law LLP

(57) ABSTRACT

An aspect of the present invention is related to nucleic acid constructs capable of expressing a Zika antigen that elicits an immune response in a mammal against Zika virus, and methods of use thereof. Additionally, there are DNA plasmid vaccines capable of generating in a mammal an immune response against a Zika virus, comprising a DNA plasmid and a pharmaceutically acceptable excipient, and methods of use thereof. The DNA plasmid is capable of expressing a Zika antigen in a cell of the mammal in a quantity effective to elicit an immune response in the mammal that is cross reactive against all Zika strains.

17 Claims, 39 Drawing Sheets
Specification includes a Sequence Listing.

(56) References Cited

OTHER PUBLICATIONS

Dikhit et al., "Computational prediction and analysis of potential antigenic CTL epitopes in Zika virus: A first step towards vaccine development", Infect Genet Evol, (Aug. 31, 2016), vol. 45, pp. 187-197, XP029816628.

Extended European Search Report for Application No. EP17757325.0, dated Oct. 7, 2019, 12 pages.

Faye O, Faye O, Diallo D, Diallo M. Weidmann M, Sail AA. Quantitative real-time PCR detection of Zika virus and evaluation with field-caught mosquitoes. Virol J. Oct. 22, 2013; 10:311. (Year: 2013).

Genbank ABI54475—polyprotein [Zika virus].

Genbank KU686218—Zika virus isolate MEX/InDRE/14/2015 polyprotein gene, partial cds.

Kuno et al: "Full-length sequencing and genomic characterization of Bagaza, Kedougou, and Zika viruses", Archives of Virology ; Official Journal of the Virology Divisionof the International Union of Microbiological Societies, Springer-Verlag, VI, vol. 152, No. 4, Jan. 3, 2007 (Jan. 3, 2007), pp. 687-696, XP019493186, ISSN: 1432-8798, DOI: 10.1007/500705-006-0903-Z.

Office Action (Notice of Allowance and Fees Due (PTOL-85)) dated Mar. 4, 2022 for U.S. Appl. No. 16/078,270 (pp. 1-8).

Office Action (Notice of Allowance and Fees Due (PTOL-85)) dated Jun. 14, 2022 for U.S. Appl. No. 16/078,270 (pp. 1-7).

Office Action dated Aug. 11, 2021 for U.S. Appl. No. 16/078,270 (pp. 1-11).

Shawan et al: "Design and Prediction of Potential RNAi (siRNA) Molecules for 3' UTR PTGS of Different Strains of Zika Virus: A Computational Approach", Nature and Science, vol. 13, No. 2, Jan. 1, 2015 (Jan. 1, 2015), pp. 37-50, XP055326136, US, ISSN: 1545-0740.

Shawan et al: "In silico modeling and immunoimformatics probing disclose the epitope based peptide vaccine against Zika virus envelope glycoprotein", Indian J. Pharm. Biol. Res, vol. 2, No. 4, Dec. 10, 2014 (Dec. 10, 2014), pp. 44-57, XP009513657, ISSN: 2320-9267, Retrieved from the Internet: URL:https://search.proquest.com/openview/882550763906a0d3408935ed9ab781e1/1.pdf?pq-origsite=gscholar&cbl=2035923.

* cited by examiner
MDWTWILFLVAAATRVHSGIIGLLLTTAMAAEITRRGSAYY
MYLDRNDAGEAISFPTTLGMNKCYIQIMDLGHMCDATMSYE
CPMLDEGVEPDDVDCWCNTTSTWVVYGTCHHKKGEARRSRR
AVTLPSHSTRKLQTRSQTWLESREYTKHLIRVENWIFRNPG
FALAAAAIAWLLGSSTSQKVIYLVMILLIAPAYSIRCIGVS
NRDFVEGMSGGTWVDVVLEHGGCVTVMAQDKPTVDIELVTT
TVSNMAEVRSYCYEASISDMASDSRCPTQGEAYLDKQSDTQ
YVCKRTLVDRGWGNGCGLFGKGSLVTCAKFTCSKKMTGKSI
QPENLEYRIMLSVHGSQHSGMIVNDIGHETDENRAKVEVTP
NSPRAEATLGGFGSLGLDCEPRTGLDFSDLYYLTMNNKHWL
VHKEWFHDIPLPWHAGADTGTPHWNNKEALVEFKDAHAKRQ
TVVVLGSQEGAVHTALAGALEAEMDGAKGRLFSGHLKCRLK
MDKLRLKGVSYSLCTAAFTFTKVPAETLHGTVTVEVQYAGT
DGPCKVPAQMAVDMQTLTPVGRLITANPVITESTENSKMML
ELDPPFGDSYIVIGVGDKKITHHWHRSGSTIGKAFEATVRG
AKRMAVLGDTAWDFGSVGGVFNSLGKGIHQIFGAAFKSLFG
GMSWFSQILIGTLLVWLGLNTKNGSISLTCLALGGVMIFLS
TAVSA

SEQ ID No. 1

LS+pre+Membrane+Envelope (DIII domain; Transmembrane I &II)

WB: anti-sera (day 21)  WB: anti-Pan-Flavivirus (4G2)

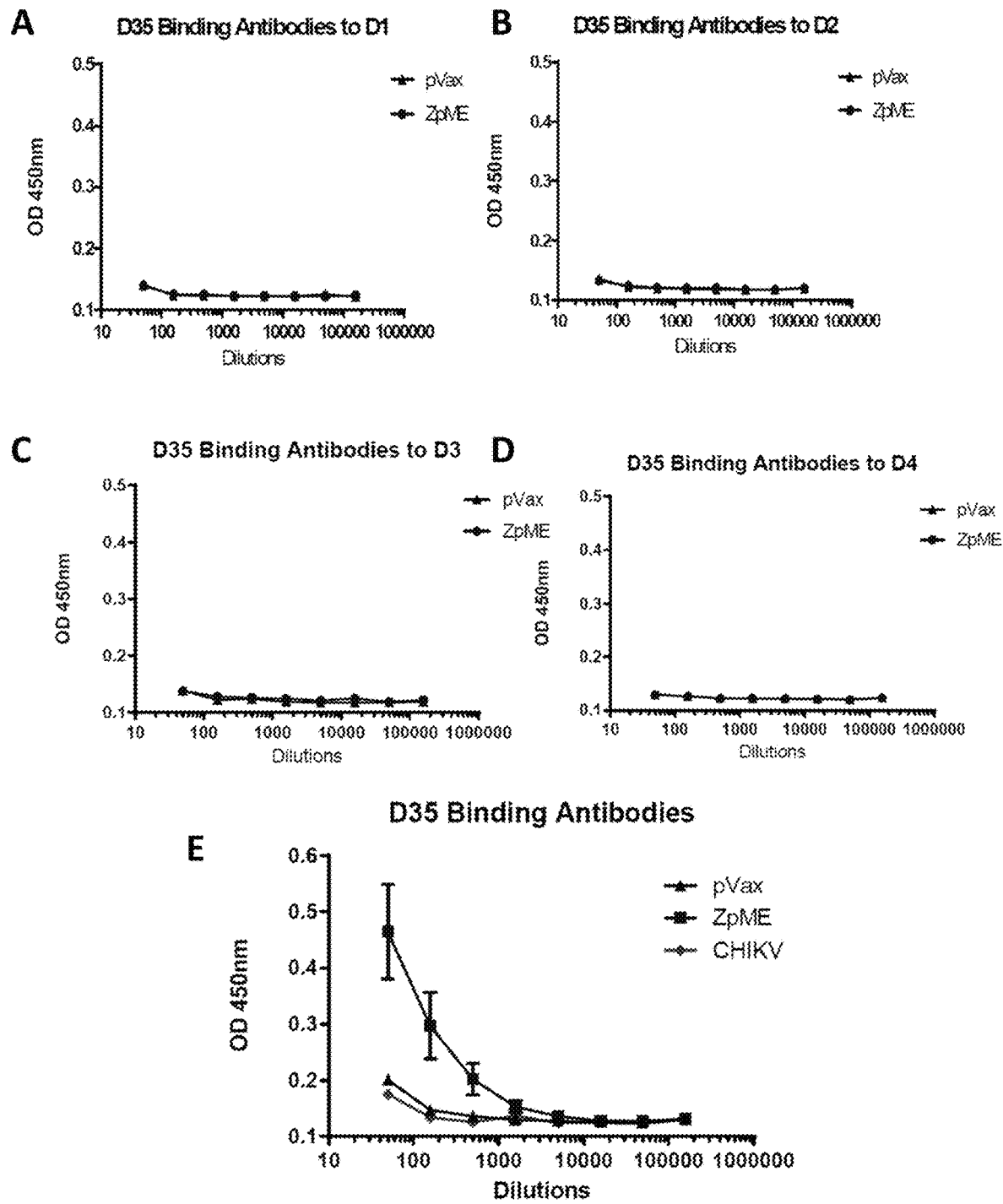
FIG. 15A-E

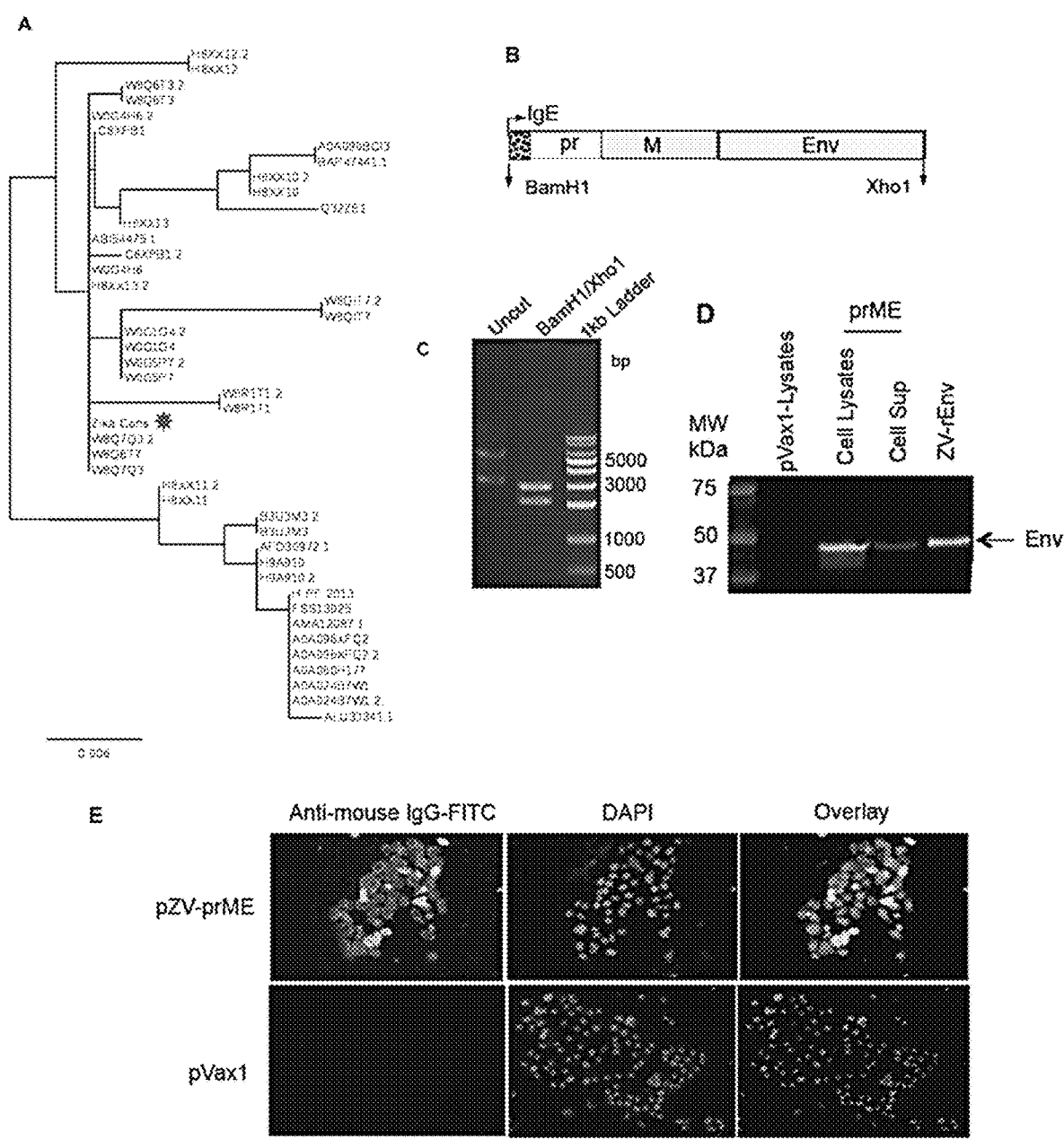
FIG. 16A-E

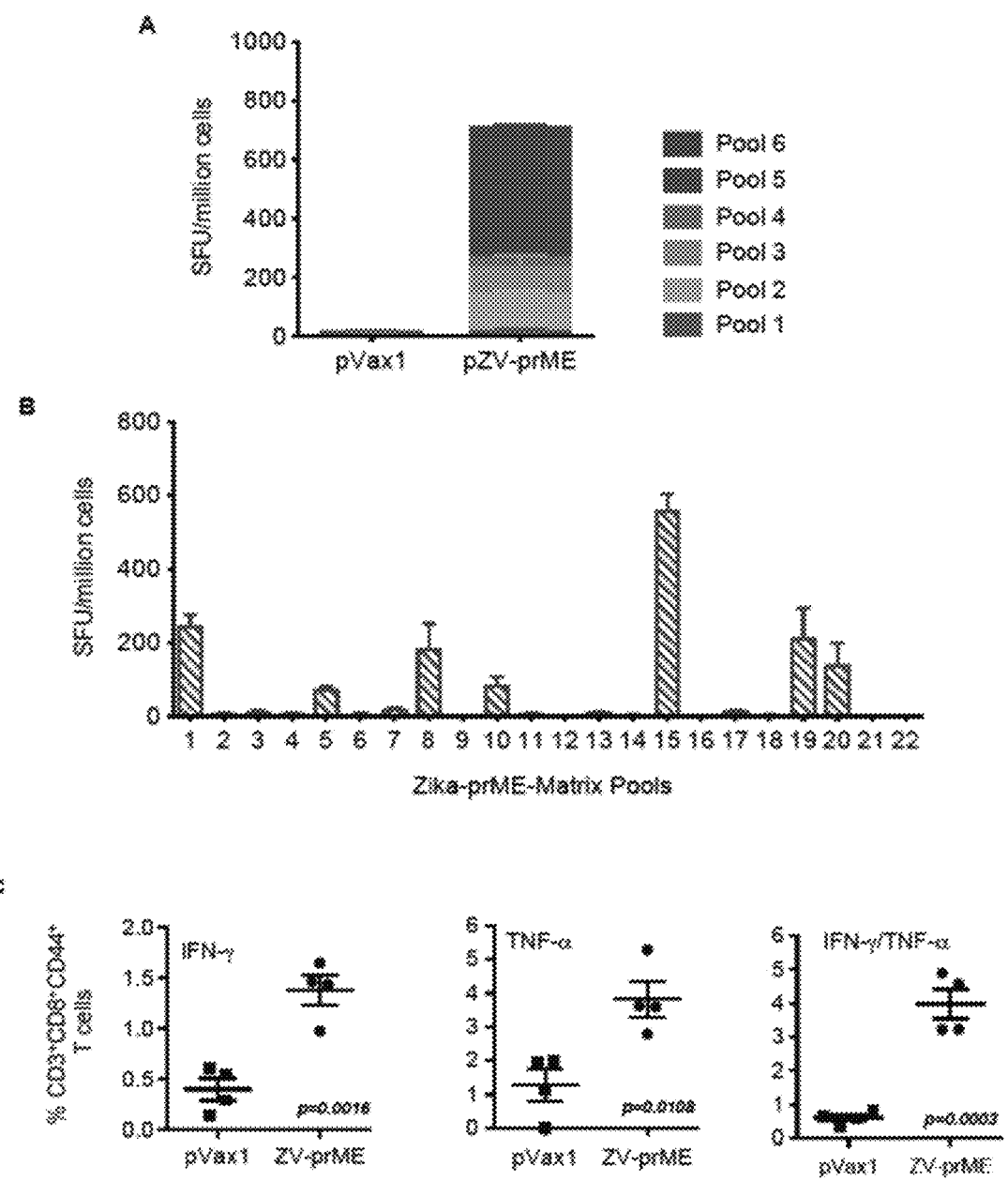
FIG. 17A-C

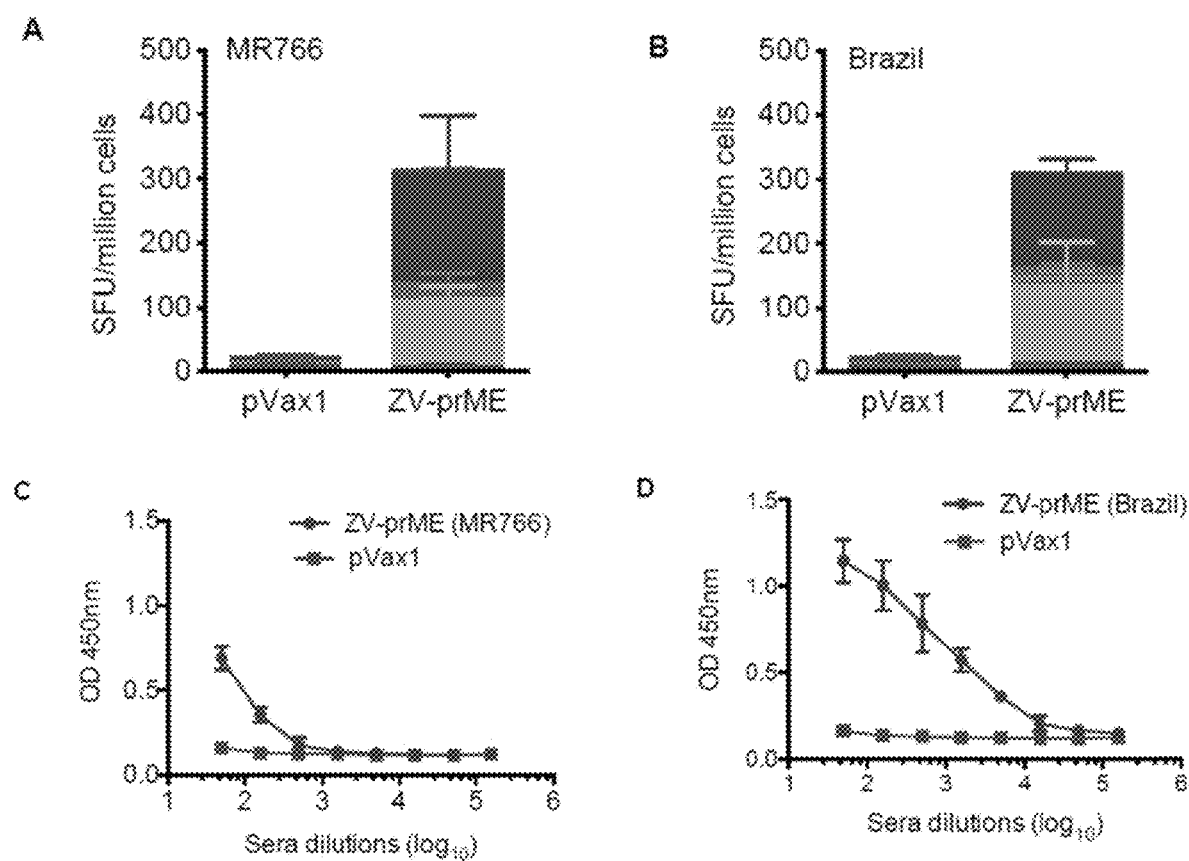
FIG. 13A-D

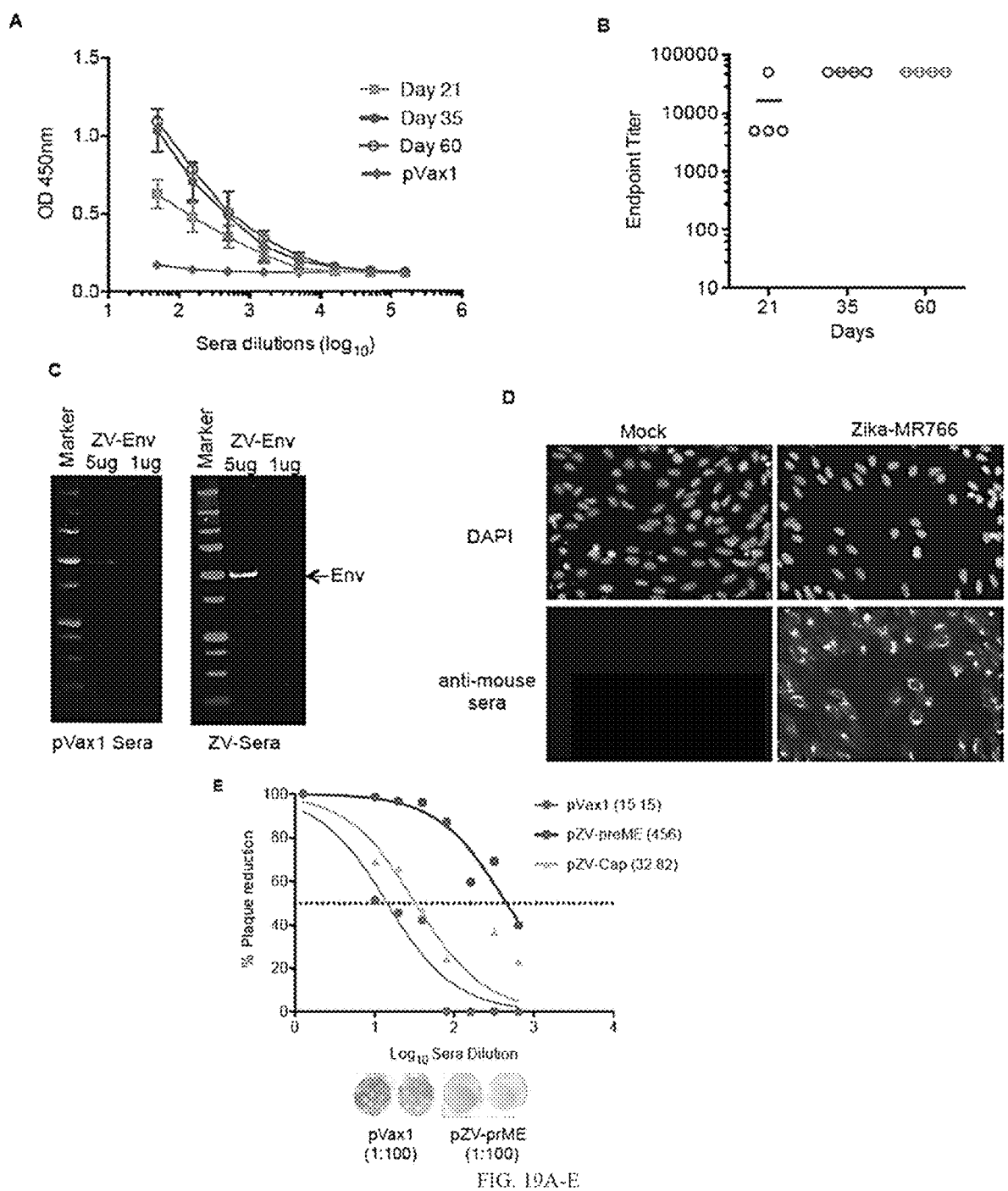
FIG. 19A-E

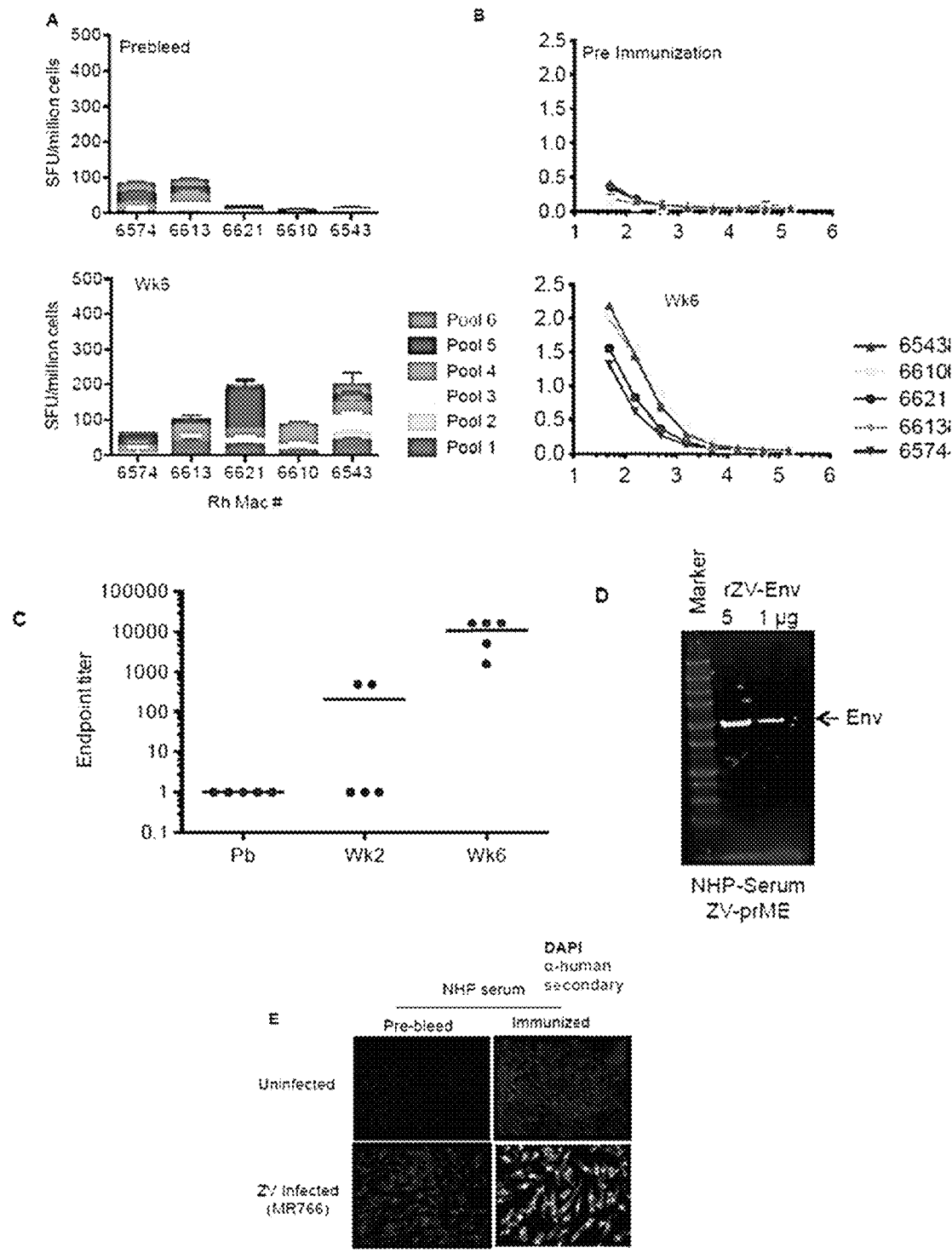
FIG. 20A-E

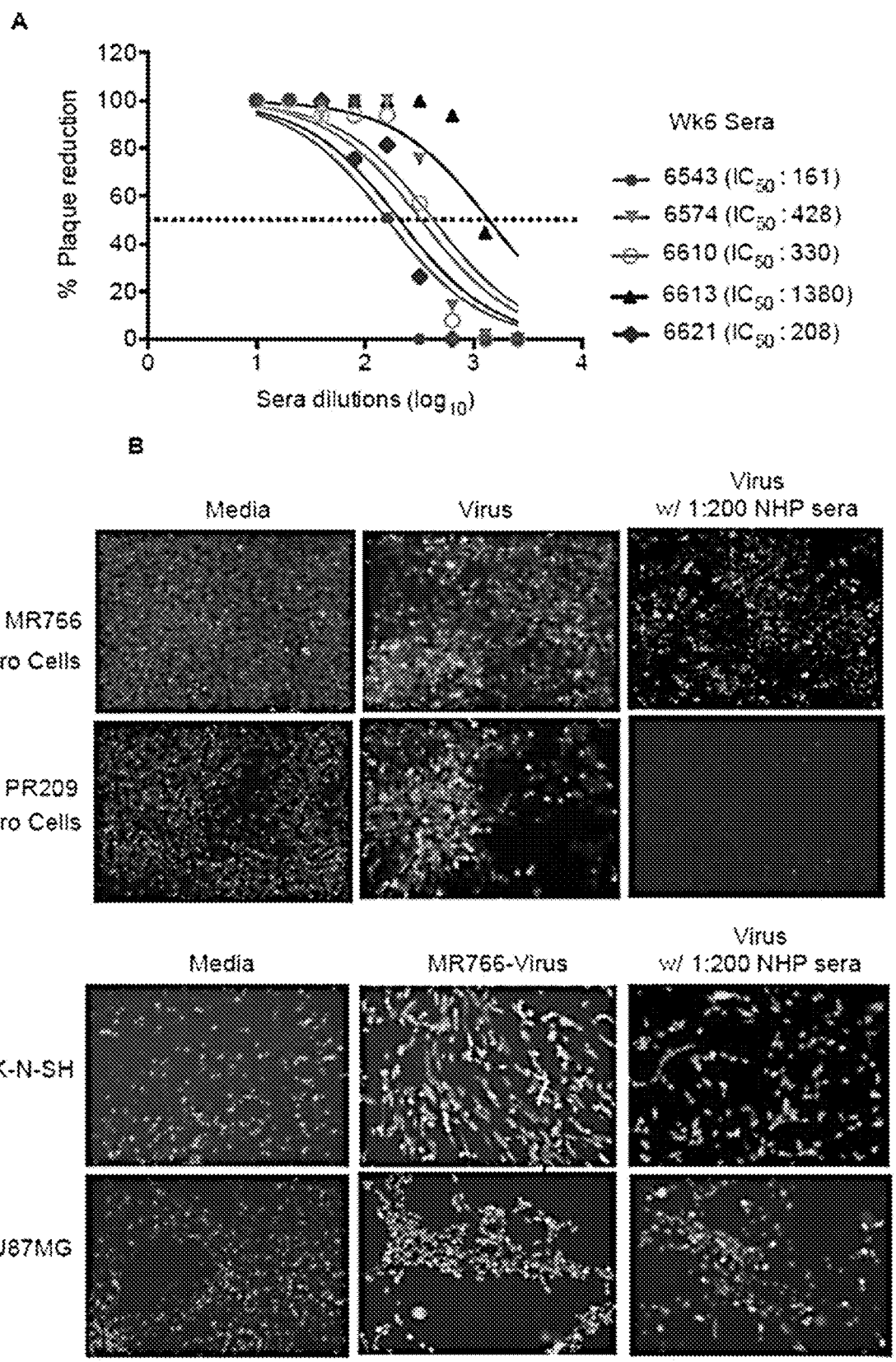
FIG. 21A-C

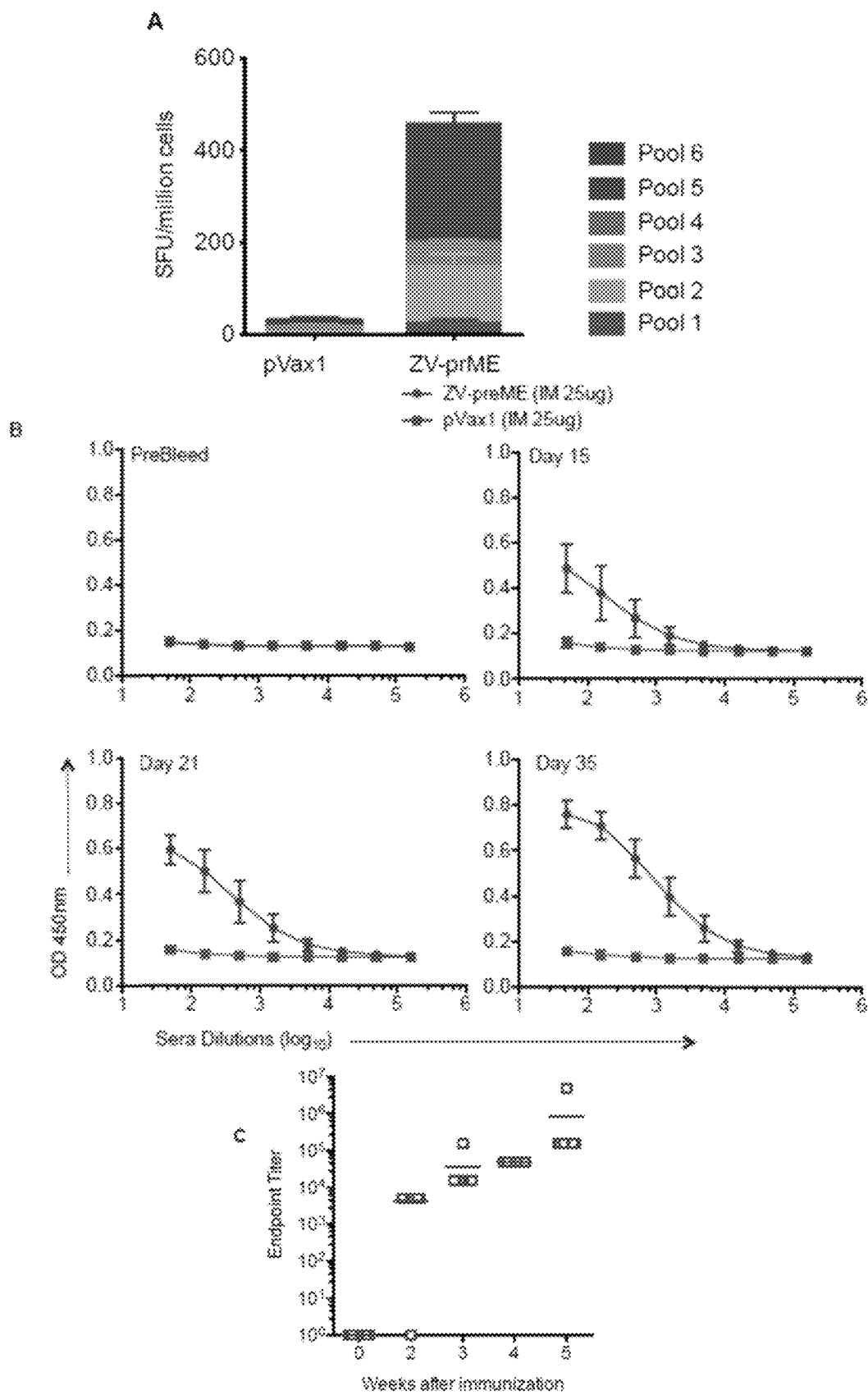
FIG. 22A-C

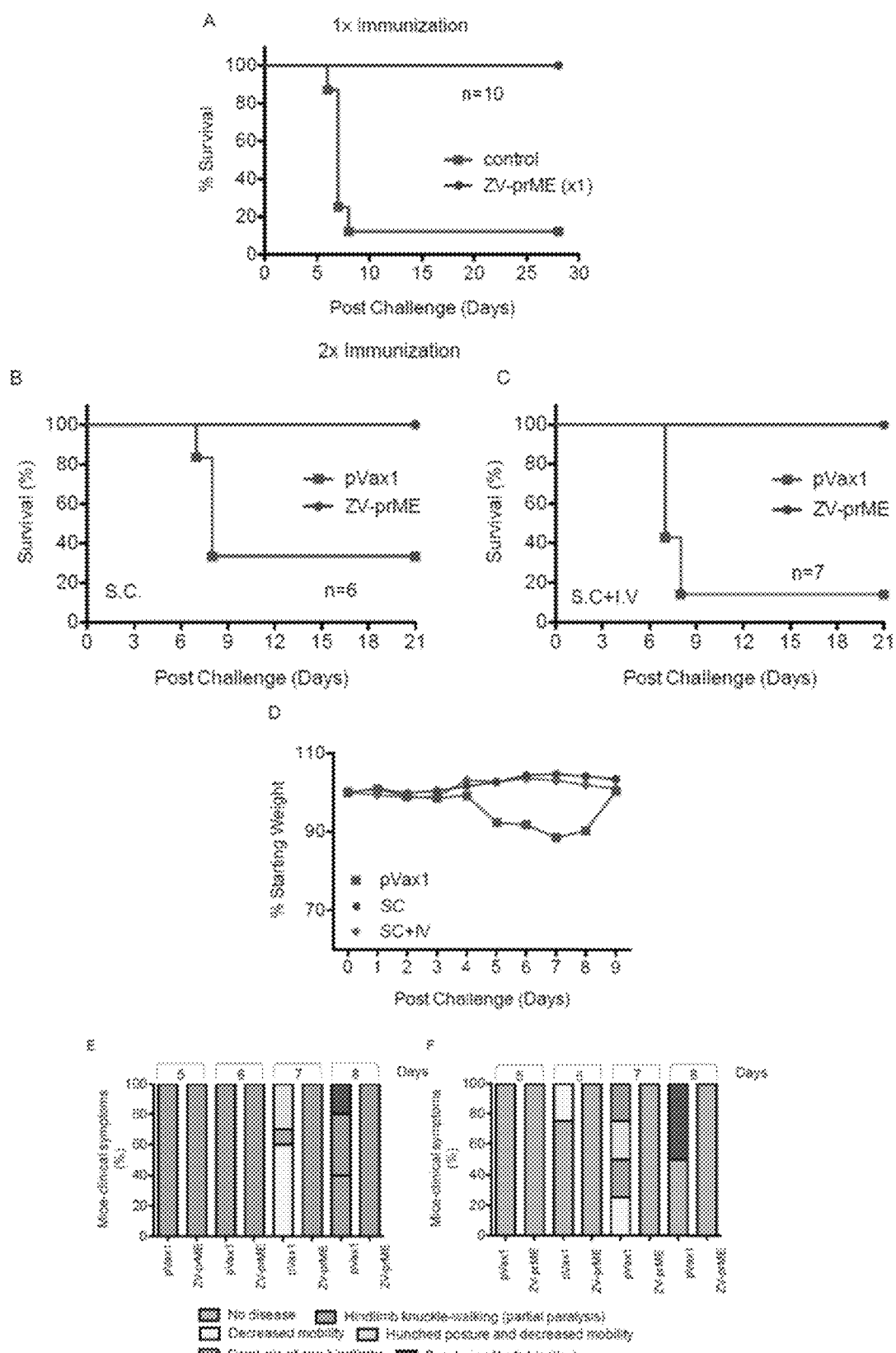
FIG. 23A-F

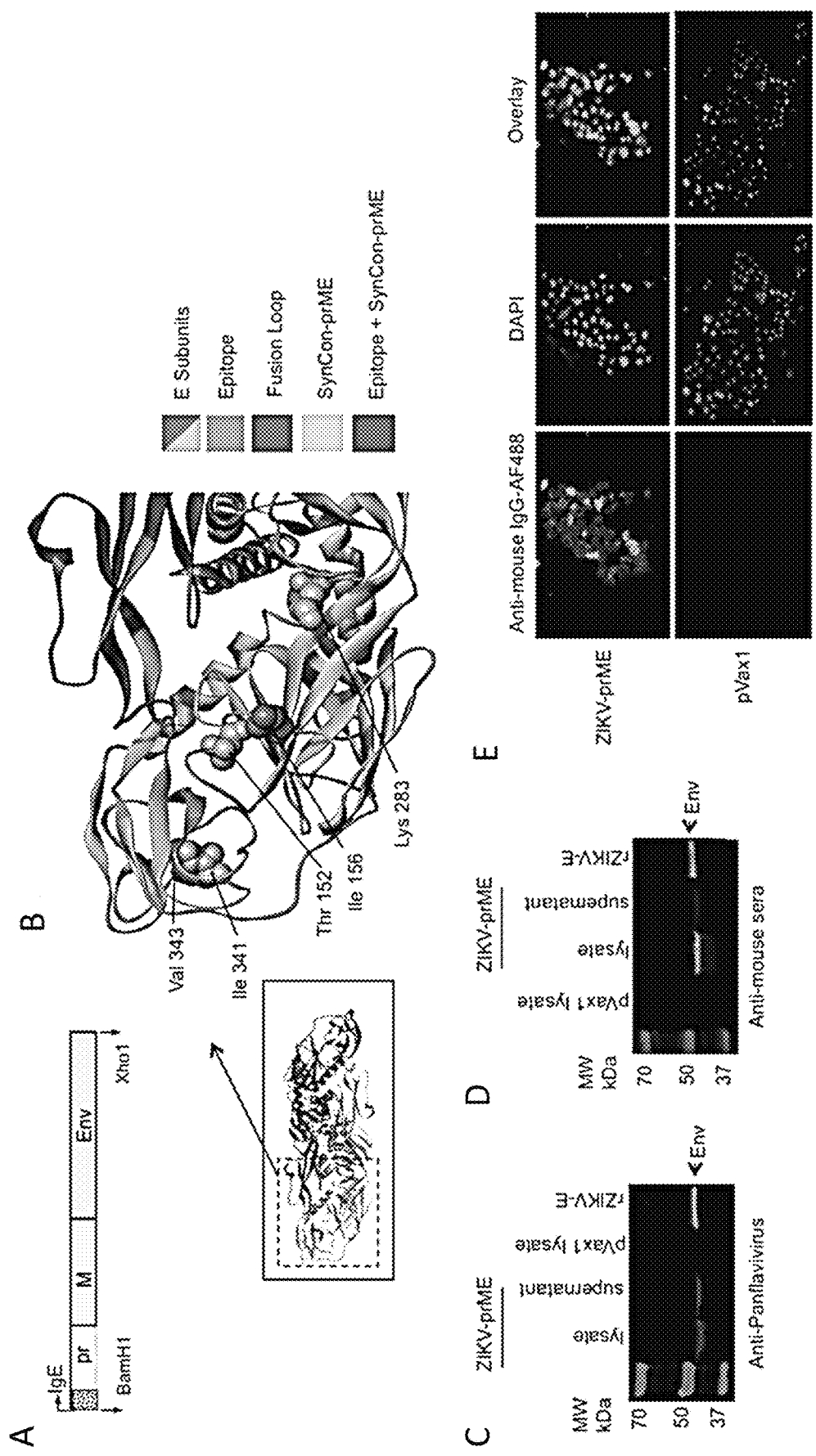
FIG. 24A-E

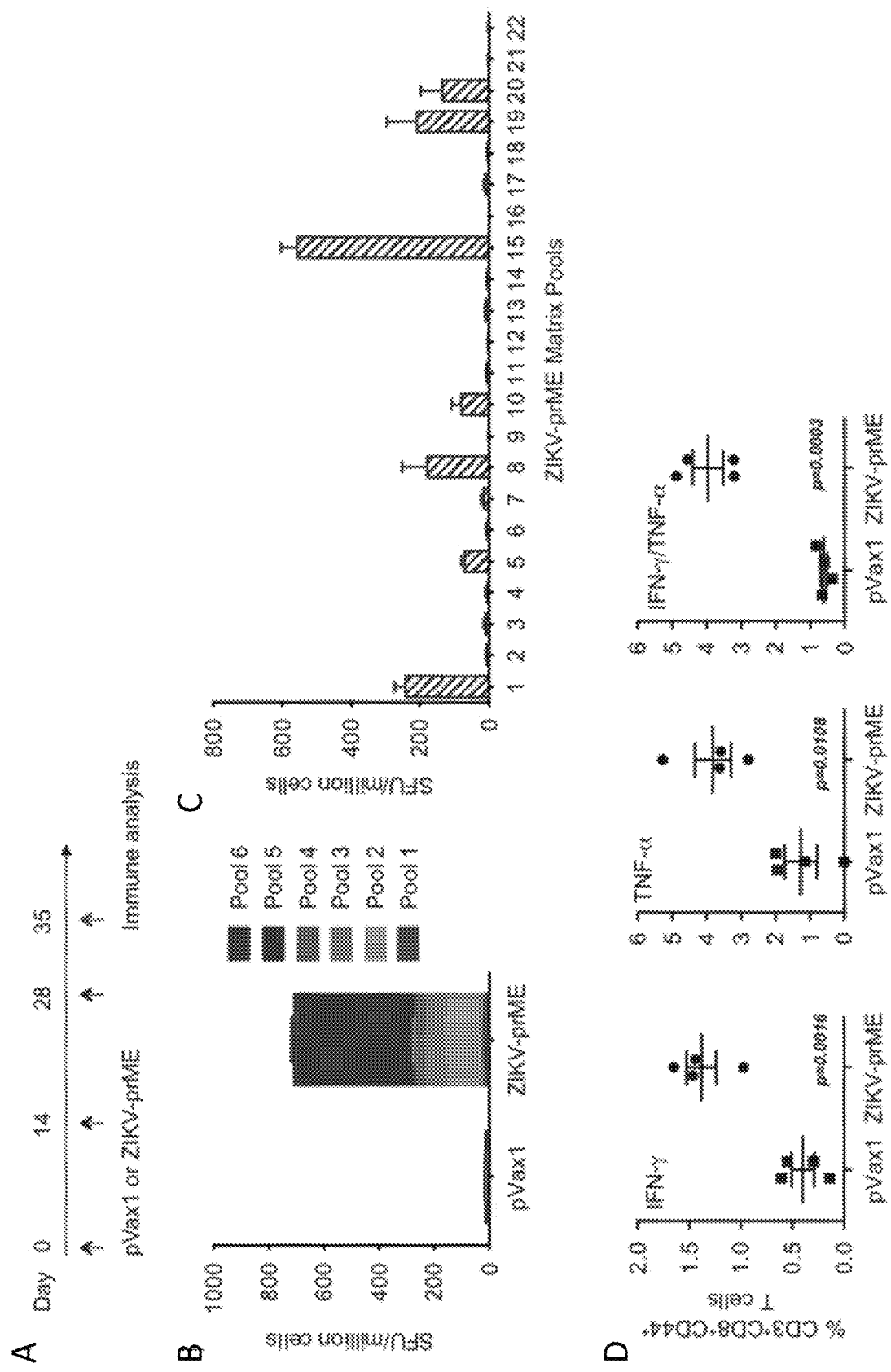
FIG. 25A-D

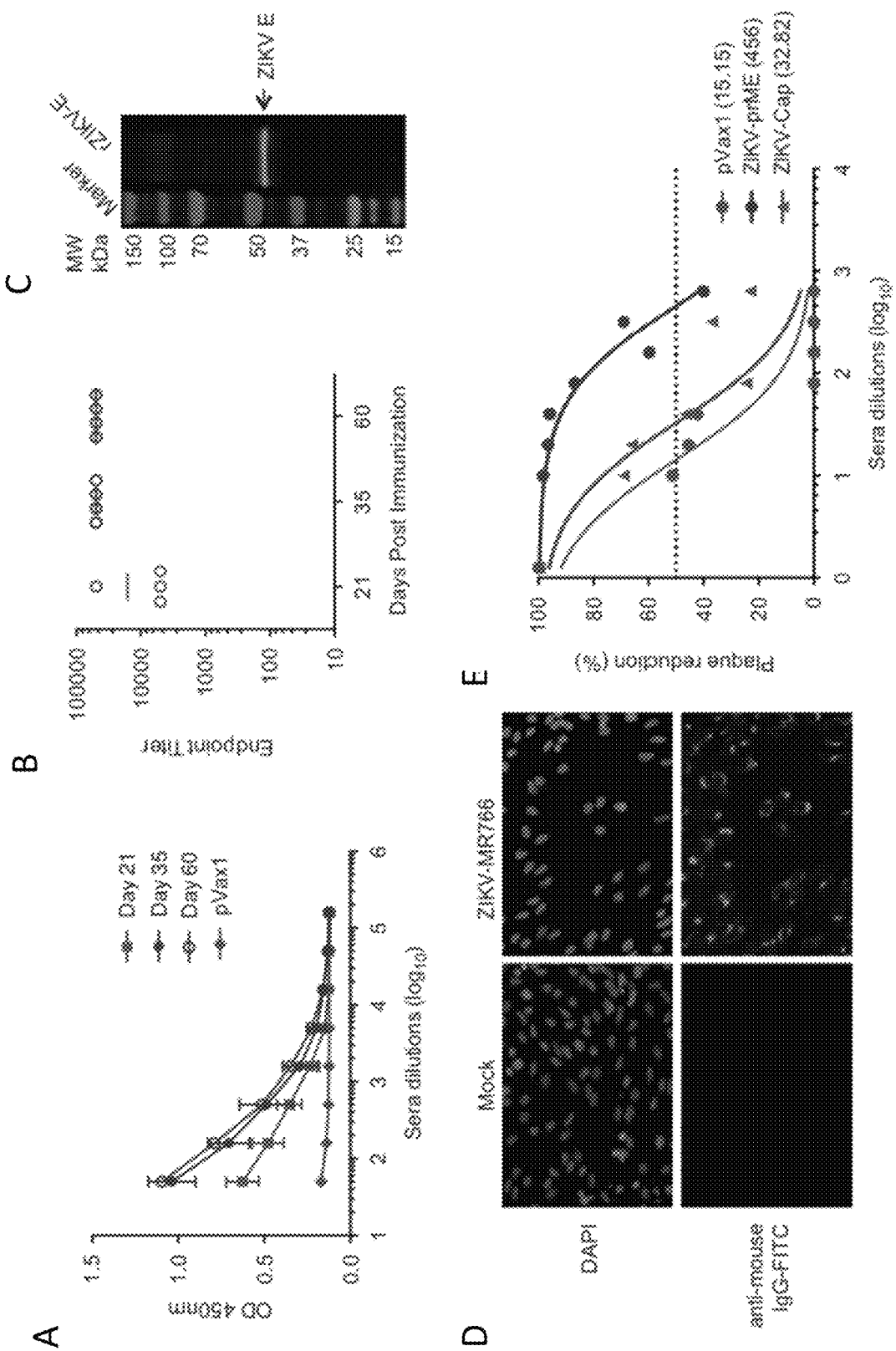
FIG. 26A-E

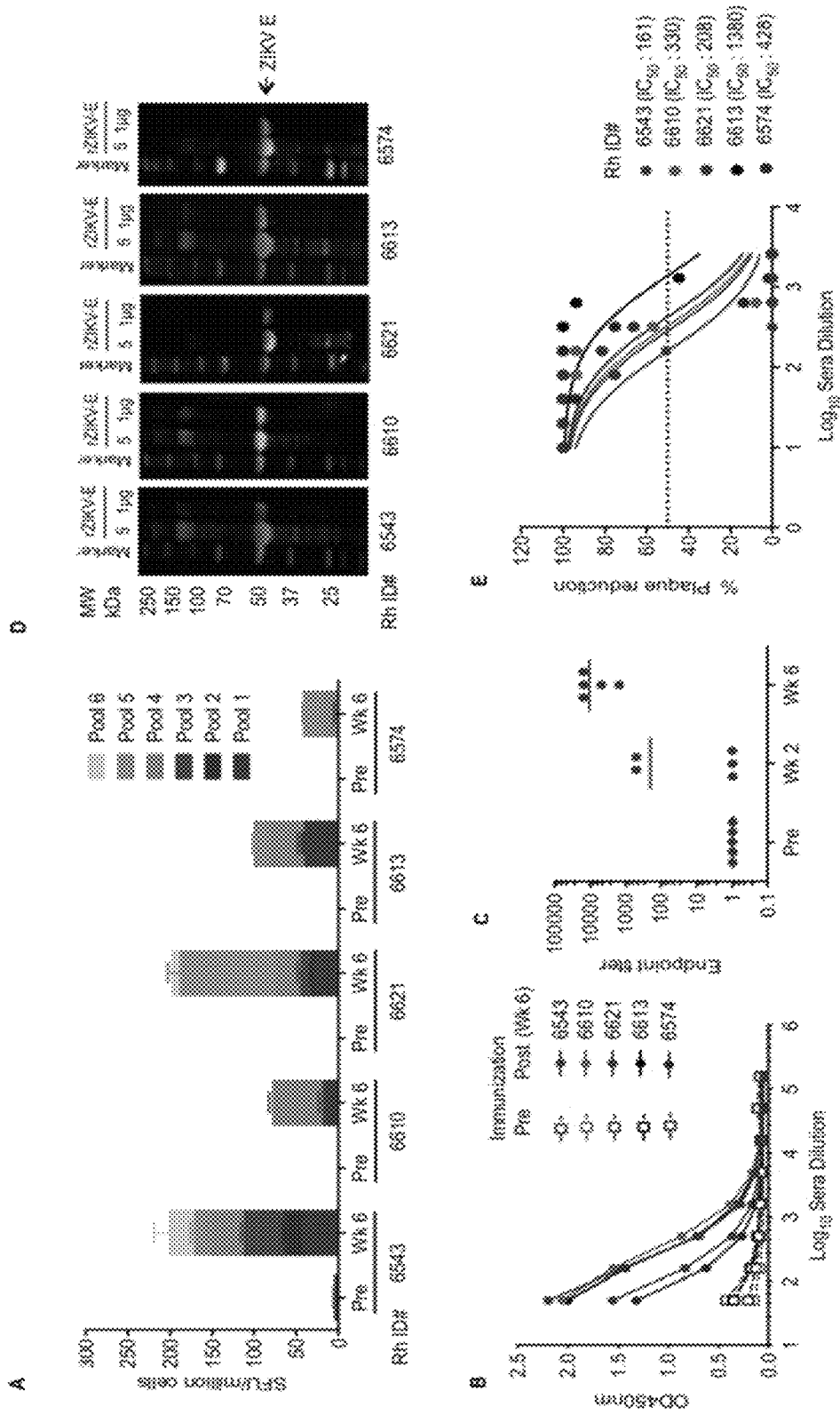
FIG. 27A-E

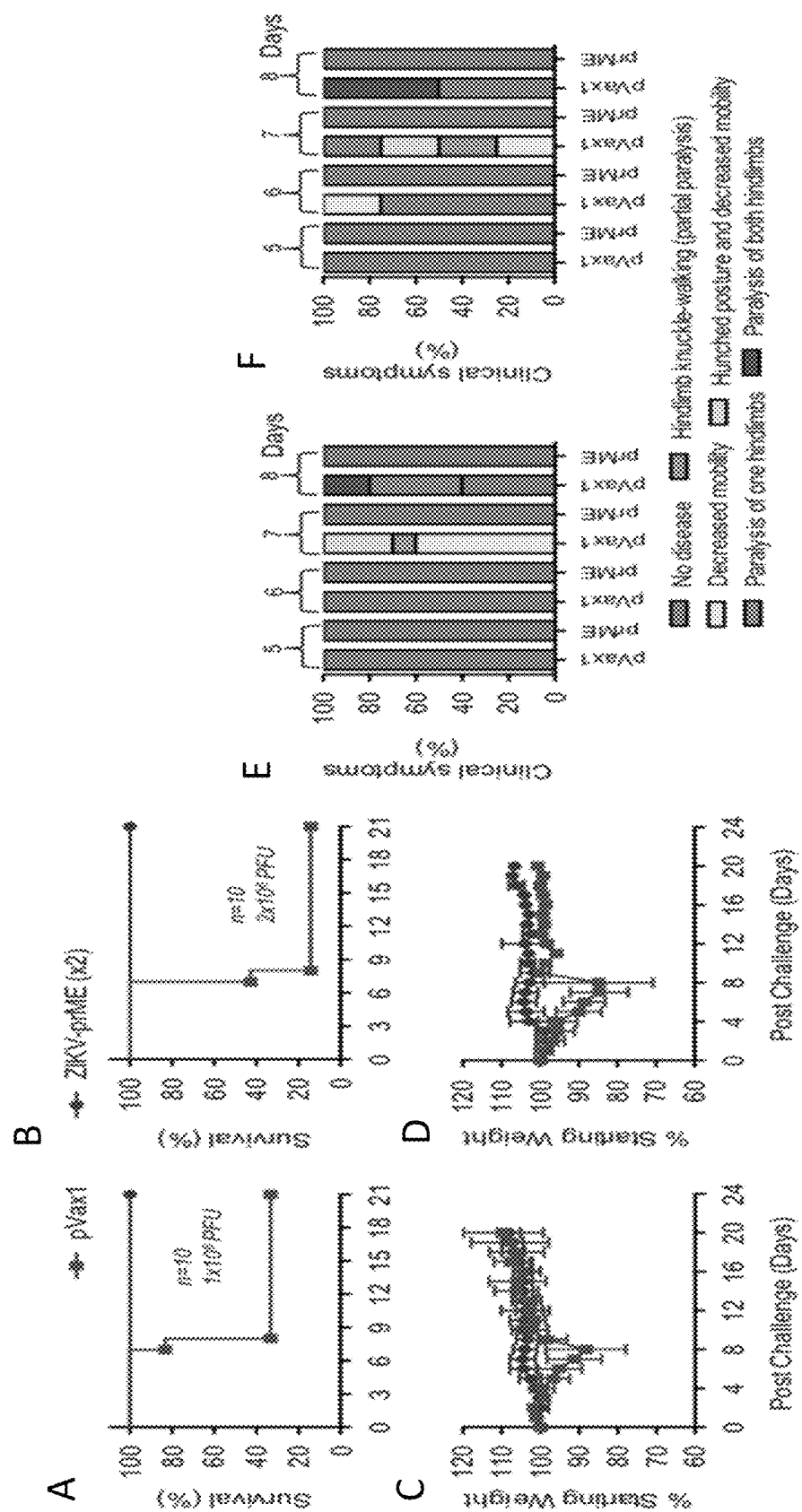
FIG. 28A-F

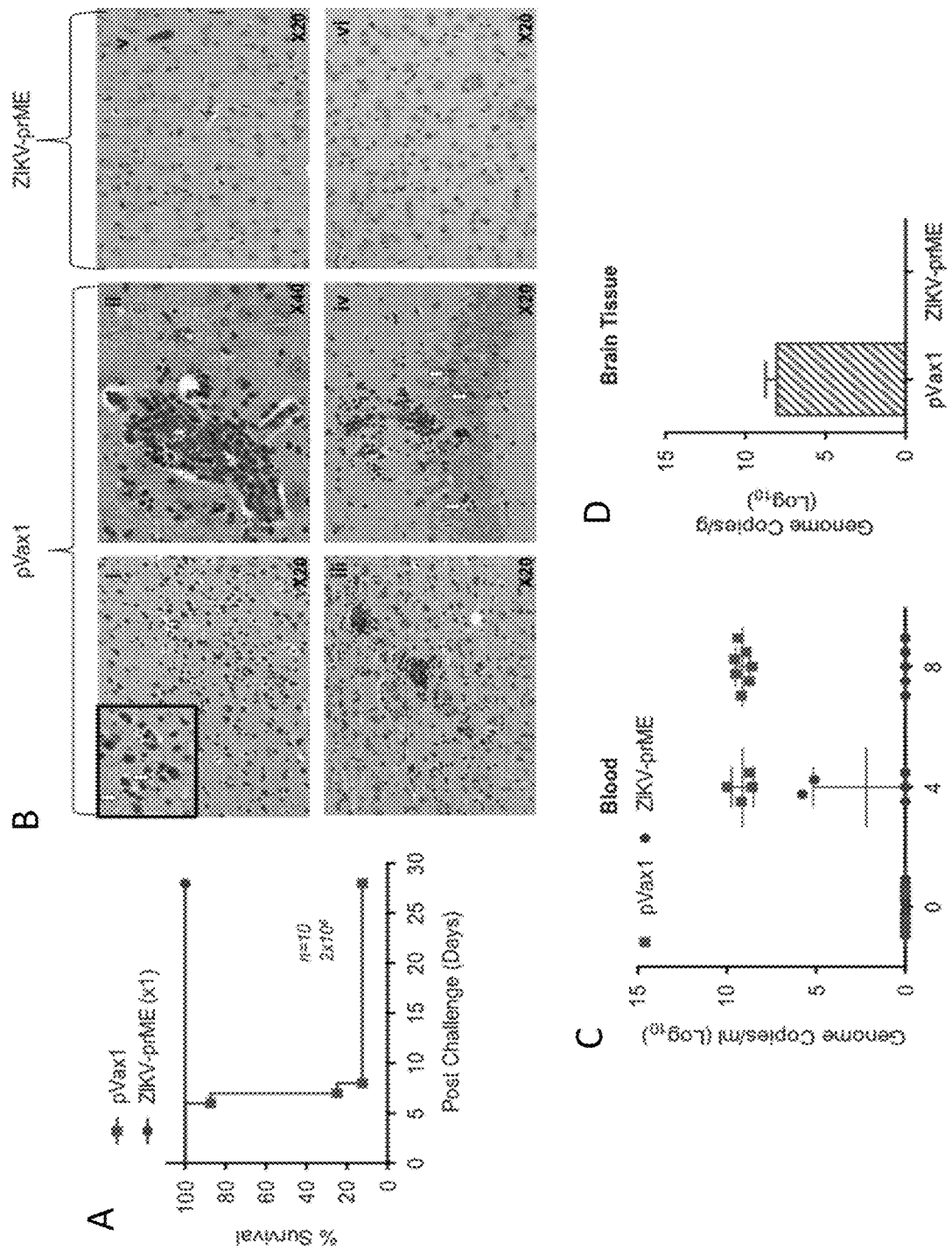
FIG. 29A-D

FIG. 30A-B

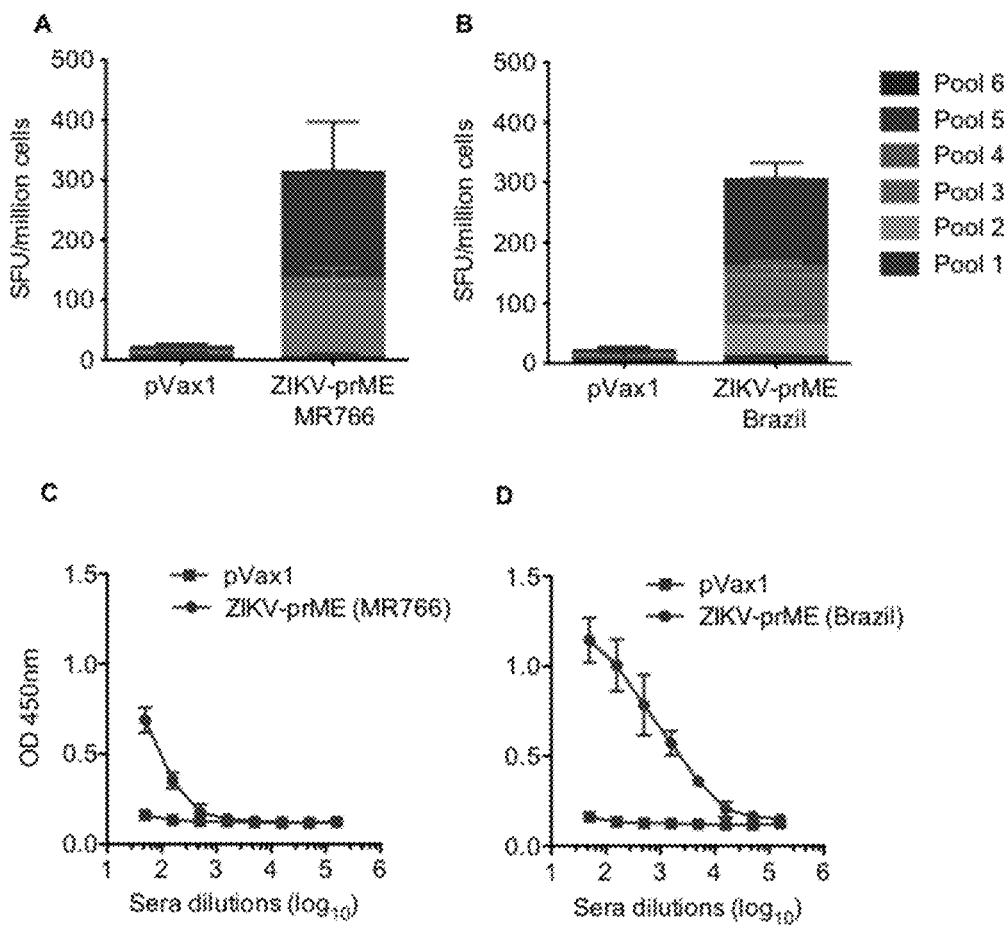
FIG. 31A-D

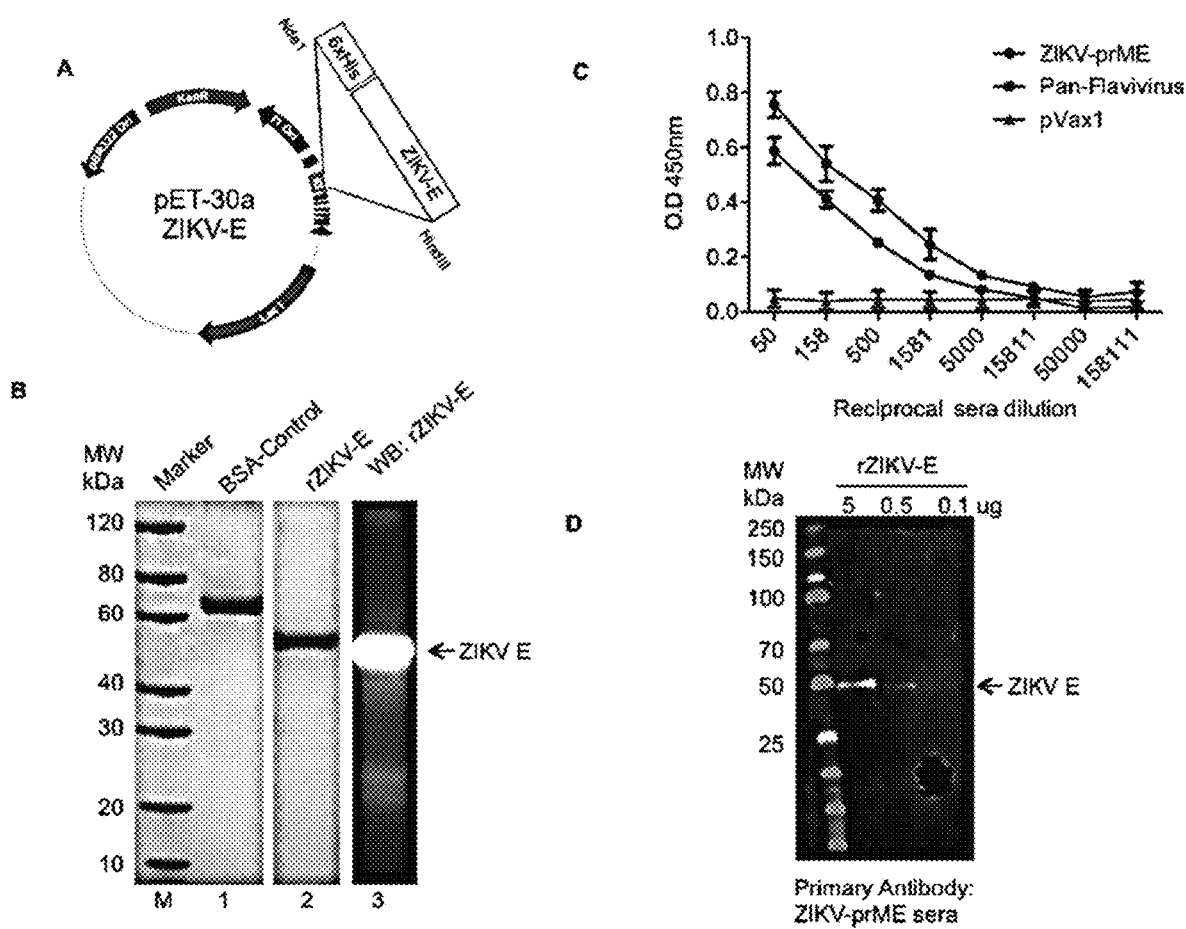
FIG. 32A-D

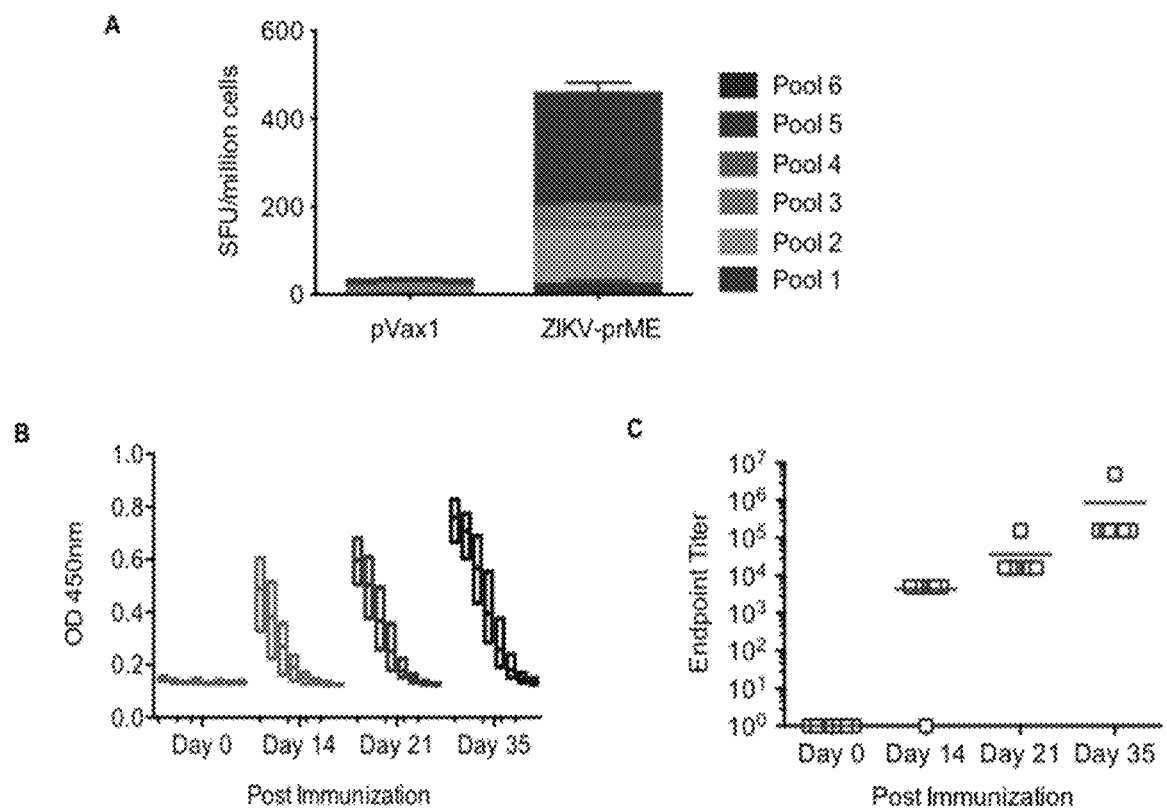
FIG. 33A-C

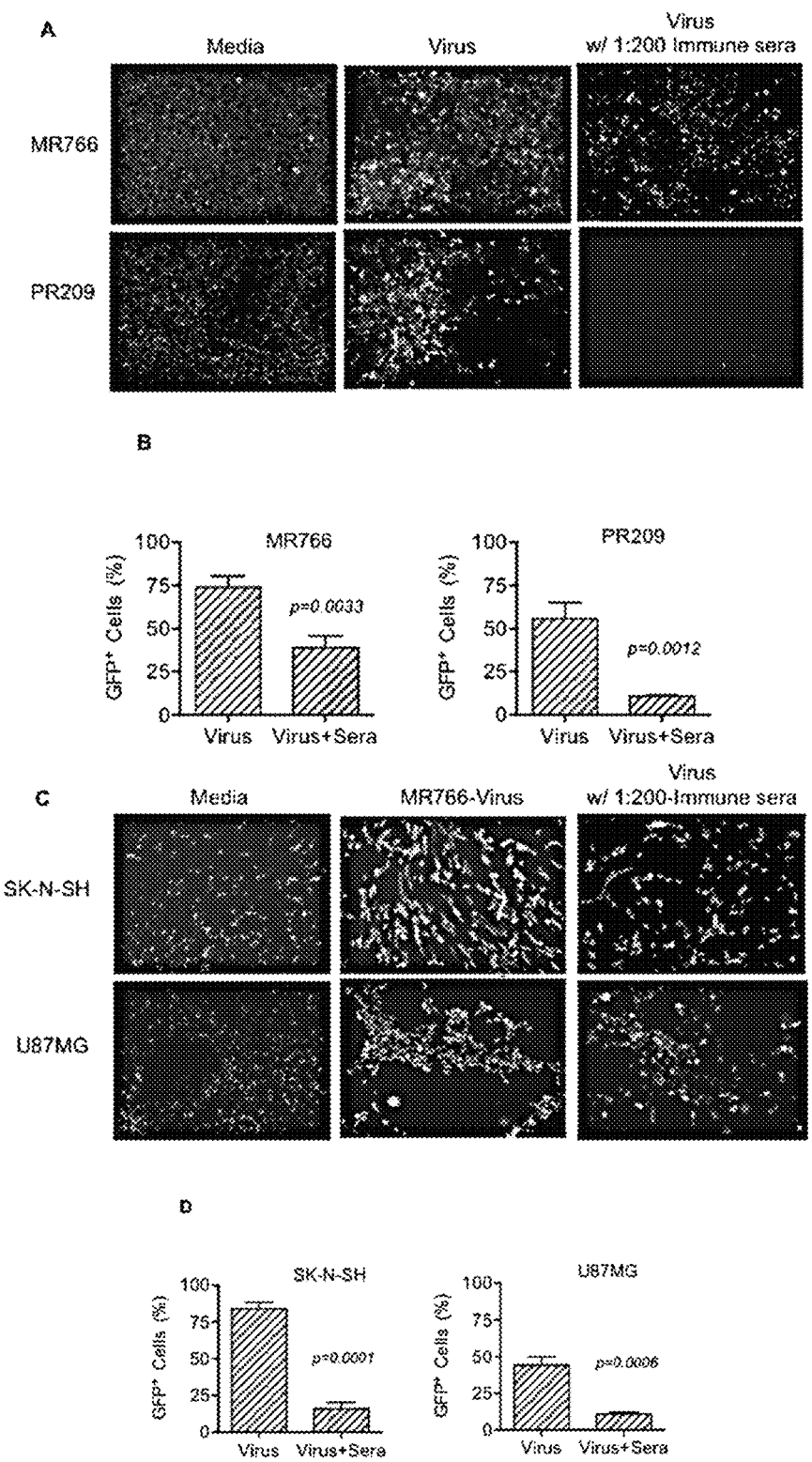
FIG. 34A-D

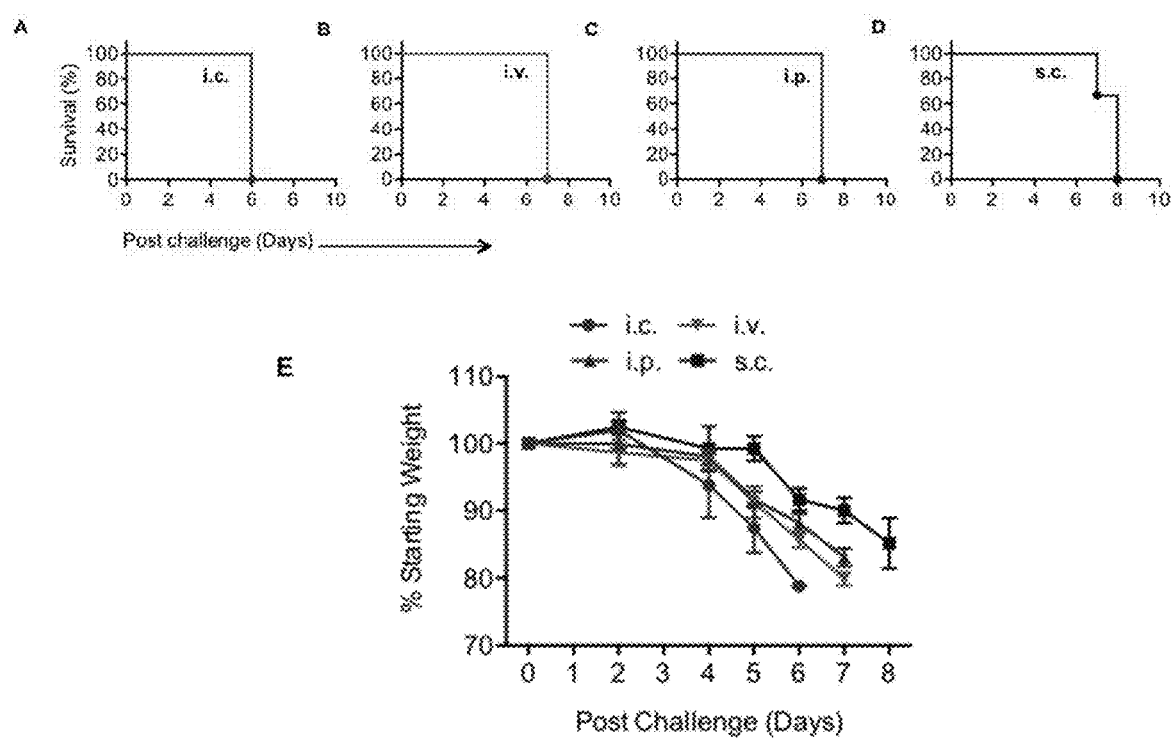
FIG. 35A-E

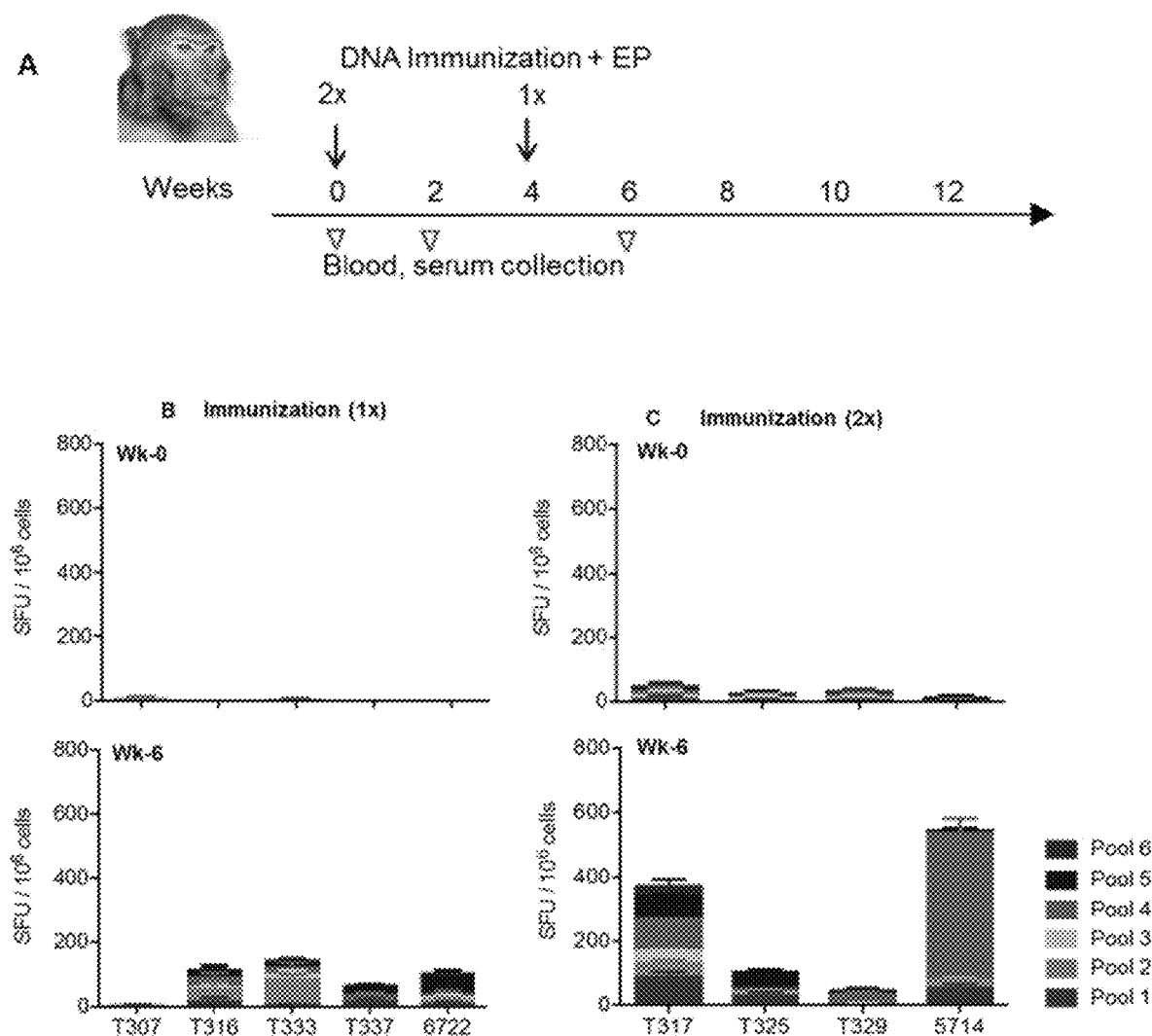
FIG. 36A-C

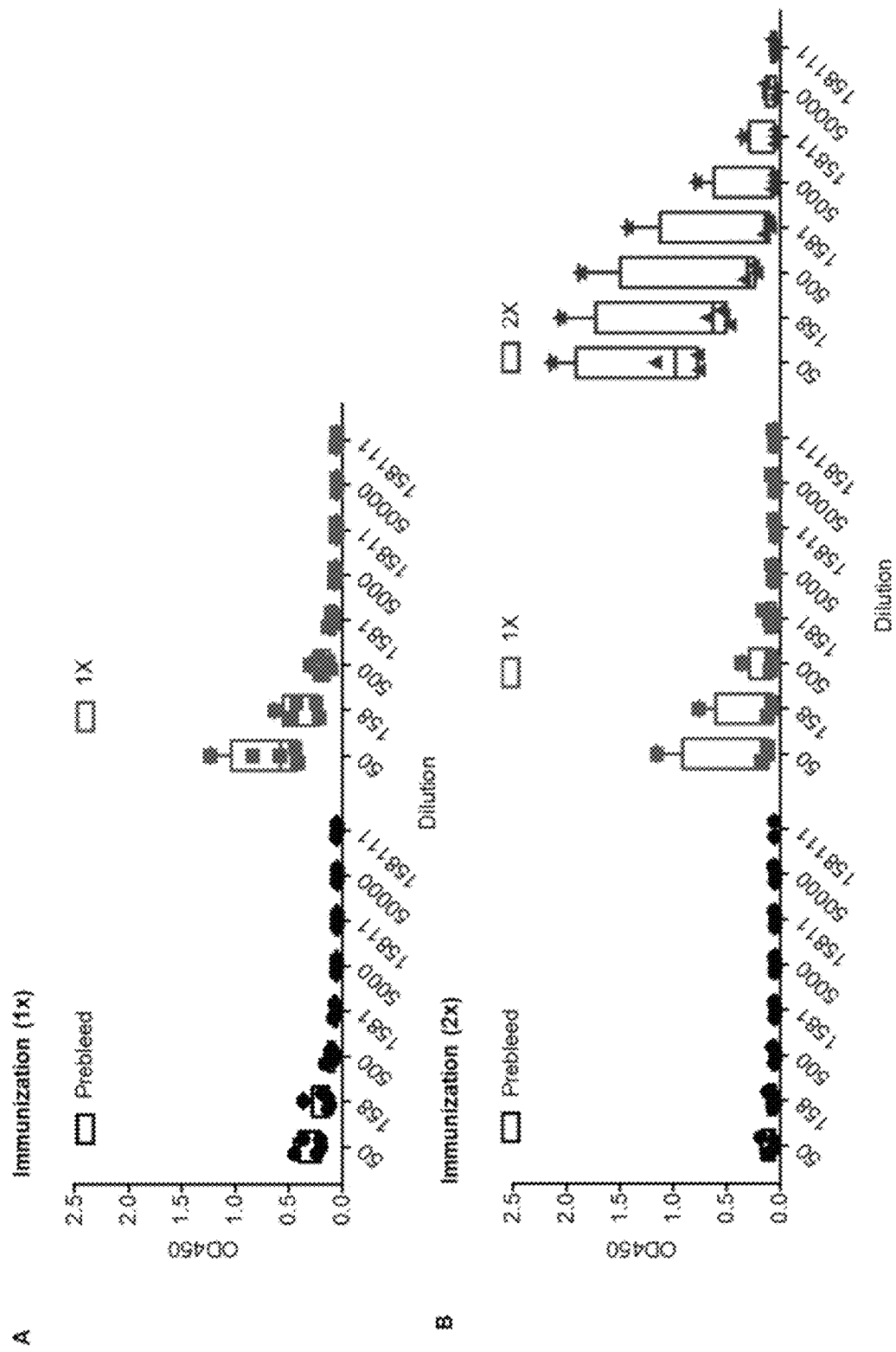
FIG. 37A-B

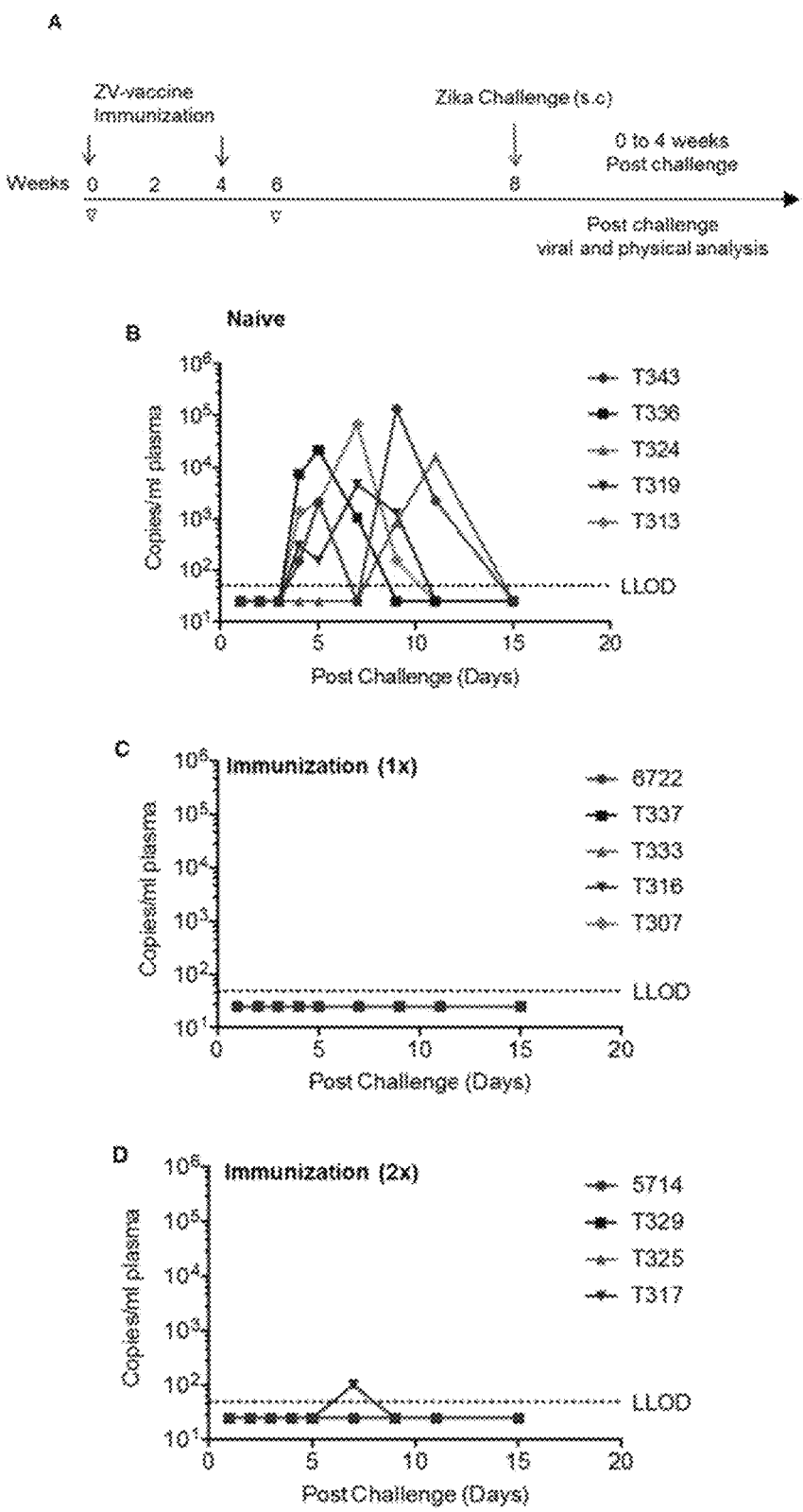
FIG. 38A-D

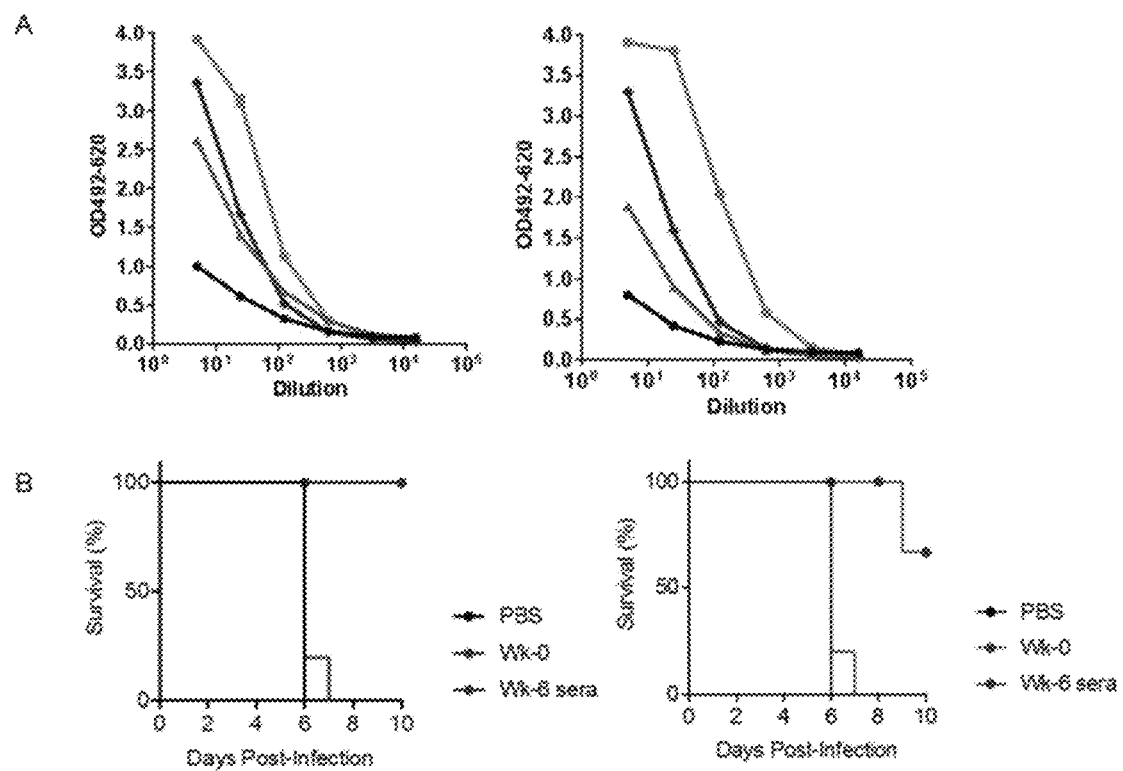
FIG. 39A-B

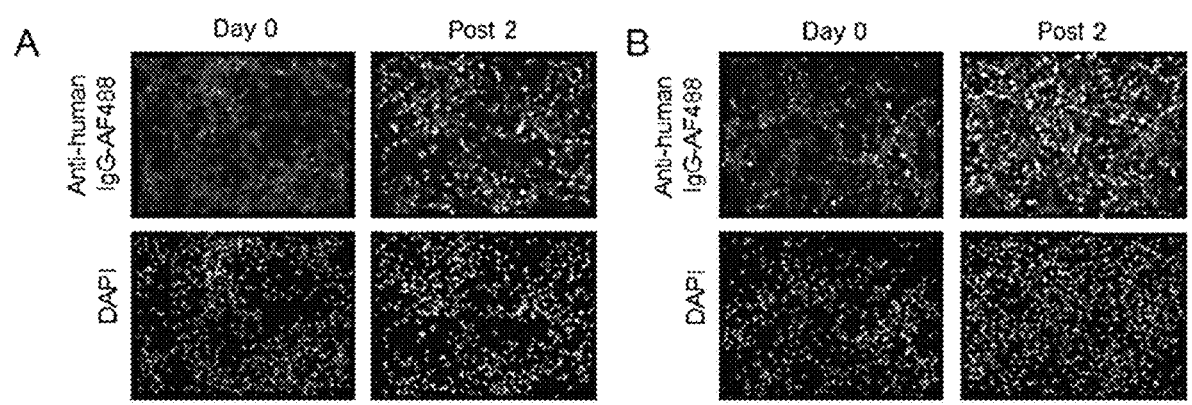
FIG. 40A-B

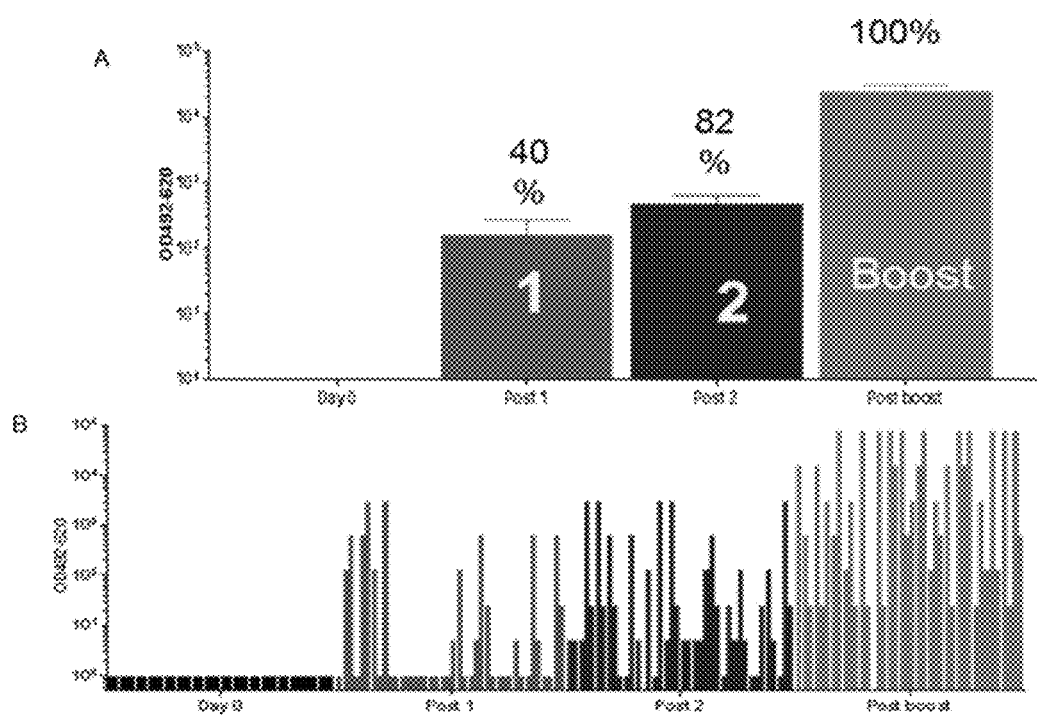
FIG. 41A-B

SEQUENCE LISTING

```
Sequence total quantity: 19
SEQ ID NO: 1              moltype = AA   length = 702
FEATURE                   Location/Qualifiers
REGION                    1..702
                          note = LS+pre+Membrane+Envelope (DIII domain; Transmembrane
                          I &II)
source                    1..702
                          mol_type = protein
                          organism = synthetic construct
SEQUENCE: 1
MDWTWILFLV AAATRVHSGI IGLLLTTAMA AEITRRGSAY YMYLDRNDAG EAISFPTTLG   60
MNKCYIQIMD LGHMCDATMS YECPMLDEGV EPDDVDCWCN TTSTWVVYGT CHHKKGEARR  120
SRRAVTLPSH STRKLQTRSQ TWLESREYTK HLIRVENWIF RNPGFALAAA AIAWLLGSST  180
SQKVIYLVMI LLIAPAYSIR CIGVSNRDFV EGMSGGTWVD VVLEHGGCVT VMAQDKPTVD  240
IELVTTTVSN MAEVRSYCYE ASISDMASDS RCPTQGEAYL DKQSDTQYVC KRTLVDRGWG  300
NGCGLFGKGS LVTCAKFTCS KKMTGKSIQP ENLEYRIMLS VHGSQHSGMI VNDIGHETDE  360
NRAKVEVTPN SPRAEATLGG FGSLGLDCEP RTGLDFSDLY YLTMNNKHWL VHKEWFHDIP  420
LPWHAGADTG TPHWNNKEAL VEFKDAHAKR QTVVVLGSQE GAVHTALAGA LEAEMDGAKG  480
RLFSGHLKCR LKMDKLRLKG VSYSLCTAAF TFTKVPAETL HGTVTVEVQY AGTDGPCKVP  540
AQMAVDMQTL TPVGRLITAN PVITESTENS KMMLELDPPF GDSYIVIGVG DKKITHHWHR  600
SGSTIGKAFE ATVRGAKRMA VLGDTAWDFG SVGGVFNSLG KGIHQIFGAA FKSLFGGMSW  660
FSQILIGTLL VWLGLNTKNG SISLTCLALG GVMIFLSTAV SA                    702

SEQ ID NO: 2              moltype = DNA   length = 2112
FEATURE                   Location/Qualifiers
misc_feature              1..2112
                          note = Zika prM-Env Consensus DNA
source                    1..2112
                          mol_type = other DNA
                          organism = synthetic construct
SEQUENCE: 2
atggactgga cctggattct gtttctggtc gctgctgcta caagagtgca ttctgggatt    60
attggactgc tgctgactac tgccatggca gcagagatca ccaggagagg cagcgcctac   120
tatatgtacc tggaccggtc tgatgccggc aaggccatca gctttgccac cacactgggc   180
gtgaataagt gccacgtgca gatcatggac ctgggccaca tgtgcgatgc caccatgtcc   240
tacgagtgtc caatgctgga cgagggcgtg gagcccgacg atgtggattg ctgctgtaac   300
accacatcta catgggtggt gtatggcacc tgtcaccaca agaaggagag ggcacggcgc   360
agcaggagag cagtgacact gccctctcac agcaccagga agctgcagac aagaagccaa   420
acctggctgg agtcccggga gtatacaaag cacctgatca aggtggagaa ctggatcttt   480
cgcaatccag gattcgcact ggtggcagtg gcaatcgcat ggctgctggg cagctccacc   540
tcccagaaag tgatctacct ggtcatgatc ctgctgatcg ccctgccta ttccatcagg    600
tgcatcggcg tgtctaatag agacttcgtg gagggcatgt ctggcggcac ctgggtggat   660
gtggtgctgg agcacggcgg atgcgtgaca gtgatggccc aggacaagcc aaccgtggat   720
atcgagctgg tgaccacaac cgtgagcaac atggccgagt gaggtccta ctgctatgag    780
gcctccatct ctgacatggc cagcgattcc agatgtccca cccagggcga ggcctacctg   840
gacaagcagt ccgatacaca gtacgtgtgc aagcgggacc tggtggacag gggatgggga   900
aatggatgtg gcctgtttgg caagggctct ctggtgacat gcgccaagtt cacctgttct   960
aagaagatga ccggcaagag catccagccc gagaacctgg agtacaggat catgctgagc  1020
gtgcacggca gccagcactc cggcatgaca gtgaacgaca tcggctatga gaccgatgag  1080
aatagggcca aggtggaggt gacacctaac agcccaagag ccgaggccac cctggccggc  1140
tttggctccc tgggactgga ctgcgagcct agaacagcc tggacttctc cgatctgtac  1200
tatctgacca tgaacaataa gcactggctg gtgcacaagg agtggtttca cgacatccca  1260
ctgccatggc acgcaggagc agatacagga accccacact ggaacaataa ggaggccctg  1320
gtggagttca aggatgccca cgccaagcgc cagacagtgg tggtgctggg cagccaggag  1380
ggagcagtgc acaccgccct ggcaggcgcc ctggaggcca gatgacgg cgccaagggc    1440
aagctgtttt ccggccacct gaagtgccgg ctgaagatgg ataagctgcg cctgaagggc  1500
gtgtcttaca gcctgtgcac agccgccttc accttcacca aggtgcctgc cgagacctg   1560
cacggcacag tgaccgtgga ggtgcagtat gccggcacag acggccctg taagatccct   1620
gtgcagatgg ccgtggatat gcagacactg acccctgtgg gccggctgat caccgcaaat  1680
ccagtgatca cagagtccac cgagaactct aagatgatgc tggagctgga ccctcccttc  1740
ggcgacagct acatcgtgat cggcgtgggc gacaagaaga tcacacacca ctggcaccgc  1800
tccggctcta caatcggcaa ggccttcgag gcaaccgtgc ggggcgccaa gaggatggcc  1860
```

```
gtgctgggcg acaccgcatg ggattttggc tccgtgggcg gcgtgttcaa ctctctgggc    1920
aagggcatcc accagatctt cggcgccgcc tttaagtctc tgttcggcgg aatgtcttgg    1980
ttcagccaga tcctgatcgg cacactgctg gtgtggctgg gcctgaacac caagaatggc    2040
agcatctctc tgacttgtct ggccctggga ggcgtgatga ttttcctgtc cactgccgtg    2100
tctgcctgat aa                                                         2112

SEQ ID NO: 3              moltype = AA   length = 702
FEATURE                   Location/Qualifiers
REGION                    1..702
                          note = Zika prM-Env Consensus protein
source                    1..702
                          mol_type = protein
                          organism = synthetic construct
SEQUENCE: 3
MDWTWILFLV AAATRVHSGI IGLLLTTAMA AEITRRGSAY YMYLDRSDAG KAISFATTLG     60
VNKCHVQIMD LGHMCDATMS YECPMLDEGV EPDDVDCWCN TTSTWVVYGT CHHKKGEARR    120
SRRAVTLPSH STRKLQTRSQ TWLESREYTK HLIKVENWIF RNPGFALVAV AIAWLLGSST    180
SQKVIYLVMI LLIAPAYSIR CIGVSNRDFV EGMSGGTWVD VVLEHGGCVT VMAQDKPTVD    240
IELVTTTVSN MAEVRSYCYE ASISDMASDS RCPTQGEAYL DKQSDTQYVC KRTLVDRGWG    300
NGCGLFGKGS LVTCAKFTCS KKMTGKSIQP ENLEYRIMLS VHGSQHSGMT VNDIGYETDE    360
NRAKVEVTPN SPRAEATLGG FGSLGLDCEP RTGLDFSDLY YLTMNNKHWL VHKEWFHDIP    420
LPWHAGADTG TPHWNNKEAL VEFKDAHAKR QTVVVLGSQE GAVHTALAGA LEAEMDGAKG    480
KLFSGHLKCR LKMDKLRLKG VSYSLCTAAF TFTKVPAETL HGTVTVEVQY AGTDGPCKIP    540
VQMAVDMQTL TPVGRLITAN PVITESTENS KMMLELDPPF GDSYIVIGVG DKKITHHWHR    600
SGSTIGKAFE ATVRGAKRMA VLGDTAWDFG SVGGVFNSLG KGIHQIFGAA FKSLFGGMSW    660
FSQILIGTLL VWLGLNTKNG SISLTCLALG GVMIFLSTAV SA                        702

SEQ ID NO: 4              moltype = DNA   length = 1119
FEATURE                   Location/Qualifiers
misc_feature              1..1119
                          note = Zika NS1 DNA
source                    1..1119
                          mol_type = other DNA
                          organism = synthetic construct
SEQUENCE: 4
atggactgga cttggattct gttcctggtg gctgccgcta caagagtgca tagcgtggga     60
tgcagcgtgg acttcagcaa gaaggagacc cgctgcggaa caggcgtgtt cgtgtacaac    120
gacgtggagg cttggagaga ccggtacaag taccaccccg atagccctag aagactggcc    180
gcagccgtga acaggcttg ggaagaggga atttgcggaa tcagcagcgt gtcccggatg    240
gagaacatca tgtggaagag cgtggagggc gagctgaacg ctatcctgga ggagaacggc    300
gtgcagctga gtggtcgt gggatcagtg aagaacccca tgtggagagg ccctcagagg    360
ctgccagtgc cagtgaacga actgcctcac ggttggaagg cttggggcaa gagctacttc    420
gtgagggccg ccaagaccaa caacagcttc gtggtggacg gcgataccct caaggagtgt    480
cctctgaagc accgggcttg gaacagcttc ctggtggaag accacggctt ggcgtgttc    540
cacacaagcg tctggctgaa ggtccgcgaa gactacagcc tggagtgcga tccagcagtg    600
atcggcacag ccgtgaaggg aaaagaggcc gctcacagcg acctgggcta ttggatcgag    660
agcgagaaga cgacacttg gaggctgaag cgggcccacc tgatcgagat gaagacttgc    720
gagtggccca gagccacac tctgtggaca gacggcgtgg aagagagcga cctgatcatc    780
cctaagagcc tggccggacc tctgtctcat cacaacacca gggagggcta cagaacccag    840
gtgaagggac cttggcacag cgaagagctg gagatccgct cgaggagtg tccaggaacc    900
aaggtgcacg tggaggagac ttgcggaacc agaggcccta gcctgagaag cacaacagcc    960
agcggacgcg tgatcgagga gtggtgttgt agggagtgca ccatgcctcc tctgagcttc   1020
agggccaagg acggttgttg tacgcatg gagatcaggc ccagaaagga gccagagagc   1080
aacctcgtgc ggtctatggt gacagccgga agctgataa                           1119

SEQ ID NO: 5              moltype = AA   length = 371
FEATURE                   Location/Qualifiers
REGION                    1..371
                          note = Zika NS1 Protein
source                    1..371
                          mol_type = protein
                          organism = synthetic construct
SEQUENCE: 5
MDWTWILFLV AAATRVHSVG CSVDFSKKET RCGTGVFVYN DVEAWRDRYK YHPDSPRRLA     60
AAVKQAWEEG ICGISSVSRM ENIMWKSVEG ELNAILEENG VQLTVVVGSV KNPMWRGPQR    120
LPVPVNELPH GWKAWGKSYF VRAAKTNNSF VVDGDTLKEC PLKHRAWNSF LVEDHGFGVF    180
HTSVWLKVRE DYSLECDPAV IGTAVKGKEA AHSDLGYWIE SEKNDTWRLK RAHLIEMKTC    240
EWPKSHTLWT DGVEESDLII PKSLAGPLSH HNTREGYRTQ VKGPWHSEEL EIRFEECPGT    300
KVHVEETCGT RGPSLRSTTA SGRVIEEWCC RECTMPPLSF RAKDGCWYGM EIRPRKEPES    360
NLVRSMVTAG S                                                          371

SEQ ID NO: 6              moltype = DNA   length = 438
FEATURE                   Location/Qualifiers
misc_feature              1..438
                          note = Zika Capsid DNA
source                    1..438
                          mol_type = other DNA
                          organism = synthetic construct
```

```
SEQUENCE: 6
atggactgga cttggatcct gtttctggtg gccgccgcca caagagtgca tagcaagaac  60
cccaagaaga agagcggcgg cttcaggatc gtgaacatgc tgaagcgggg cgtggctaga  120
gtgaaccctc tgggaggcgg actgaagaga ctgccagcag gactgctcct gggacacgga  180
cctattcgca tggtgctggc catcctggct ttcctgaggt tcaccgccat caagcccagc  240
ctgggactga tcaaccgctg ggggttcagtc ggcaagaagg aggccatgga gatcatcaag  300
aagttcaaga aggacctggc cgccatgctg aggatcatca acgcccggaa ggagcggaag  360
agaagaggag ccgacaccag catcggcatc atcggactgc tgctgacaac cgccatggct  420
gccgagatct gatgatga                                                438

SEQ ID NO: 7           moltype = AA  length = 143
FEATURE                Location/Qualifiers
REGION                 1..143
                       note = Zika Capsid Protein
source                 1..143
                       mol_type = protein
                       organism = synthetic construct
SEQUENCE: 7
MDWTWILFLV AAATRVHSKN PKKKSGGFRI VNMLKRGVAR VNPLGGGLKR LPAGLLLGHG  60
PIRMVLAILA FLRFTAIKPS LGLINRWGSV GKKEAMEIIK KFKKDLAAML RIINARKERK  120
RRGADTSIGI IGLLLTTAMA AEI                                          143

SEQ ID NO: 8           moltype = DNA  length = 2130
FEATURE                Location/Qualifiers
misc_feature           1..2130
                       note = Zika prM-Env MR766 DNA
source                 1..2130
                       mol_type = other DNA
                       organism = synthetic construct
SEQUENCE: 8
atggactgga cttggattct gttcctggtg gctgccgcta caagagtgca ttcaggagcc  60
gacacctcta tcggcatcgt gggactgctg ctgaccacag ccatggccgc cgaaattacc  120
aggaggggca gcgcctacta catgtacctg gacagaagcg acgccggaaa agccatcagc  180
ttcgccacaa ccctgggcgt caacaagtgc cacgtgcaga tcatggacct gggccacatg  240
tgcgacgcca caatgagcta cgagtgccct atgctggacg agggagtgga accagacgac  300
gtcgactgtt ggtgcaacac cacctccact tgggtcgtgt acggcacttg ccaccacaag  360
aagggcgagg ccagaagaag cagaagagcc gtgaccctgc ctagccacag caccagaaag  420
ctgcagacca ggagccagac ttggctggaa agccgcgagt acaccaagca cctgatcaag  480
gtggagaatt ggatcttccg gaaccccggc ttcacactgg tggccgtggc aatcgcttgg  540
ctgctgggat ctagcaccag ccagaaagtg atctacctgg tcatgatcct gctgatcgcc  600
ccagcctaca gcatccgctg tatcggagtg agcaaccggg acttcgtgga gggaatgagc  660
ggaggaactt gggtggacgt ggtgctggaa cacggaggtt gcgtgacagt gatggctcag  720
gacaagccca ccgtggatat cgagctggtg accaccaccg tgtccaacat ggccgaagtg  780
cgcagctact gctacgaggc cagtatctcc gacatggcca gcgatagccg ctgtcctaca  840
cagggagagg cctatctgga caagcagagc gacacccagt acgtctgcaa gaggaccctc  900
gtggatagag gctggggaaa cggttgcgga ctgttcggaa agggcagcct cgtgacttgc  960
gccaagttca cttgcagcaa gaagatgacc ggcaagtcta tccagcccga gaacctggag  1020
taccggatca tgctgagcgt gcacggaagc cagcacagcg gcatgatcgt gaacgacgag  1080
ggatacgaga ccgacgagaa cagggccaag gtggaagtga cccctaacag ccctagagcc  1140
gaagccacac tgggaggatt tggcagcctg ggactggatt gcgagcctag aacaggcctg  1200
gacttcagcg acctgtacta cctgaccatg aacaacaagc attggctggt gcacaaggag  1260
tggttccacg acatccctct gccttggcac gcaggagccg atacaggcac acctcattgg  1320
aacaacaagg aggccctggt ggagttcaag gacgctcacg ccaagagaca gacagtggtg  1380
gtgctgggaa gccaggaagg agcagtgcat acagccctgg caggagctct ggaagcagaa  1440
atggacggcg ctaagggcag actgttcagc ggacacctca agtgccggct gaagatggac  1500
aagctgcggc tgaagggcgt gtcttacagc ctctgcaccg cagccttcac cttcaccaag  1560
gtgccagcag agacactgca cggaacagtg accgtggaag tgcagtacgc cggaacagac  1620
ggaccttgca aagtgccagc ccagatggca gtggacatgc agacactgac cccagtggga  1680
aggctgatca ccgctaaccc cgtcatcacc gagagcaccg agaacagcaa gatgatgctg  1740
gagctggacc cccccttcgg cgatagctac atcgtgatcg gcgtgggcga caagaagatc  1800
acccaccatt ggcacagaag cggcagcaca atcggcaagg ctttcgaggc caccgtgaga  1860
ggagctaaga gaatggccgt gctgggagac accgcttggg attttggcag cgtgggagga  1920
gtgttcaaca gcctgggcaa gggcatccac cagatcttcg gagccgcctt caagagcctg  1980
ttcggcggca tgtcttggtt cagccagatc ctgatcggaa cactcctcgt ctggctggga  2040
ctgaacacca agaacggcag catcagcctg acttgtctgg ccctgggagg cgtgatgatc  2100
ttcctgagca ccgccgtgtc cgcttgataa                                    2130

SEQ ID NO: 9           moltype = AA  length = 708
FEATURE                Location/Qualifiers
REGION                 1..708
                       note = Zika prM-Env MR766 Protein
source                 1..708
                       mol_type = protein
                       organism = synthetic construct
SEQUENCE: 9
MDWTWILFLV AAATRVHSGA DTSIGIVGLL LTTAMAAEIT RRGSAYYMYL DRSDAGKAIS  60
FATTLGVNKC HVQIMDLGHM CDATMSYECP MLDEGVEPDD VDCWCNTTST WVVYGTCHHK  120
KGEARRSRRA VTLPSHSTRK LQTRSQTWLE SREYTKHLIK VENWIFRNPG FTLVAVAIAW  180
LLGSSTSQKV IYLVMILLIA PAYSIRCIGV SNRDFVEGMS GGTWVDVVLE HGGCVTVMAQ  240
```

```
DKPTVDIELV TTTVSNMAEV RSYCYEASIS DMASDSRCPT QGEAYLDKQS DTQYVCKRTL    300
VDRGWGNGCG LFGKGSLVTC AKFTCSKKMT GKSIQPENLE YRIMLSVHGS QHSGMIVNDE    360
GYETDENRAK VEVTPNSPRA EATLGGFGSL GLDCEPRTGL DFSDLYYLTM NNKHWLVHKE    420
WFHDIPLPWH AGADTGTPHW NNKEALVEFK DAHAKRQTVV VLGSQEGAVH TALAGALEAE    480
MDGAKGRLFS GHLKCRLKMD KLRLKGVSYS LCTAAFTFTK VPAETLHGTV TVEVQYAGTD    540
GPCKVPAQMA VDMQTLTPVG RLITANPVIT ESTENSKMML ELDPPFGDSY IVIGVGDKKI    600
THHWHRSGST IGKAFEATVR GAKRMAVLGD TAWDFGSVGG VFNSLGKGIH QIFGAAFKSL    660
FGGMSWFSQI LIGTLLVWLG LNTKNGSISL TCLALGGVMI FLSTAVSA                708

SEQ ID NO: 10          moltype = DNA  length = 2130
FEATURE                Location/Qualifiers
misc_feature           1..2130
                       note = Zika prM-Envelope Brazil Construct DNA
source                 1..2130
                       mol_type = other DNA
                       organism = synthetic construct
SEQUENCE: 10
atggactgga cttggattct gttcctggtg gctgccgcta caagagtgca ttcaggagcc     60
gacacatcag tgggcatcgt gggactgctg ctgacaacag ctatggccgc cgaagtgacc    120
agaagaggca gcgcctacta catgtacctg gaccggaacg acgccggaga ggccattagc    180
tttcctacca cccctgggca tgaacaagtg tacatccaga tcatggacct gggccacatg    240
tgcgacgcta caatgagcta cgagtgcccc atgctggacg aaggagtgga gccagacgac    300
gtggattgtt ggtgcaacac cacctccact tgggtcgtgt acggcacctg tcaccacaaa    360
aagggcgaag ccaggagaag cagaagagcc gtgaccctgc ctagccactc taccaggaag    420
ctgcagacca ggagccagac ttggctggag agcagggagt acaccaagca cctgatccgc    480
gtggagaatt ggatcttcag aaaccccggc ttcgccctgg cagccgcgcc aattgcttgg    540
ctgctgggat ctagcaccag ccagaaggtc atctacctgg tcatgatcct gctgatcgcc    600
cccgcttaca gcatccgctg tatcggcgtg tccaacaggg acttcgtgga gggcatgagc    660
ggaggaactt gggtggacgt ggtgctgaa cacggaggtt gtgtgaccgt gatggctcag    720
gacaagccta ccgtggacat cgagctggtg accacaaccg tgtccaacat ggccgaggtc    780
cgcagctatt gctacgaggc cagcatcagc gatatggcca gcgatagcag gtgtccacc     840
cagggtgaag cttacctgga caagcagagc gacacccagt acgtgtgcaa gcggacactg    900
gtggatagag ctggggaaa cggttgcggc ctgtttggca agggaagcct ggtgacctgc    960
gccaagttcg catgcagcaa gaagatgacc ggcaagagca tccagcccga gaacctggag   1020
taccggatca tgctgagcgt gcacggatct cagcatagcg gaatgatcgt gaacgacacc   1080
ggccacgaga ccgacgaaaa cagggccaag gtgaaatca cccccaactc tcctagagcc   1140
gaggccacac tgggagggttt tggaagcctg gcctggatt gcgagcctag aacaggcctg   1200
gacttcagcg acctgtacta cctgaccatg aacaacaagc attggctggt gcacaaggag   1260
tggttccacg acatccctct gccttggcac gcaggagcag ataccggagc cccccattgg   1320
aacaacaagg aggccctggt ggagttcaag acgctcacg ccaagagaca gacagtggtg   1380
gtgctgggaa gccaggaagg agcagtgcac acagctctgg caggagctct ggaagccgaa   1440
atggacggag ccaagggcag actgtcctcc ggacacctca gtgccggct gaagatggac   1500
aagctgcgac tgaagggcgt gtcttatagc tctgcagcg ccgctttac cttcaccaag   1560
atccccgcag agaccctgca cggaacagtg accgtgaag tgcagtacgc cggaacagac   1620
ggaccttgca aggtgccagc tcagatggca gtggacatgc agaccctgac cccagtggga   1680
agactgatca ccgctaaccc cgtcatcacc gagagcaccg agaacagcaa gatgatgctg   1740
gagctgacc ccccttcgg cgatagctac atcgtgatcg gcgtgggcga gaaaaagatc   1800
acccaccatt ggcacaggag cggcagcaca atcggcaagg cctttgaggc caccgtgaga   1860
ggagccaaga gaatggccgt gctgggagat accgcttggg atttcggcag cgtgggaggc   1920
gccctgaaca gcctgggcaa gggcattcac cagatcttcg gagccgcctt caagagcctg   1980
ttcggcggca tgtcttggtt cagccagatc ctgatcggca cactgctcat gtggctgggc   2040
ctgaacacca gaacggcgca catcagcctg atgtgtctgg ctctgggagg cgtgctgatc   2100
ttcctgagca ccgctgtgtc cgcttgataa                                    2130

SEQ ID NO: 11          moltype = AA  length = 708
FEATURE                Location/Qualifiers
REGION                 1..708
                       note = Zika prM-Envelope Brazil Construct protein
source                 1..708
                       mol_type = protein
                       organism = synthetic construct
SEQUENCE: 11
MDWTWILFLV AAATRVHSGA DTSVGIVGLL LTTAMAAEVT RRGSAYYMYL DRNDAGEAIS     60
FPTTLGMNKC YIQIMDLGHM CDATMSYECP MLDEGVEPDD VDCWCNTTST WVVYGTCHHK    120
KGEARRSRRA VTLPSHSTRK LQTRSQTWLE SREYTKHLIR VENWIFRNPG FALAAAAIAW    180
LLGSSTSQKV IYLVMILLIA PAYSIRCIGV SNRDFVEGMS GGTWVDVVLE HGGCVTVMAQ    240
DKPTVDIELV TTTVSNMAEV RSYCYEASIS DMASDSRCPT QGEAYLDKQS DTQYVCKRTL    300
VDRGWGNGCG LFGKGSLVTC AKFACSKKMT GKSIQPENLE YRIMLSVHGS QHSGMIVNDT    360
GHETDENRAK VEITPNSPRA EATLGGFGSL GLDCEPRTGL DFSDLYYLTM NNKHWLVHKE    420
WFHDIPLPWH AGADTGTPHW NNKEALVEFK DAHAKRQTVV VLGSQEGAVH TALAGALEAE    480
MDGAKGRLSS GHLKCRLKMD KLRLKGVSYS LCTAAFTFTK IPAETLHGTV TVEVQYAGTD    540
GPCKVPAQMA VDMQTLTPVG RLITANPVIT ESTENSKMML ELDPPFGDSY IVIGVGEKKI    600
THHWHRSGST IGKAFEATVR GAKRMAVLGD TAWDFGSVGG ALNSLGKGIH QIFGAAFKSL    660
FGGMSWFSQI LIGTLLMWLG LNTKNGSISL MCLALGGVLI FLSTAVSA                708

SEQ ID NO: 12          moltype = AA  length = 18
FEATURE                Location/Qualifiers
REGION                 1..18
                       note = IgE Leader
```

```
source                    1..18
                          mol_type = protein
                          organism = synthetic construct
SEQUENCE: 12
MDWTWILFLV AAATRVHS                                                      18

SEQ ID NO: 13             moltype = DNA  length = 1119
FEATURE                   Location/Qualifiers
misc_feature              1..1119
                          note = Zika NS1 DNA (pGX7211)
source                    1..1119
                          mol_type = other DNA
                          organism = synthetic construct
SEQUENCE: 13
atggactgga cctggattct gttcctggtg gcagcagcaa cacgggtgca ctccgtgggc    60
tgctctgtgg atttcagcaa gaaggagaca agatgtggca caggcgtgtt cgtgtacaac   120
gacgtggagg cctggaggga tcgctacaag tatcaccctg actctccacg agactggca    180
gcagcagtga agcaggcatg ggaggagggc atctgcggca tcagctccgt gtcccggatg   240
gagaatatca tgtggaagtc tgtggagggc gagctgaacg ccatcctgga ggagaatgga   300
gtgcagctga ccgtggtggt gggcagcgtg aagaacccaa tgtggagggg accacagaga   360
ctgccagtgc cagtgaatga gctgccacac ggatggaagg catggggcaa gtcttatttc   420
gtgagggccg ccaagaccaa caatagcttt gtggtggacg gcgatacact gaaggagtgc   480
cccctgaagc accgcgcctg gaactccttt ctggtggagg atcacggctt cggcgtgttt   540
cacaccagcg tgtggctgaa ggtgagggag gactactccc tggagtgtga tcctgccgtg   600
atcggaacag cagtgaaggg caaggaggca gcacactctg acctgggcta ttggatcgag   660
agcgagaaga cgatacctg gaggctgaag cgcgcccact tgatcgagat gaagacctgt   720
gagtggccaa agtcccacac cctgtggaca gacggcgtgg aggagtctga tctgatcatc   780
cctaagagcc tggccggccc actgtcccac acaataccag ggagggcta ccgcacacag   840
gtgaagggcc cctggcactc cgaggagctg agatccgct tcgaggagtg ccctggcacc   900
aaggtgcacg tggaggagac atgtggcaca cggggcccct ctctgagaag caccacagcc   960
agcggcagag tgatcgagga tggtgctgt cgcgagtgca caatgccccc tctgtccttt  1020
cgggccaagg acggctgttg gtatggcatg gagatccggc ccagaaagga gcctgagtcc  1080
aatctggtga gatctatggt gaccgccggc agctgataa                         1119

SEQ ID NO: 14             moltype = DNA  length = 435
FEATURE                   Location/Qualifiers
misc_feature              1..435
                          note = Zika Capsid DNA (pGX7212)
source                    1..435
                          mol_type = other DNA
                          organism = synthetic construct
SEQUENCE: 14
atggactgga cctggattct gttcctggtg gcagcagcaa cacgggtgca cagcaagaac    60
cccaagaaga agagcggcgg cttccggatc gtgaacatgc tgaagcgggg cgtggccaga   120
gtgaatccac tggcggcgg cctgaagcgg ctgcctgcag gctgctgct gggccacggc    180
ccaatcagga tggtgctggc catcctggcc ttcctgcgct ttaccgccat caagccctct   240
ctgggcctga tcaacagatg gggcagcgtg ggcaagaagg aggccatgga gatcatcaag   300
aagttcaaga aggacctggc cgccatgctg cgcatcatca tgcaaggaa ggagaggaag   360
aggagaggcg ccgatacaag catcggcatc atcggcctgc tgctgaccac agcaatggca   420
gccgagatct gataa                                                    435

SEQ ID NO: 15             moltype = DNA  length = 2130
FEATURE                   Location/Qualifiers
misc_feature              1..2130
                          note = Zika Pre+Env (Brazil) (pGX7213)
source                    1..2130
                          mol_type = other DNA
                          organism = synthetic construct
SEQUENCE: 15
atggactgga cctggattct gttcctggtg gcagcagcaa cacgggtgca cagcggagca    60
gataccteg tgggaatcgt gggcctgctg ctgaccacag caatggcagc agaggtgacc   120
aggagaggct ctgcctacta tgtgtacctg gacagaaatg atgccggcga ggccatcagc   180
ttccccacca cactgggcat gaacaagtgc tacatccaga tcatggacct gggccacatg   240
tgcgatgcca ccatgagcta tgagtgtcca atgctggacg agggcgtgga gcccgacgtg   300
gtggattgct ggtgtaatac cacatcccac tgggtggtgt acggcacctg tcaccacaag   360
aagggagagg caaggcgctc tcggagagca gtgacactgc cttccactc tacccggaag   420
ctgcagacaa gatctcagac ctggctggag agcggggagt atacaaagca cctgatccgg   480
gtggagaact ggatctttag aaatccagga ttcgcactgg cagcagcagc aatcgcctgg   540
ctgctgggca gctccacctc tcagaaagtg atctacctgg tcatgatcct gctgatcgcc   600
cctgcctatt ccatcaggtg catcggcgtg tctaatcgcg actttgtgga gggaatgtcc   660
ggcggcacct ggtggatgt ggtgctggag acgcggat gcgtgacagt gatggccag    720
gacaagccaa ccgtggatat cgagctggtg accacaaccg tgagcaacat ggccgaggtg   780
cggtcctact gctatgaggc cagcatctcc gacatggcct ctgatagcag atgtcccacc   840
caggggagag tcacctgga caagcagaac gatacacagt acgtgtgaa gaggaccgtg   900
gtggacaggg gatggggaaa tggatgtggc ctgtttggca agggctcct ggtgacatgc   960
gccaagttcg cctgttctaa gaagatgacc ggcaagagca tccagccaga gaacctggag  1020
taccggatca tgctgagcgt gcacggctcc cagcactctg catgatcgt gaacgacaca  1080
ggccacgaga cagatgagaa tagggccaag gtggagatca cacctaacag cccacgcgcc  1140
gaggccaccc tgggcgggctt tggctccctg gcctggact gcgagcctag aacaggcctg  1200
```

-continued gacttctccg atctgtacta tctgaccatg aacaataagc actggctggt gcacaaggag 1260
tggtttcacg acatcccact gccatggcac gcaggagcag atacaggaac cccacactgg 1320
aacaataagg aggccctggt ggagttcaag gatgcccacg ccaagaggca gacagtggtg 1380
gtgctgggca gccaggaggg agcagtgcac accgccctgg caggcgccct ggaggccgag 1440
atggacggag caaagggccg cctgtctagc ggccacctga agtgccggct gaagatggat 1500
aagctgagac tgaagggcgt gtcctactct ctgtgcacag ccgccttcac cttcaccaag 1560
atccctgccg agacactgca cggcacagtg accgtggagg tgcagtatgc cggcacagac 1620
ggcccctgta aggtgcctgc ccagatggcc gtggatatgc agacactgac ccctgtgggc 1680
aggctgatca ccgccaatcc agtgatcaca gagtctaccg agaacagcaa gatgatgctg 1740
gagctggacc ctcccttcgg cgacagctat atcgtgatcg gcgtgggcga gaagaagatc 1800
acacaccact ggcaccgcag cggctccaca atcggcaagg cctttgaggc caccgtgagg 1860
ggcgccaaga ggatggccgt gctgggcgac accgcatggg atttcggctc cgtgggcggc 1920
gccctgaact ctctgggcaa gggcatccac cagatcttcg gcgccgcctt taagtccctg 1980
ttcggcggaa tgagctggtt ttcccagatc ctgatcggca cactgctgat gtggctgggc 2040
ctgaacacca agaatggctc tatcagcctg atgtgcctgg ccctgggcgg cgtgctgatc 2100
ttcctgtcca ccgccgtgtc tgcctgataa 2130

SEQ ID NO: 16 moltype = DNA length = 2130
FEATURE Location/Qualifiers
misc_feature 1..2130
note = Zika PreEnv (MR766) (pGX7214)
source 1..2130
mol_type = other DNA
organism = synthetic construct
SEQUENCE: 16
atggactgga cctggattct gttcctggtg gcagcagcaa cacgggtgca ctccggagcc 60
gatacctcta tcggcatcgt gggcctgctg ctgaccacag caatggcagc agagatcacc 120
aggagaggca gcgcctacta tatgtacctg gacagatctg atgccggcaa ggccatcagc 180
ttcgccacca cactgggcgt gaataagtgc cacgtgcaga tcatggacct gggccacatg 240
tgcgatgcca ccatgtccta cgagtgtcca atgctggacg agggcgtgga gcccgacgat 300
gtggattgct ggtgtaacac cacatctaca tgggtggtgt atggcacctg tcaccacaag 360
aagggagagg caaggcgcag ccggagagca gtgacactgc cctctcacag cacccggaag 420
ctgcagacaa gaagccagac ctggctggag tccagggagt ataccaagca cctgatcaag 480
gtggagaact ggatctttcg caatcccggc ttcacactgg tggcagtggc aatcgcatgg 540
ctgctgggca gctccacctc tcagaaagtg atctacctgg tcatgatcct gctgatcgcc 600
cctgcctatt ccatccggtg catcggcgtg tctaatagag actttgtgga gggaatgtcc 660
ggcggcacct gggtggatgt ggtgctggag cacggcggat gcgtgacagt gatggcccag 720
gacaagccaa ccgtggatat cgagctggtg accacaaccg tgagcaacat ggccgaggtg 780
cggtcctact gctatgaggc ctccatctct gacatggcca gcgattccag atgtcccacc 840
cagggcgagg cctacctgga caagcagtcc gatacacagt acgtgtgcaa gaggaccctg 900
gtggacaggg gatggggaaa tggatgtggc ctgtttggca agggctctct ggtgacatgc 960
gccaagttca cctgttctaa gaagatgaca ggcaagagca tccagcccga gaacctggag 1020
taccggatca tgctgagcgt gcacggctct cagcacagcg gcatgatcgt gaacgacgag 1080
ggctatgaga cagatgagaa tcgggccaag gtggaggtga cacctaacag cccaagagcc 1140
gaggccaccc tgggcggctt tggctccctg ggcctggact gcgagcctag gacaggcctg 1200
gacttctccg atctgtacta tctgaccatg aacaataagc actggctggt gcacaaggag 1260
tggtttcacg acatcccact gccatggcac gcaggagcag atacaggaac cccacactgg 1320
aacaataagg aggccctggt ggagttcaag gatgcccacg ccaagaggca gacagtggtg 1380
gtgctgggca gccaggaggg agcagtgcac accgccctgg caggcgccct ggaggccgag 1440
atggacggag caaagggccg cctgttctcc ggccacctga agtgcaggct gaagatggat 1500
aagctgcgcc tgaagggcgt gtcttacagc ctgtgcacag ccgccttcac cttcaccaag 1560
gtgcctgccg agacactgca cggcacagtg accgtggagg tgcagtatgc cggcacagac 1620
ggcccctgta aggtgcctgc ccagatggcc gtggatatgc agacactgac ccctgtgggc 1680
aggctgatca ccgccaatcc agtgatcaca gagagcaccg agaactccaa gatgatgctg 1740
gagctggacc ctcccttcgg cgacagctac atcgtgatcg gcgtgggcga caagaagatc 1800
acacaccact ggcaccgctc cggctctaca atcggcaagg ccttcgaggc caccgtgagg 1860
ggcgccaaga ggatggccgt gctgggcgac accgcatggg attttggctc cgtgggcggc 1920
gtgttcaatt ctctgggcaa gggcatccac cagatcttcg gcgccgcctt taagagcctg 1980
ttcggcggaa tgtcctggtt ttctcagatc ctgatcggca cactgctggt gtggctgggc 2040
ctgaacacaa agaatggcag catctccctg acctgcctgg ccctgggcgg cgtgatgatc 2100
ttcctgtcta ccgccgtgag cgcctgataa 2130

SEQ ID NO: 17 moltype = DNA length = 2070
FEATURE Location/Qualifiers
misc_feature 1..2070
note = Zika PreEnv (MR766) w/out capsid
source 1..2070
mol_type = other DNA
organism = synthetic construct
SEQUENCE: 17
atggactgga cttggattct gttcctggtg gctgccgcta caagagtgca ttcaattacc 60
aggaggggca gcgcctacta catgtacctg gacagaagcg acgccggaaa agccatcagc 120
ttcgccacaa ccctgggcgt caacaagtgc cacgtgcaga tcatggacct gggccacatg 180
tgcgacgcca caatgagcta cgagtgccct atgctggacg agggagtgga accagacgac 240
gtcgactgtt ggtgcaacac cacctccact tgggtcgtgt acggcacttg ccaccacaag 300
aagggcgagg ccagaagaag cagaagagcc gtgaccctgc ctagccacag caccagaaag 360
ctgcagacca ggagccagac ttggctggaa agccgcgagt acaccaagca cctgatcaag 420
gtggagaatt ggatcttccg gaaccccggc ttcacactgg tggccgtggc aatcgcttgg 480
ctgctgggat ctagcaccag ccagaaagtg atctacctgg tcatgatcct gctgatcgcc 540

```
ccagcctaca gcatccgctg tatcggagtg agcaaccggg acttcgtgga gggaatgagc  600
ggaggaactt gggtggacgt ggtgctggaa cacggaggtt gcgtgacagt gatggctcag  660
gacaagccca ccgtggatat cgagctggtg accaccaccg tgtccaacat ggccgaagtg  720
cgcagctact gctacgaggc cagtatctcc gacatggcca gcgatagccg ctgtcctaca  780
cagggagagg cctatctgga caagcagagc gacacccagt acgtctgcaa gaggacctc  840
gtggatagag gctggggaaa cggttgcgga ctgttcggaa agggcagcct cgtgacttgc  900
gccaagttca cttgcagcaa gaagatgacc ggcaagtcta tccagcccga gaacctggag  960
taccggatca tgctgagcgt gcacggaagc cagcacagcg gcatgatcgt gaacgacgag  1020
ggatacgaga ccgacgagaa cagggccaag gtggaagtga cccctaacag ccctagagcc  1080
gaagccacac tgggaggatt tggcagcctg ggactggatt gcgagcctag aacaggcctg  1140
gacttcagcg acctgtacta cctgaccatg aacaacaagc attggctggt gcacaaggag  1200
tggttccacg acatccctct gccttggcac gcaggagccg atacaggcac acctcattgg  1260
aacaacaagg aggccctggt ggagttcaag gacgctcacg ccaagagaca gacagtggtg  1320
gtgctgggaa gccaggaagg agcagtgcat acagccctgg aagcactct ggaagcagaa  1380
atggacggcg ctaagggcag actgttcagc ggacacctca agtgccggct gaagatggac  1440
aagctgcggc tgaagggcgt gtcttacagc ctctgcaccg cagccttcac cttcaccaag  1500
gtgccagcag agacactgca cggaacagtg accgtggaag tgcagtacgc cggaacagac  1560
ggaccttgca aagtgccagc ccagatggca gtggacatgc agacactgac cccagtggga  1620
aggctgatca ccgctaaccc cgtcatcacc gagagcaccg agaacagcaa gatgatgctg  1680
gagctggacc cccccttcgg cgatagctac atcgtgatcg gcgtgggcga caagaagatc  1740
acccaccatt ggcacagaag cggcagcaca atcggcaagg ctttcgaggc caccgtgaga  1800
ggagctaaga aatggccgt gctgggagac accgcttggg attttggcag cgtgggagga  1860
gtgttcaaca gcctgggcaa gggcatccac cagatcttcg gagccgcctt caagagcctg  1920
ttcggcggca tgtcttggtt cagccagatc ctgatcggaa cactcctcgt ctggctggga  1980
ctgaacacca gaacggcag catcagcctg acttgtctgg ccctgggagg cgtgatgatc  2040
ttcctgagca ccgccgtgtc cgcttgataa                                    2070

SEQ ID NO: 18          moltype = AA  length = 688
FEATURE                Location/Qualifiers
REGION                 1..688
                       note = Zika PreEnv (MR766) w/out capsid
source                 1..688
                       mol_type = protein
                       organism = synthetic construct
SEQUENCE: 18
MDWTWILFLV AAATRVHSIT RRGSAYYMYL DRSDAGKAIS FATTLGVNKC HVQIMDLGHM  60
CDATMSYECP MLDEGVEPDD VDCWCNTTST WVVYGTCHHK KGEARRSRRA VTLPSHSTRK  120
LQTRSQTWLE SREYTKHLIK VENWIFRNPG FTLVAVAIAW LLGSSTSQKV IYLVMILLIA  180
PAYSIRCIGV SNRDFVEGMS GGTWVDVVLE HGGCVTVMAQ DKPTVDIELV TTTVSNMAEV  240
RSYCYEASIS DMASDSRCPT QGEAYLDKQS DTQYVCKRTL VDRGWGNGCG LFGKGSLVTC  300
AKFTCSKKMT GKSIQPENLE YRIMLSVHGS QHSGMIVNDE GYETDENRAK VEVTPNSPRA  360
EATLGGFGSL GLDCEPRTGL DFSDLYYLTM NNKHWLVHKE WFHDIPLPWH AGADTGTPHW  420
NNKEALVEFK DAHAKRQTVV VLGSQEGAVH TALAGALEAE MDGAKGRLFS GHLKCRLKMD  480
KLRLKGVSYS LCTAAFTFTK VPAETLHGTV TVEVQYAGTD GPCKVPAQMA VDMQTLTPVG  540
RLITANPVIT ESTENSKMML ELDPPFGDSY IVIGVGDKKI THHWHRSGST IGKAFEATVR  600
GAKRMAVLGD TAWDFGSVGG VFNSLGKGIH QIFGAAFKSL FGGMSWFSQI LIGTLLVWLG  660
LNTKNGSISL TCLALGGVMI FLSTAVSA                                     688

SEQ ID NO: 19          moltype = AA  length = 15
FEATURE                Location/Qualifiers
REGION                 1..15
                       note = prME epitope
source                 1..15
                       mol_type = protein
                       organism = synthetic construct
SEQUENCE: 19
IRCIGVSNRD FVEGM                                                   15
```

VACCINES AGAINST ZIKA VIRUS

CROSS-REFERENCE TO RELATED APPLICATIONS

This application is a Continuation of U.S. National Stage application Ser. No. 16/078,270, filed Aug. 21, 2018, which was filed under 35 U.S.C. § 371 claiming benefit to International Patent Application No. PCT/US2017/019407, filed Feb. 24, 2017, which claims priority to U.S. Provisional Application No. 62/300,030, filed Feb. 25, 2016, U.S. Provisional Application No. 62/305,183, filed Mar. 8, 2016, U.S. Provisional Application No. 62/396,742, filed Sep. 19, 2016, U.S. Provisional Application No. 62/417,100, filed Nov. 3, 2016, and U.S. Provisional Application No. 62/462,249, filed Feb. 22, 2017, each of which is incorporated by reference herein in its entirety.

REFERENCE TO A "SEQUENCE LISTING" SUBMITTED AS AN XML FILE

The Sequence Listing written in the XML file: "206108-0069-01US_SequenceListing.xml"; created on May 15, 2023, and 44,755 bytes in size, is hereby incorporated by reference.

FIELD OF THE INVENTION

The present invention relates to Zika vaccines, improved methods for inducing immune responses, and for prophylactically and/or therapeutically immunizing individuals against Zika virus.

BACKGROUND

Zika virus (ZIKAV) is a small, enveloped, positive-stranded RNA virus that belongs to the Flavivirus genus of the Flaviviridae family. The virus is known to be transmitted by daytime-active *Aedes* mosquitoes, such as *A. aegypti* and *A. albopictus*. Its name comes from the Zika Forest of Uganda, where the virus was first isolated in 1947.

The infection, known as Zika fever, often causes no or only mild symptoms, similar to a mild form of dengue fever. Since the 1950s, it has been known to occur within a narrow equatorial belt from Africa to Asia. The virus spread eastward across the Pacific Ocean between 2013 and 2014 to French Polynesia, New Caledonia, the Cook Islands, and Easter Island, and in 2015 to Mexico, Central America, the Caribbean, and South America, where the Zika outbreak has reached pandemic levels. As of 2016, the illness cannot be prevented by drugs or vaccines. As of February 2016, there is evidence that Zika fever in pregnant women can cause abnormal brain development in their fetuses by mother-to-child transmission, which may result in miscarriage or microcephaly.

The combination of the increasing spread of the virus, globally, and the absence of any treatment or vaccine against the virus causes the Zika virus to be a global health concern.

Therefore, there remains a need to develop a vaccine that provides broad immunity against the Zika virus, and preferably a vaccine that is economical and effective across all serotypes. Further, there remains a need for an effective method of administering vaccines, such as DNA vaccines or DNA plasmid vaccines, to a mammal in order to provide immunization against Zika virus, either prophylatically or therapeutically.

SUMMARY OF THE INVENTION

One aspect of the present invention provides nucleic acid constructs capable of expressing a polypeptide that elicits an immune response in a mammal against Zika virus. The nucleic acid constructs are comprised of an encoding nucleotide sequence and a promoter operably linked to the encoding nucleotide sequence. The encoding nucleotide sequence expresses the polypeptide, wherein the polypeptide includes consensus Zika antigens, including pre-membrane-envelope (prM+Env or prME). The promoter regulates expression of the polypeptide in the mammal.

Another aspect of the present invention provides DNA plasmid vaccines that are capable of generating in a mammal an immune response against a Zika virus. The DNA plasmid vaccines are comprised of a DNA plasmid capable of expressing a consensus Zika antigen in the mammal and a pharmaceutically acceptable excipient. The DNA plasmid is comprised of a promoter operably linked to a coding sequence that encodes the consensus Zika antigen. The consensus Zika antigen is comprised of consensus prME.

Another aspect of the present invention provides methods of eliciting an immune response against Zika virus in a mammal, comprising delivering a DNA plasmid vaccine to tissue of the mammal, the DNA plasmid vaccine comprising a DNA plasmid capable of expressing a consensus antigen of the Zika virus in a cell of the mammal to elicit an immune response in the mammal, and electroporating cells of the tissue to permit entry of the DNA plasmids into the cells.

BRIEF DESCRIPTION OF THE DRAWINGS

FIG. 4 displays an annotated amino acid sequence for a Zika antigen—leader sequence+prME.

FIG. 5 shows genetic distance between isolates, and FIG. 6 displays a genetic tree.

FIG. 9A showing nonspecific binding to anti-sera in the cell lysates; FIG. 9B showing specific binding to anti-pan-flavivirus in the cell lysates.

FIG. 11 of individual mice. FIG. 12 group averages. Mean responses in each group one week after the third immunization.

FIG. 15A through FIG. 15E display an analysis indicating that ZV-prME vaccine generated sera does not cross-react with Dengue 1-4 recombinant Envs. Analysis supports that anti-CHIKV vaccine induced sera does not bind to Zika Env, also.

FIG. 16A through FIG. 16E depict experimental results demonstrating construction of the ZV-prME consensus DNA vaccine. FIG. 16A depicts the phylogenetic tree at the amino acid level of the ZIKV envelope sequence between ZIKV isolates and envelope strains. A consensus design strategy was adopted for the ZIKV-prME consensus sequence. Scale bars signify the distance of amino acids per site. Analyses were conducted using the MEGA version 5 software. Red star denotes the ZIKA-prME consensus. FIG. 16B depicts a diagrammatic representation of the ZIKV-prME DNA vaccine indicating the cloning of prME (prM+Env) into the pVax1 mammalian expression vector, pGX0001. Codon-optimized synthetic genes of prME construct included the IgE leader sequence. The overall gene construct was inserted into the BamH1 and Xho1 sites of the pVax1 vector under the control of the CMV promoter. FIG. 16C depicts an agarose gel electrophoresis analysis of the ZIKV-prME DNA vaccine. Lane 1 shows the undigested vaccine construct; Lane 2, restriction digestion of the plasmid with BamH1/Xho1; Lane 3, DNA molecular size markers (in kb). FIG. 16D depicts expression analysis by SDS-PAGE of ZIKV prME protein expression in 293T cells using western blot evaluation and IFA detection. 293T cells were transfected with the ZIKV-prME plasmid and cell lysates and supernatants were analyzed for expression. Lane 1 contains the protein molecular weight markers (kDa); Lane 2, pVax1 control cell lysate; Lane 3, cell lysate from ZV prME transfected cells; Lane 4, supernatant from ZIKV-prME transfected cells; Lane 5, recombinant prME positive control. FIG. 16E depicts immunofluorescence analysis assay (IFA) assay for ZIKV-prME protein expression in 293T cells. 293T cells were transfected with 5 μg of the ZIKV-prME plasmid. Twenty-four hours post transfection immunofluorescence labeling was performed with sera (1:100) from immunized mice and anti-mouse IgG FITC. Staining with sera from ZIKV-prME and pVax1 immunized mice is shown.

FIG. 17A through FIG. 17C depict experimental results demonstrating the characterization of cellular immune responses in mice following vaccination with the ZIKV-prME DNA vaccine. FIG. 17A depicts ELISpot analysis measuring IFN-γ secretion in splenocytes. C57/BL6 mice (n=5/group) were immunized intramuscularly three times with 25 μg of either pVax1 or the ZIKV-prME DNA vaccine followed by in vivo EP. IFN-γ generation, as an indication of cellular immune response induction, was measured by IFN-γ ELISPOT. Splenocytes harvested 7 days after the third immunization were incubated in the presence of one of six peptide pools spanning the entire prM and envelope proteins. Results are shown in stacked bar graphs. The data represent the average numbers of SFU (spot forming units) per million splenocytes with values representing the mean responses in each group (n=4)±SEM. FIG. 17B depicts the epitope composition of the ZIKV-prME-specific IFN-γ response as determined by stimulation with matrix peptide pools one week after the third immunization. Values represent mean responses in each group (n=4)±SEM. Experiments were performed independently at least three times with similar results. FIG. 17C depicts immunization with ZIKV-prME induces higher number of IFN-γ and TNF-α secreting cells when stimulated by ZIKV peptides. One week after the last immunization with the ZIKV-prME vaccine, splenocytes were cultured in the presence of pooled ZIKV peptides (5 μM) or tissue culture medium only. Frequencies of ZIKV peptide-specific IFN-γ and TNF-α secreting cells were measured by fluorescence-activated cell sorting (FACS) assay. Single function gates were set based on negative control (unstimulated) samples and were placed consistently across samples. The percentage of the total CD8+ T cell responses are shown. These data are representative of two independent immunization experiments.

FIG. 18A through FIG. 18D depict the profile of IFN-γ production by splenocytes and antibody levels in serum collected from pZIKV-prME (MR766) and pZIKV-prME (Brazil)-immunized mice. Six week-old C57/BL6 mice were immunized as described in Materials and Methods. Serum and splenocytes were collected one week after the 3rd immunization and incubated with ZIKV-specific prME peptides, and the number of IFN-γ SFU per million cells was assayed by ELISPOT. FIG. 18A depicts ELISpot analysis of serum collected from MR766-immunized mice. FIG. 18B depicts ELISpot analysis of serum collected from Brazil-immunized mice. Anti-ZIKV Env antibody levels in the serum were measured by ELISA (C&D). FIG. 18C depicts Anti-ZIKV Env antibody levels in the serum measured by ELISA in MR766-immunized mice. FIG. 18D depicts Anti-ZIKV Env antibody levels in the serum measured by ELISA in Brazil-immunized mice.

FIG. 19A through FIG. 19E depict experimental results demonstrating anti-ZIKV antibody responses are induced by ZIKV-prME plasmid vaccination. C57BL/6 mice were immunized intramuscularly three times with 25 μg of ZIKV-prME plasmid or pVax1 at 2-week intervals. Binding to envelope antigen was analyzed with sera from animals at different time points post immunization at various dilutions. ELISA plates were coated with vaccine matched recombinant ZIKV-envelope protein FIG. 19A depicts results from 1 of 2 independent experiments are presented. Similar results were obtained in the second experiment. FIG. 19B depicts the differences in the anti-ZIKV endpoint titers produced in response to the ZIKV-prME immunogen were analyzed in sera from immunized animals after each boost. FIG. 19C depicts western blot analysis of ZIKV-envelope antigen expression. The recombinant ZIKV-Env protein at various concentration were electrophoresed on a 12.5% SDS polyacrylamide gel and analyzed by Western blot analysis with sera from pVax1 or ZIKV-prME immunized mice, as indicated. Expression of the ZIKV-Env protein is indicated by the arrowheads. FIG. 19D depicts an immunofluorescence analysis of Vero cells infected with either ZIKV-MR766 or mock infected following incubation with sera from ZIKV-prME or pVax1 immunized mice. FIG. 19E: Serum samples from the pZIKV-prME immunized mice were tested by plaque-reduction neutralization (PRNT) assay for their ability to neutralize ZIKV infectivity in vitro. PRNT50 was defined as the serum dilution factor that could inhibit 50% of the input virus. Values in parentheses indicate the PRNT50. Control plasmid pZIKV-Capsid and pVax1 sera were used as negative controls.

FIG. 20A through FIG. 20E depict experimental results demonstrating induction of ZIKV specific cellular immune responses following ZIKV=prME DNA vaccination of NHPs. FIG. 20A depicts rhesus macaques were immunized intradermally (ID) with 2 mg of ZIKV-prME plasmid at weeks 0 and 4 administered as 1 mg at each of two sites, with immunization immediately followed by intradermal EP. PBMCs were isolated pre-immunization and at week 6 and were used for the ELISPOT assay to detect IFN-γ-secreting cells in response to stimulation with ZIKV-prME peptides. The number of IFN-γ producing cells obtained per million PBMCs against six peptide pools encompassing the entire prME protein is indicated on the y-axis for the vaccination groups. Values represent mean responses in each group (n=5)±SEM. FIG. 20B depicts the detection of ZIKV-prME-specific antibody responses following DNA vaccination. Anti-ZIKV IgG antibodies were measured pre-immunization and at week 6 by ELISA. FIG. 20C depicts end-point ELISA titers for anti ZIKV-envelope antibodies are shown following the first and second immunizations. FIG. 20D depicts western blot analysis using week 6 pooled monkey sera demonstrated binding to recombinant envelope protein. FIG. 20E depicts immunofluorescence analysis of Vero cells infected with ZIKV MR766 at 10 PFU. Cells were probed 24 hrs following infection with wk 6 pooled monkey sera at 1:100 and then detected with secondary anti-human IgG-AF488.

FIG. 21A through FIG. 21C depict experimental results demonstrating plaque-reduction neutralization activity of serum from Rhesus Macaques immunized with ZIKV-prME. Rhesus Macaques were immunized as described in Materials and Methods. FIG. 21A depicts pre immunization and week 6 immune sera from individual monkeys were tested by plaque reduction neutralization (PRNT) assay for their ability to neutralize ZIKV infectivity in vitro. PRNT50 was defined as the serum dilution factor that could inhibit 50% of the input virus. Calculated IC50 values are listed for each monkey. FIG. 21B and FIG. 21C depict the cytopathic effect of ZIKV MR766 and PR209 in Vero, SK-N-SH, and U87MG cells. FIG. 21B depicts Vero cells were mock infected or infected with the MR766 or PR209 viruses. FIG. 21C depicts SK-N-SH and U87MG cells were mock or infected with MR766 at an MOI of 0.001 PFU/cell in the presence of pooled NHP sera immunized with ZIKV-prME vaccine (Wk 6). The induction of syncytium formation (CPE) and prME protein expression were analyzed 48 hours post infection by indirect immunofluorescence assay (IFA) using the immunized NHP sera. Pictures were taken at 4× objective.

FIG. 22A through FIG. 22C depict experimental results demonstrating Profile of IFN-γ and antibody production by spleen cells isolated from pZIKV-prME in mice lacking the type I interferon α, β receptor. FIG. 22A depicts IFN α, β receptor knockout mice (four to six) were immunized intramuscularly three times with 25 µg of pZIKV-prME or pVax1 plasmid at 2-week intervals. Splenocytes were collected two weeks after the last immunization and incubated with prME peptides and the number of IFN-γ-producing cells were measured by ELISPOT. FIG. 22B depicts serum antibody specific for ZIKV Env protein in immunized animals was measured by ELISA at various days post immunization. FIG. 22C depicts the endpoint titer 0, 1, 2, 3, 4 and 5 weeks after immunization.

FIG. 23A through FIG. 23F depict experimental results demonstrating survival data for immunized mice lacking the type I interferon α, β receptor following Zika virus infection. Survival of IFN-α/β receptor knockout mice after Zika infection. FIG. 23A depicts mice were immunized once and challenged with 106 PFU of ZIKV-PR209, 2 weeks later. FIG. 23B depicts mice were immunized twice at 2 week intervals and challenged with 106 PFU of ZIKV-PR209 7 days after the second immunization. FIG. 23C depicts mice were immunized twice at 2 week intervals and challenged with 2×106 PFU of ZIKV PR209, 7 days after the second immunization. The survival curves were constructed using data from two separate experiments. FIG. 23D depicts weight change for animals immunized 2× is depicted; the data reflect the results from two independent experiments with 10 to 15 mice per group per experiment. FIG. 23E depicts clinical scores for animals in FIG. 23B. FIG. 23F depicts clinical scores for animals in FIG. 23C. The designation for the clinical scores is as follows: 1—no disease, 2—decreased mobility; 3—hunched posture and decreased mobility; 4—hindlimb knuckle walking (partial paralysis), 5—paralysis of one hind limb and 6—paralysis of both hind limbs.

FIG. 24A through FIG. 24E depict experimental results demonstrating the construction of the ZIKV-prME consensus DNA vaccine. FIG. 24A depicts a diagrammatic representation of the ZIKV-prME DNA vaccine indicating the cloning of rME into the pVax1 mammalian expression vector. A consensus design strategy was adopted for the ZIKV-prME consensus sequence. Codon-optimized synthetic genes of the prME construct included a synthetic IgE leader sequence. The optimized gene construct was inserted into the BamH1 and Xho1 sites of a modified pVax1 vector under the control of the CMV promoter. FIG. 24B depicts a model building of the ZIKV-E proteins demonstrates overlap of the vaccine target with potentially relevant epitope regions. Several changes made for vaccine design purpose are located in domains II and III (located within dashed lines of inset, middle left). Vaccine-specific residue changes in these regions are shown in violet CPK format on a ribbon backbone representation of an E (envelope) protein dimer (each chain in light and dark green, respectively). Regions corresponding to the defined EDE are indicated in cyan, and the fusion loop is indicated in blue. Residue Ile156 (T156I) of the vaccine E protein, modelled as exposed on the surface of the 150 loop, is part of an N-linked glycosylation motif NXS/T in several other ZIKV strains as well as in multiple dengue virus strains. FIG. 24C depicts expression analysis by SDS-PAGE of ZIKV-prME protein expression in 293T cells using western blot analysis. The 293T cells were transfected with the ZIKV-prME plasmid and the cell lysates and supernatants were analyzed for expression of the vaccine construct with pan-flavivirus immunized sera. Protein molecular weight markers (kDa); cell lysate and supernatant from ZIKV-prME transfected cells and rZIKV-E positive control were loaded as indicated. FIG. 24D depicts expression analysis by SDS-PAGE of ZIKV-prME protein expression in 293T cells using western blot analysis. The 293T cells were transfected with the ZIKV-prME plasmid and the cell lysates and supernatants were analyzed for expression of the vaccine construct with ZIKV-prME immunized sera. Protein molecular weight markers (kDa); cell lysate and supernatant from ZIKV-prME transfected cells and rZIKV-E positive control were loaded as indicated. FIG. 24E depicts Immunofluorescence assay (IFA) analysis for ZIKV-prME protein expression in 293T cells. The cells were transfected with 5 μg of the ZIKVprME plasmid. Twenty-four hours post transfection, immunofluorescence labelling was performed with the addition of sera (1:100) from ZIKV-prME immunized mice followed by the addition of the secondary anti-mouse IgG-AF488 antibody for detection. Staining with sera from ZIKV-prME and pVax1 immunized mice is shown. DAPI panels show control staining of cell nuclei. Overlay panels are combinations of antimouse IgG-AF488 and DAPI staining patterns. DAPI, 4',6-diamidino-2-phenylindole; ZIKV-prME, precursor membrane and envelope of Zika virus.

FIG. 25A through FIG. 25D depict experimental results demonstrating the characterization of cellular immune responses in mice following vaccination with the ZIKV-prME DNA vaccine. FIG. 25A depicts a timeline of vaccine immunizations and immune analysis used in the study. FIG. 25B depicts ELISpot analysis measuring IFN-γ secretion in splenocytes in response to ZIKV-prME immunization. C57BL/6 mice (n=4/group) were immunized i.m. three times with 25 μg of either pVax1 or the ZIKV-prME DNA vaccine followed by electroporation. IFN-γ generation, as an indication of induction of cellular immune responses, was measured by an IFN-γ ELISpot assay. The splenocytes harvested 1 week after the third immunization were incubated in the presence of one of the six peptide pools spanning the entire prM and Envelope proteins. Results are shown in stacked bar graphs. The data represent the average numbers of SFU (spot-forming units) per million splenocytes with values representing the mean responses in each±s.e.m. FIG. 25C depicts the epitope composition of the ZIKVprME-specific IFN-γ response as determined by stimulation with matrix peptide pools 1 week after the third immunization. The values represent mean responses in each group±s.e.m. The experiments were performed independently at least three times with similar results. FIG. 25D depicts flow cytometric analysis of T-cell responses. Immunisation with ZIKV-prME induces higher number of IFN-γ and TNF-α secreting cells when stimulated by ZIKV peptides. One week after the last immunization with the ZIKV-prME vaccine, splenocytes were cultured in the presence of pooled ZIKV peptides (5 μM) or R10 only. Frequencies of ZIKV peptide-specific IFN-γ and TNF-α secreting cells were measured by flow cytometry. Single function gates were set based on negative control (unstimulated) samples and were placed consistently across samples. The percentage of the total CD8$^+$ T-cell responses are shown. These data are representative of two independent immunization experiments. IFN, interferon; TNF, tumour necrosis factor; ZIKV-prME, precursor membrane and envelope of Zika virus.

FIG. 26A through FIG. 26E depict experimental results demonstrating that anti-ZIKV antibody responses are induced by ZIKV-prME vaccination. FIG. 26A depicts ELISA analysis measuring binding antibody production (measured by OD450 values) in immunized mice. The C57BL/6 mice (n=4) were immunized i.m. three times with 25 μg of ZIKV-prME plasmid or pVax1 at 2-week intervals. Binding to rZIKV-E was analyzed with sera from animals at different time points (days 21, 35 and 50) post immunization at various dilutions. The data shown are representative of at least three separate experiments. FIG. 26B depicts End point binding titer analysis. Differences in the anti-ZIKV end point titers produced in response to the ZIKV-prME immunogen were analyzed in sera from immunized animals after each boost. FIG. 26C depicts Western blot analysis of rZIKV-E specific antibodies induced by ZIKV-prME immunization. The rZIKV-E protein was electrophoresed on a 12.5% SDS polyacrylamide gel and analyzed by western blot analysis with pooled sera from ZIKV-prME immunized mice (day 35). Binding to rZIKV-E is indicated by the arrowhead. FIG. 26D depicts immunofluorescence analysis of ZIKV specific antibodies induced by ZIKV-prME immunization. The Vero cells infected with either ZIKV-MR766 or mock infected were stained with pooled sera from ZIKV-prME immunized mice (day 35) followed by an anti-mouse-AF488 secondary antibody for detection. FIG. 26E depicts plaque-reduction neutralization (PRNT) assay analysis of neutralizing antibodies induced by ZIKV-prME immunization. The serum samples from the ZIKV-prME immunized mice were tested for their ability to neutralize ZIKV infectivity in vitro. PRNT50 was defined as the serum dilution factor that could inhibit 50% of the input virus. The values in parentheses indicate the PRNT50. Control ZIKV-Cap (DNA vaccine expressing the ZIKV capsid protein) and pVax1 sera were used as negative controls. ZIKV-prME, precursor membrane and envelope of Zika virus.

FIG. 27A through FIG. 27E depict experimental results demonstrating Induction of ZIKV specific cellular immune responses following ZIKV-prME vaccination of non-human primates (NHPs). FIG. 27A depicts ELISpot analysis measuring IFN-γ secretion in peripheral blood mononuclear cells (PBMCs) in response to ZIKV-prME immunization. Rhesus macaques were immunized intradermally with 2 mg of ZIKV-prME plasmid at weeks 0 and 4 administered as 1 mg at each of two sites, with immunization immediately followed by intradermal electroporation. PBMCs were isolated pre-immunization and at week 6 and were used for the ELISPOT assay to detect IFN-γ-secreting cells in response to stimulation with ZIKV-prME peptides as described in the 'Materials and Methods' section. The number of IFN-γ producing cells obtained per million PBMCs against six peptide pools encompassing the entire prME protein is shown. The values represent mean responses in each group (n=5)±s.e.m. FIG. 27B depicts the detection of ZIKV-prME-specific antibody responses following DNA vaccination. Anti-ZIKV IgG antibodies were measured pre-immunization and at week 6 by ELISA. FIG. 27C depicts end point ELISA titers for anti ZIKV-envelope antibodies are shown following the first and second immunizations. FIG. 27D depicts western blot analysis using week 6 RM immune sera demonstrated binding to recombinant envelope protein. FIG. 27E depicts PRNT activity of serum from RM immunized with ZIKV-prME. Pre-immunization and week 6 immune sera from individual monkeys were tested by plaque-reduction neutralization (PRNT) assay for their ability to neutralize ZIKV infectivity in vitro. PRNT50 was defined as the serum dilution factor that could inhibit 50% of the input virus. Calculated (PRNT50) values are listed for each monkey. IFN, interferon; ZIKV-prME, precursor membrane and envelope of Zika virus.

FIG. 28A through FIG. 28F depict experimental results demonstrating survival data for immunized mice lacking the type I interferon α, β receptor following ZIKV infection. FIG. 28A depicts survival of IFNAR$^{-/-}$ mice after ZIKV infection. Mice were immunized twice with 25 μg of the ZIKV-prME DNA vaccine at 2-week intervals and challenged with ZIKV-PR209 virus 1 week after the second immunization with 1×10$^6$ plaque-forming units FIG. 28B depicts survival of IFNAR$^{-/-}$ mice after ZIKV infection. Mice were immunized twice with 25 μg of the ZIKV-prME DNA vaccine at 2-week intervals and challenged with ZIKV-PR209 virus 1 week after the second immunization with 2×10$^6$ plaque-forming units FIG. 28C depicts the weight change of animals immunized with 1×10$^6$ plaque-forming units. FIG. 28D depicts the weight change of animals immunized with 2×10$^6$ plaque-forming units. FIG. 28E depicts the clinical scores of animals immunized with 1×10$^6$ plaque-forming units. FIG. 28F depicts the clinical scores of animals immunized with 2×10$^6$ plaque-forming units. The designation for the clinical scores is as follows: 1: no disease, 2: decreased mobility; 3: hunched posture and decreased mobility; 4: hind limb knuckle walking (partial paralysis); 5: paralysis of one hind limb; and 6: paralysis of both hind limbs. The data reflect the results from two independent experiments with 10 mice per group per experiment. ZIKV-prME, precursor membrane and envelope of Zika virus.

FIG. 29A through FIG. 29D depict experimental results demonstrating single immunization with the ZIKV-prME vaccine provided protection against ZIKV challenge in mice lacking the type I interferon α, β receptor. The mice were immunized once and challenged with $2\times10^6$ plaque-forming units of ZIKV-PR209, 2 weeks after the single immunization. The survival curves depict 10 mice per group per experiment. FIG. 29A demonstrates that the ZIKV-prME vaccine prevented ZIKA-induced neurological abnormalities in the mouse brain. FIG. 29B depicts brain sections from pVax1 and ZIKV-prME vaccinated groups were collected 7-8 days after challenge and stained with H&E (haematoxylin and eosin) for histology. The sections taken from representative, unprotected pVax1 control animals shows pathology. (i): nuclear fragments within neuropils of the cerebral cortex (inset shows higher magnification and arrows to highlight nuclear fragments); (ii): perivascular cuffing of vessels within the cortex, lymphocyte infiltration and degenerating cells; (iii): perivascular cuffing, cellular degeneration and nuclear fragments within the cerebral cortex; and (iv): degenerating neurons within the hippocampus (arrows). An example of normal tissue from ZIKV-prME vaccinated mice appeared to be within normal limits (v and vi). FIG. 29C depicts levels of ZIKV RNA in the plasma samples from mice following vaccination and viral challenge at the indicated day post infection. The results are indicated as the genome equivalents per milliliter of plasma. FIG. 29D depicts levels of ZIKV-RNA in the brain tissues were analyzed at day 28 post infection. The results are indicated as the genome equivalent per gram of tissue. ZIKV-prME, precursor membrane and envelope of Zika virus.

FIG. 30A and FIG. 30B depict experimental results demonstrating protection of mice lacking the type I interferon α, β receptor following passive transfer of anti-ZIKV immune sera following ZIKV challenge. Pooled NHP anti-ZIKV immune sera, titred for anti-ZIKA virus IgG, was administered i.p. (150 μl/mouse) to mice 1 day after s.c. challenge with a ZIKA virus ($10^6$ plaque-forming units per mouse). As a control, normal monkey sera and phosphate-buffered saline (PBS) were administered (150 μl/mouse) to age-matched mice as controls. FIG. 30A depicts the mouse weight change during the course of infection and treatment. Each point represents the mean and standard error of the calculated percent pre-challenge (day 0) weight for each mouse. FIG. 30B depicts the survival of mice following administration of the NHP immune sera. ZIKV-prME, precursor membrane and envelope of Zika virus.

FIG. 31A through FIG. 31D depict experimental results demonstrating the characterization of immune responses of ZIKV-prME-MR766 or ZIKV-prME Brazil vaccine in C57BL/6 mice. FIG. 31A depicts ELISpot and ELISA analysis measuring cellular and antibody responses after vaccination with either ZIKV-prME-MR766 and ZIKV-prME-Brazil DNA vaccines. C57BL/6 mice (n=4/group) were immunized intramuscularly three times with 25 μg of ZIKV-prME-MR766 followed by in vivo EP. IFN-γ generation, as an indication of cellular immune response induction, was measured by IFN-γ ELISpot. Splenocytes harvested one week after the third immunization were incubated in the presence of one of six peptide pools spanning the entire prM and E proteins. Results are shown in stacked bar graphs. The data represent the average numbers of SFU (spot forming units) per million splenocytes with values representing the mean responses in each ±SEM. FIG. 31B depicts ELISpot and ELISA analysis measuring cellular and antibody responses after vaccination with either ZIKV-prME-MR766 and ZIKV-prME-Brazil DNA vaccines. C57BL/6 mice (n=4/group) were immunized intramuscularly three times with 25 μg of ZIKV prME-Brazil followed by in vivo EP. IFN-γ generation, as an indication of cellular immune response induction, was measured by IFN-γ ELISpot. Splenocytes harvested one week after the third immunization were incubated in the presence of one of six peptide pools spanning the entire prM and E proteins. Results are shown in stacked bar graphs. The data represent the average numbers of SFU (spot forming units) per million splenocytes with values representing the mean responses in each ±SEM. FIG. 31C depicts ELISA analysis measuring binding antibody production in immunized C57BL/6 mice. Binding to rZIKV-E was analyzed with sera from mice at day 35 post immunization at various dilutions. FIG. 31D depicts ELISA analysis measuring binding antibody production in immunized C57BL/6 mice. Binding to rZIKV-E was analyzed with sera from mice at day 35 post immunization at various dilutions.

FIG. 32A through FIG. 32D depict experimental results demonstrating the expression, purification, and characterization of ZIKV-Envelope protein. FIG. 32A depicts the cloning plasmid for rZIKV E expression. FIG. 32B depicts the characterization of the recombinant ZIKV-E (rZIKV-E) protein by SDS-PAGE and Western blot analysis. Lane 1—BSA control; Lane 2—lysates from *E. coli* cultures transformed with pET-28a vector plasmid, was purified by nickel metal affinity resin columns and separated by SDS-PAGE after IPTG induction. Lane 3, 37 recombinant ZV-E purified protein was analyzed by Western blot with anti-His tag antibody. Lane M, Protein molecular weight marker. FIG. 32C depicts the purified rZIKV-E protein was evaluated for its antigenicity. ELISA plates were coated with rZIKV-E and then incubated with various dilutions of immune sera from the mice immunized with ZIKV-prME vaccine or Pan-flavivirus antibody as positive control. Bound IgG was detected by the addition of peroxidase-conjugated anti-mouse antibody followed by tetramethylbenzidine substrate as described in Experimental Example. FIG. 32D depicts western blot detection of purified rZIKV-E protein with immune sera from ZIKV prME immunized mice. Various concentrations of purified rZIKV-E protein were loaded onto an SDS-PAGE gel as described. A dilution of 1:100 immune sera, and goat anti-mouse at 1:15,000 were used for 1 hour at room temperature. After washing, the membranes were imaged on the Odyssey infrared imager. Odyssey protein molecular weight standards were used. The arrows indicate the position of rZIKV-E protein.

FIG. 33A through FIG. 33C depict experimental results demonstrating the characterization of immune responses ZIKA-prME in IFNAR$^{-/-}$ mice. ELISpot and ELISA analysis measuring cellular and antibody responses to ZIKV-prME in IFNAR$^{-/-}$ mice. Mice (n=4/group) were immunized intramuscularly three times with 25 μg of ZIKV-prME followed by in vivo EP. FIG. 33A depicts IFN-γ generation, as an indication of cellular immune response induction, was measured by IFN-γ ELISPOT. FIG. 33B depicts ELISA analysis measuring binding antibody production in immunized IFNAR$^{-/-}$ mice. Binding to rZIKV-E was analyzed with sera from mice at various time points post immunization. FIG. 33C depicts endpoint titer analysis of anti-ZIKV antibodies produced in immunized IFNAR$^{-/-}$ mice.

FIG. 34A through FIG. 34D depict experimental results demonstrating the neutralization activity of immune sera from Rhesus Macaques immunized against ZIKV-prME. SK-N-SH and U87MG cells were mock infected or infected with MR766 at an MOT of 0.01 PFU/cell in the presence of pooled NHP sera immunized with ZIKV-prME vaccine (Wk 6). Zika viral infectivity were analyzed 4 days post infection by indirect immunofluorescence assay (IFA) using sera from ZIKV-prME vaccinated NHPs. FIG. 34A depicts photographs of stained tissue sample slices taken with a 20× objective demonstrating inhibition of infection by ZIKV viruses MR766 and PR209 in Vero, SK-N-SH and U87MG. FIG. 34B depicts photographs of stained tissue sample slices taken with a 20× objective demonstrating inhibition of infection by ZIKV viruses SK-N-SH and U87MG in Vero, SK-N-SH and U87MG. FIG. 34C depicts a bar graph shows the percentage of infected (GFP positive cells) demonstrating the inhibition of infection by ZIKV viruses MR766 and PR209 in Vero, SK-N-SH and U87MG. FIG. 34D depicts a bar graph showing the percentage of infected (GFP positive cells) demonstrating the inhibition of infection by ZIKV viruses SK-N-SH and U87MG in Vero, SK-N-SH and U87MG FIG. 35A through FIG. 35E depict experimental results demonstrating ZIKV is virulent to IFNAR$^{-/-}$ mice. These data confirm that ZIKV is virulent in IFNAR$^{-/-}$ resulting in morbidity and mortality. FIG. 35A depicts Kaplan-Meier survival curves of IFNAR$^{-/-}$ mice inoculated via intracranial with $10^6$ pfu ZIKV-PR209 virus. FIG. 35B depicts Kaplan-Meier survival curves of IFNAR$^{-/-}$ mice inoculated via intravenously with $10^6$ pfu ZIKV-PR209 virus. FIG. 35C depicts Kaplan-Meier survival curves of IFNAR$^{-/-}$ mice inoculated via intraperitoneal with $10^6$ pfu ZIKV-PR209 virus. FIG. 35D depicts Kaplan-Meier survival curves of IFNAR$^{-/-}$ mice inoculated via subcutaneously with $10^6$ pfu ZIKV-PR209 virus. FIG. 35E depicts the mouse weight change during the course of infection for all the routes.

FIG. 36A through FIG. 36C depict experimental results demonstrating the induction of ZIKV specific cellular immune responses following ZIKV-prME vaccination of Non-Human Primates (NHPs). FIG. 36A is a schematic representation of NHP immunization study. FIG. 36B depicts results after a single immunization. FIG. 36C depicts results after two immunizations. ELISpot analysis measuring IFN-g secretion in PBMCs in response to ZIKV-prME immunization. Rhesus macaques were immunized intradermal (i.d.) with 2 mg of ZIKV-prME plasmid at weeks 0 and 4 administered as 1 mg at each of two sites, with immunization immediately followed by intradermal EP. PBMCs were isolated pre-immunization and at week 6 and were used for the ELISPOT assay to detect IFN-g-secreting cells in response to stimulation with ZIKV-prME peptides as described in Materials and Methods. The number of IFN-g producing cells obtained per million PBMCs against six peptide pools encompassing the entire prME protein is shown. Values represent mean responses in each group (n=5)±SEM.

FIG. 37A and FIG. 37B depict experimental results demonstrating anti-ZIKV antibody responses are induced by ZIKV-prME vaccination of Non-Human Primates (NHPs). FIG. 37A depicts the detection of ZIKV-prME-specific antibody responses following a single DNA vaccination. Anti-ZIKV IgG antibodies were measured pre-immunization and at week 6 by ELISA. FIG. 37B depicts the detection of ZIKV-prME-specific antibody responses following two DNA vaccinations. Anti-ZIKV IgG antibodies were measured pre-immunization and at week 6 by ELISA.

FIG. 38A through FIG. 38D depict experimental results demonstrating Zika-prME immunization confers protection against Zika challenge. FIG. 38A is a schematic representation of NHP Zika challenge study. Rhesus macaques were vaccinated twice at weeks 0 and 4 with pZV-prME DNA via ID route using EP. At week 8, the animals were subcutaneous challenged with Zika-PR209 viral strain. As a control, 5-naïve animals were infected with ZV-PR209 virus. FIG. 38B depicts the sequential viral load determinations for individual animals in Naïve NHP. FIG. 38C depicts the sequential viral load determinations for individual animals in NHP vaccinated once. FIG. 38D depicts the sequential viral load determinations for individual animals in NHP vaccinated twice. The panel shows the peak viral loads for each animal with standard error bars for the three groups are shown (log of viral RNA copies/mL plasma).

FIG. 39A and FIG. 39B depict experimental results from a phase 1 Zika DNA Vaccine Study. FIG. 39A depicts experimental results from a binding ELISA study. FIG. 39B depicts experimental results demonstrating passive transfer and protection.

FIG. 40A and FIG. 40B depict experimental results from immunofluorescence analysis.

FIG. 41A and FIG. 41B depict experimental results demonstrating characterization of the percentage of binding responders.

DETAILED DESCRIPTION OF PREFERRED EMBODIMENTS

Figure 1:
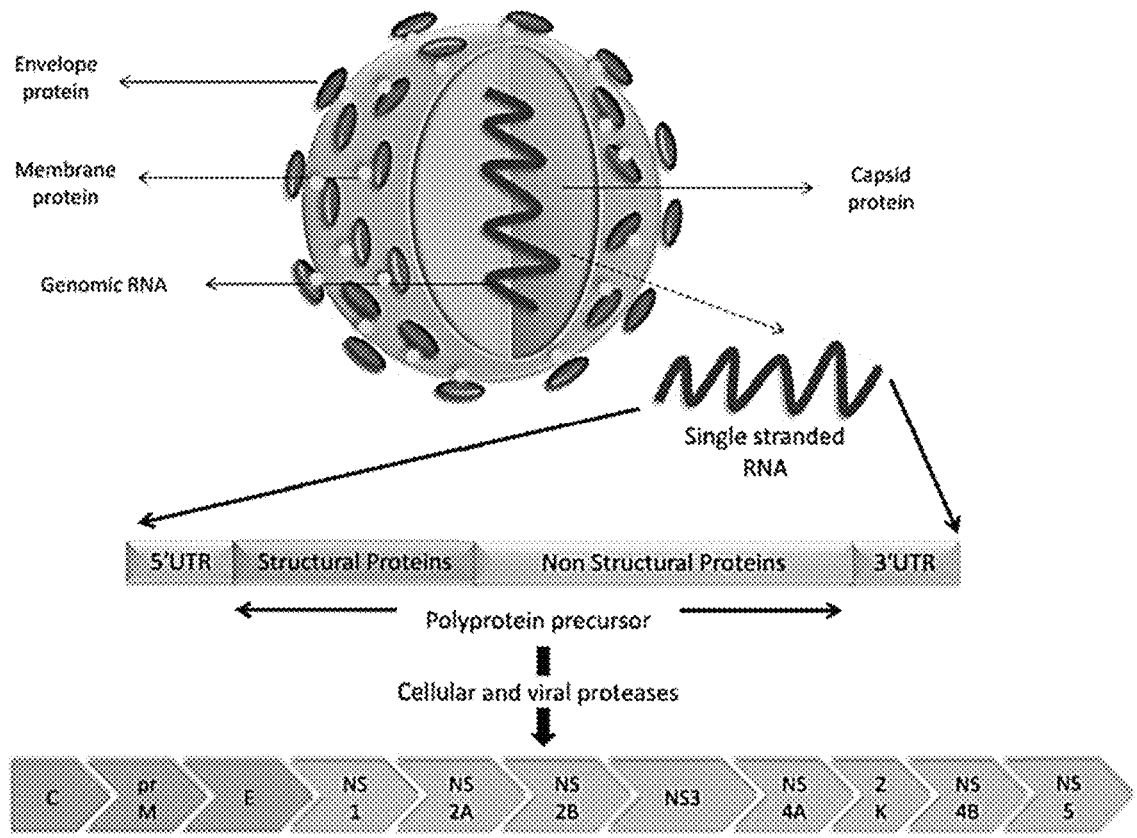
FIG. 1 displays an illustration of a Zika virus particle, the Zika RNA genome, and its translated genes.

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

Definitions

Sequence homology for nucleotides and amino acids as used herein may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" can be calculated using PAUP* 4.0b10 software (D. L. Swofford, Sinauer Associates, Massachusetts). The average similarity of the consensus sequence is calculated compared to all sequences in the phylogenic tree.

As used herein, the term "nucleic acid construct" refers to the DNA or RNA molecules that comprise a nucleotide sequence that encodes protein. The coding sequence, or "encoding nucleic acid sequence," can include initiation and termination signals operably linked to regulatory elements including a promoter and polyadenylation signal capable of directing expression in the cells of the individual to whom the nucleic acid molecule is administered.

As used herein, the term "expressible form" refers to nucleic acid constructs that contain the necessary regulatory elements operably linked to a coding sequence that encodes a protein such that when present in the cell of the individual, the coding sequence will be expressed.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The terms "electroporation," "electro-permeabilization," or "electro-kinetic enhancement" ("EP"), as used interchangeably herein, refer to the use of a transmembrane electric field pulse to induce microscopic pathways (pores) in a bio-membrane; their presence allows biomolecules such as plasmids, oligonucleotides, siRNA, drugs, ions, and/or water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "immune response" is used herein to mean the activation of a host's immune system, e.g., that of a mammal, in response to the introduction of a Zika antigen, e.g., universal Zika antigen, via the provided DNA plasmid vaccines. The immune response can be in the form of a cellular or humoral response, or both.

The term "consensus" or "consensus sequence" is used herein to mean a synthetic nucleic acid sequence, or corresponding polypeptide sequence, constructed based on analysis of an alignment of multiple strains of a Zika gene. The consensus universal Zika can be used to induce broad immunity against multiple subtypes or serotypes of Zika virus.

The term "adjuvant" is used herein to mean any molecule added to the DNA plasmid vaccines described herein to enhance antigenicity of the Zika antigen encoded by the DNA plasmids and encoding nucleic acid sequences described hereinafter.

The term "subtype" or "serotype" is used herein interchangeably and in reference to a virus, for example Zika virus, and means genetic variants of that virus antigen such that one subtype is recognized by an immune system apart from a different subtype. For example, Zika virus subtype 1 is immunologically distinguishable from Zika virus subtype 2.

One aspect of the present invention provides nucleic acid constructs capable of expressing a polypeptide that elicits an immune response in a mammal against Zika virus. The nucleic acid constructs are comprised of an encoding nucleotide sequence and a promoter operably linked to the encoding nucleotide sequence. The encoding nucleotide sequence expresses the polypeptide, wherein the polypeptide includes consensus Zika antigens, including prME. The promoter regulates expression of the polypeptide in the mammal.

In some embodiments the nucleic acid construct can further include an IgE leader sequence operatively linked to an N-terminal end of the coding sequence and operably linked to the promoter. Preferably, the IgE leader has the sequence of SEQ ID NO: 12. The nucleic acid construct can also comprise a polyadenylation sequence attached to the C-terminal end of the coding sequence. Preferably, the nucleic acid construct is codon optimized.

In preferred embodiments, the nucleic acid sequences and amino acid sequences may be selected from:

| SEQ ID NO | Description |
| --- | --- |
| 1 | consensus Zika IgE Leader-prME protein |
| 2 | consensus Zika IgE Leader-prME (construct 1) DNA |
| 3 | consensus Zika IgE Leader-prME (construct 1) protein |
| 4 | consensus Zika IgE Leader-NS1 DNA |
| 5 | consensus Zika IgE Leader-NS1 protein |
| 6 | consensus Zika IgE Leader-capsid DNA |
| 7 | consensus Zika IgE Leader-capsid protein |
| 8 | Zika IgE Leader-prME MR766 DNA |
| 9 | Zika IgE Leader-prME MR766 protein |
| 10 | Zika IgE Leader-prME Brazil DNA |
| 11 | Zika IgE Leader-prME Brazil protein |
| 12 | IgE leader |
| 13 | consensus Zika IgE Leader-NS1 DNA (pGX7211) |
| 14 | consensus Zika IgE Leader-capsid DNA (pGX7212) |
| 15 | Zika IgE Leader-prME Brazil DNA (pGX7213) |
| 16 | Zika IgE Leader-prME MR766 DNA (pGX7214) |

-continued

| SEQ ID NO | Description |
|---|---|
| 17 | Zika PreEnv (MR766) w/out capsid DNA (pGX7210) |
| 18 | Zika PreEnv (MR766) w/out capsid Protein (pGX7210) |

In some embodiments, the DNA sequences herein can have removed from the 5' end the IgE leader sequence (nucleotide sequence encoding SEQ ID NO:12), and the protein sequences herein can have removed from the N-terminus the IgE leader sequence of SEQ ID NO:12.

Another aspect of the present invention provides DNA plasmid vaccines that are capable of generating in a mammal an immune response against a Zika virus. The DNA plasmid vaccines are comprised of a DNA plasmid capable of expressing a consensus Zika antigen in the mammal and a pharmaceutically acceptable excipient. The DNA plasmid is comprised of a promoter operably linked to a coding sequence that encodes the consensus Zika antigen. The consensus Zika antigen is comprised of consensus prME, NS1, capsid, or a fusion of one or more of aforementioned antigens. In one embodiment, the DNA plasmid encodes a consensus Zika antigen. In one embodiment the DNA plasmid encodes a consensus Zika antigen having an amino acid sequence of SEQ ID NO:1 SEQ ID NO: 3, SEQ ID NO: 5, SEQ ID NO: 7, SEQ ID NO: 9, SEQ ID NO: 11 or SEQ ID NO: 18.

In one embodiment, the DNA plasmid comprises a sequence including but not limited to SEQ ID NO: 2, SEQ ID NO: 4, SEQ ID NO: 6, SEQ ID NO: 8, SEQ ID NO: 10, SEQ ID NO: 13, SEQ ID NO: 14, SEQ ID NO: 15, SEQ ID NO: 16 and SEQ ID NO: 17.

In some embodiments, the DNA plasmid includes and encoding sequence that encodes for a Zika antigen minus an IgE leader sequence on the N-terminal end of the coding sequence. In some embodiments, the DNA plasmid further comprises an IgE leader sequence attached to an N-terminal end of the coding sequence and operably linked to the promoter. Preferably, the IgE leader has the sequence of SEQ ID NO:12.

The DNA plasmid can further include a polyadenylation sequence attached to the C-terminal end of the coding sequence. Preferably, the DNA plasmid is codon optimized.

In some embodiments, the pharmaceutically acceptable excipient is an adjuvant. Preferably, the adjuvant is selected from the group consisting of: IL-12 and IL-15. In some embodiments, the pharmaceutically acceptable excipient is a transfection facilitating agent. Preferably, the transfection facilitating agent is a polyanion, polycation, or lipid, and more preferably poly-L-glutamate. Preferably, the poly-L-glutamate is at a concentration less than 6 mg/ml. Preferably, the DNA plasmid vaccine has a concentration of total DNA plasmid of 1 mg/ml or greater.

In some embodiments, the DNA plasmid comprises a plurality of unique DNA plasmids, wherein each of the plurality of unique DNA plasmids encodes a polypeptide comprising a consensus prME protein, consensus prME (construct 1), consensus NS1 DNA, or consensus capsid protein.

The DNA plasmid vaccines can include a DNA plasmid encoding an amino acid sequence, including but not limited to, SEQ ID NO:1, SEQ ID NO:3, SEQ ID NO:5, SEQ ID NO: 7, SEQ ID NO: 9, SEQ ID NO: 11, and SEQ ID NO: 18.

In one embodiment, the DNA plasmid vaccines can include a DNA plasmid comprising a sequence that includes but is not limited to SEQ ID NO:2, SEQ ID NO: 4, SEQ ID NO: 6, SEQ ID NO: 8, SEQ ID NO: 10, SEQ ID NO: 13, SEQ ID NO: 14, SEQ ID NO: 15, SEQ ID NO: 16, and SEQ ID NO:17.

In some embodiments, the mammal in which the DNA plasmid vaccines generate an immune response is a primate. Preferably, the mammal is a primate. The immune response can be either a humoral response or cellular response, and preferably both.

Another aspect of the present invention provides methods of eliciting an immune response against Zika virus in a mammal, comprising delivering a DNA plasmid vaccine to tissue of the mammal, the DNA plasmid vaccine comprising a DNA plasmid capable of expressing a consensus antigen of the Zika virus in a cell of the mammal to elicit an immune response in the mammal, and electroporating cells of the tissue to permit entry of the DNA plasmids into the cells.

In some embodiments, the methods of eliciting an immune response includes a delivering step that comprises injecting the DNA plasmid vaccine into intradermic, subcutaneous or muscle tissue.

In some embodiments, the methods of eliciting an immune response can further comprise presetting a current that is desired to be delivered to the tissue; and electroporating cells of the tissue with a pulse of energy at a constant current that equals the preset current.

In some embodiments, the methods of eliciting an immune response further comprise measuring the impedance in the electroporated cells; adjusting energy level of the pulse of energy relative to the measured impedance to maintain a constant current in the electroporated cells. The measuring and adjusting steps preferably occur within a lifetime of the pulse of energy.

In some embodiments, the electroporating step comprises delivering the pulse of energy to a plurality of electrodes according to a pulse sequence pattern that delivers the pulse of energy in a decentralized pattern.

In some embodiments of the present invention, the DNA plasmid vaccines can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1-alpha, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

In some embodiments, the pharmaceutically acceptable excipient is a transfection facilitating agent, which can include the following: surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. Preferably, the transfection facilitating agent is a polyanion, polycation, including poly-L-glutamate (LGS), or lipid. Preferably, the transfection facilitating agent is poly-L-glutamate, and more preferably, the poly-L-glutamate is present in the DNA plasmid vaccine at a concentration less than 6 mg/ml. In some embodiments, the concentration of poly-L-glutamate in the DNA plasmid vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

In some embodiments, the DNA plasmid vaccine can be delivered to a mammal to elicit an immune response; preferably the mammal is a primate, including human and nonhuman primate, a cow, pig, chicken, dog, or ferret. More preferably, the mammal is a human primate.

One aspect of the present invention relates to methods of eliciting an immune response against a Zika virus in a mammal. The methods include delivering a DNA plasmid vaccine to tissue of the mammal, and electroporating cells of the tissue with a pulse of energy at a constant current effective to permit entry of the DNA plasmids into the cells. The DNA plasmid vaccine comprises a DNA plasmid capable of expressing a Zika antigen, preferably a consensus antigen, in a cell of the mammal to elicit an immune response in the mammal. The methods of eliciting an immune response including electroporating cells of the tissue with a pulse of energy at a constant current effective to permit entry of the DNA plasmids in the cells.

In some embodiments, the methods of the present invention include the delivering step, which comprises injecting the DNA plasmid vaccine into intradermic, subcutaneous or muscle tissue. Preferably, these methods include using an in vivo electroporation device to preset a current that is desired to be delivered to the tissue; and electroporating cells of the tissue with a pulse of energy at a constant current that equals the preset current. In some embodiments, the electroporating step further comprises: measuring the impedance in the electroporated cells; adjusting energy level of the pulse of energy relative to the measured impedance to maintain a constant current in the electroporated cells; wherein the measuring and adjusting steps occur within a lifetime of the pulse of energy.

In some embodiments, the electroporating step comprises delivering the pulse of energy to a plurality of electrodes according to a pulse sequence pattern that delivers the pulse of energy in a decentralized pattern.

The present invention also comprises DNA fragments that encode a polypeptide capable of eliciting an immune response in a mammal substantially similar to that of the non-fragment for Zika antigen. The DNA fragments are fragments selected from at least one of the various encoding nucleotide sequences of the present invention, including nucleotide sequence encoding SEQ ID NO:1, SEQ ID NO:2, nucleotide sequence encoding SEQ ID NO:3, SEQ ID NO:4, nucleotide sequence encoding SEQ ID NO:5, SEQ ID NO:6, nucleotide sequence encoding SEQ ID NO: 7, SEQ ID NO:8, nucleotide sequence encoding SEQ ID NO: 9, SEQ ID NO:10, nucleotide sequence encoding SEQ ID NO: 11, SEQ ID NO:17, nucleotide sequence encoding SEQ ID NO: 18, and SEQ ID NOs:14-16, and can be any of the following described DNA fragments, as it applies to the specific encoding nucleic acid sequence provided herein. In some embodiments, DNA fragments can comprise 30 or more, 45 or more, 60 or more, 75 or more, 90 or more, 120 or more, 150 or more, 180 or more, 210 or more, 240 or more, 270 or more, 300 or more, 320 or more, 340 or more, or 360 or more nucleotides. In some embodiments, DNA fragments can comprise coding sequences for the immunoglobulin E (IgE) leader sequences. In some embodiments, DNA fragments can comprise fewer than 60, fewer than 75, fewer than 90, fewer than 120, fewer than 150, fewer than 180, fewer than 210, fewer than 240, fewer than 270, fewer than 300, fewer than 320, fewer than 340, or fewer than 360 nucleotides.

The present invention includes polypeptides encoded by the encoding nucleotide sequences and can include polypeptides having amino acid sequences of SEQ ID NOS: 1, 3, 5, 7, 9, 11, 18. The present invention also comprises polypeptide fragments that are capable of eliciting an immune response in a mammal substantially similar to that of the non-fragment for Zika antigen. The polypeptide fragments are selected from at least one of the various polypeptide sequences of the present invention, including SEQ ID NOS: 1, 3, 5, 7, 9, 11, 18, and can be any of the following described polypeptide fragments, as it applies to the specific polypeptide sequence provided herein. In some embodiments, polypeptide fragments can comprise 15 or more, 30 or more, 45 or more, 60 or more, 75 or more, 90 or more, 100 or more, 110 or more, or 120 or more amino acids. In some embodiments, polypeptide fragments can comprise fewer than 30, fewer than 45, fewer than 60, fewer than 75, fewer than 90, fewer than 100, fewer than 110, or fewer than 120 amino acids.

The determination of a functional fragment eliciting an immune response in a mammal substantially similar to that of the non-fragment for the Zika antigen can be readily determined by one of ordinary skill. The fragment can be analyzed to contain at least one, preferably more, antigenic epitopes as provided by a publicly available database, such as National Center for Biotechnology Information (NCBI). In addition, immune response studies can be routinely assessed using mice and antibody titers and ELISpots analysis, such as that shown in the Examples below.

Vaccines

In some embodiments, the invention provides improved vaccines by providing proteins and genetic constructs that encode proteins with epitopes that make them particularly effective as immunogens against which immune responses can be induced. Accordingly, vaccines can be provided to induce a therapeutic or prophylactic immune response.

According to some embodiments of the invention, a vaccine according to the invention is delivered to an individual to modulate the activity of the individual's immune system and thereby enhance the immune response. When a nucleic acid molecule that encodes the protein is taken up by cells of the individual the nucleotide sequence is expressed in the cells and the protein is thereby delivered to the individual. Aspects of the invention provide methods of delivering the coding sequences of the protein on nucleic acid molecule such as plasmid.

According to some aspects of the present invention, compositions and methods are provided which prophylactically and/or therapeutically immunize an individual.

When taken up by a cell, the DNA plasmids can remain in the cell as separate genetic material. Alternatively, RNA may be administered to the cell. It is also contemplated to provide the genetic construct as a linear minichromosome including a centromere, telomeres and an origin of replication. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the mammals to whom the nucleic acid construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from simian virus 40 (SV40), mouse mammary tumor virus (MMTV) promoter, human immunodeficiency virus (HIV) such as the bovine immunodeficiency virus (BIV) long terminal repeat (LTR) promoter, Moloney virus, avian leukosis virus (ALV), cytomegalovirus (CMV) such as the CMV immediate early promoter, Epstein Barr virus (EBV), Rous sarcoma virus (RSV) as well as promoters from human genes such as human actin, human myosin, human hemoglobin, human muscle creatine and human metalothionein; in other embodiments, promoters can be tissue specific promoters, such as muscle or skin specific promoters, natural or synthetic. Examples of such promoters are described in US patent application publication no. US20040175727, which is incorporated hereby in its entirety.

Examples of polyadenylation signals useful to practice the present invention, especially in the production of a genetic vaccine for humans, include but are not limited to SV40 polyadenylation signals, LTR polyadenylation signals, bovine growth hormone (bGH) polyadenylation signals, human growth hormone (hGH) polyadenylation signals, and human β-globin polyadenylation signals. In particular, the SV40 polyadenylation signal that is in pCEP4 plasmid (Invitrogen, San Diego, CA), referred to as the SV40 polyadenylation signal, can be used.

In addition to the regulatory elements required for DNA expression, other elements may also be included in the DNA molecule. Such additional elements include enhancers. The enhancer may be selected from the group including but not limited to: human actin, human myosin, human hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, CA) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons that encode said protein may be selected which are most efficiently transcribed in the host cell. One having ordinary skill in the art can produce DNA constructs that are functional in the cells.

In some embodiments, nucleic acid constructs may be provided in which the coding sequences for the proteins described herein are linked to IgE leader peptide, or such IgE leader is removed. In some embodiments, proteins described herein are linked to IgE signal peptide, or such IgE leader is removed.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well-known expression systems. For example, the commercially available plasmid pSE420 (Invitrogen, San Diego, Calif.) may be used for production of protein in *Escherichia coli* (*E. coli*). The commercially available plasmid pYES2 (Invitrogen, San Diego, Calif.) may, for example, be used for production in *Saccharomyces cerevisiae* strains of yeast. The commercially available MAXBAC™ complete baculovirus expression system (Invitrogen, San Diego, Calif.) may, for example, be used for production in insect cells. The commercially available plasmid pcDNA or pcDNA3 (Invitrogen, San Diego, Calif.) may, for example, be used for production in mammalian cells such as Chinese hamster ovary (CHO) cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989)). Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line, or cells of targeted tissue, into which the constructs are transfected. Examples of constitutive promoters include promoters from cytomegalovirus (CMV) or SV40. Examples of inducible promoters include mouse mammary leukemia virus or metallothionein promoters. Those having ordinary skill in the art can readily produce genetic constructs useful for transfecting cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. Preferably, the nucleic acid molecules such as the DNA plasmids described herein are delivered via DNA injection and along with in vivo electroporation.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, "microprojectile bombardment gone guns", or other physical methods such as electroporation ("EP"), "hydrodynamic method", or ultrasound.

Examples of electroporation devices and electroporation methods preferred for facilitating delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

The following is an example of methods of the present invention, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 µs, 20 µs, 10 µs or 1 µs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some preferred embodiments, the DNA plasmids are delivered with an adjuvant that are genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-la, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The DNA plasmid vaccines according to the present invention comprise DNA quantities of from about 1 nanogram to 10 milligrams; about 1 microgram to about 10 milligrams; or preferably about 0.1 microgram to about 10 milligrams; or more preferably about 100 microgram to about 1 milligram. In some preferred embodiments, DNA plasmid vaccines according to the present invention comprise about 5 nanogram to about 1000 micrograms of DNA. In some preferred embodiments, the DNA plasmid vaccines contain about 10 nanograms to about 800 micrograms of DNA. In some preferred embodiments, the DNA plasmid vaccines contain about 0.1 to about 500 micrograms of DNA. In some preferred embodiments, the DNA plasmid vaccines contain about 1 to about 350 micrograms of DNA. In some preferred embodiments, the DNA plasmid vaccines contain about 25 to about 250 micrograms of DNA. In some preferred embodiments, the DNA plasmid vaccines contain about 100 microgram to about 1 milligram DNA.

The DNA plasmid vaccines according to the present invention are formulated according to the mode of administration to be used. In cases where DNA plasmid vaccines are injectable compositions, they are sterile, and/or pyrogen free and/or particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, methods of eliciting an immune response in mammals against a consensus Zika antigen include methods of inducing mucosal immune responses. Such methods include administering to the mammal one or more of CTACK protein, TECK protein, MEC protein and functional fragments thereof or expressible coding sequences thereof in combination with an DNA plasmid including a consensus Zika antigen, described above. The one or more of CTACK protein, TECK protein, MEC protein and functional fragments thereof may be administered prior to, simultaneously with or after administration of the DNA plasmid Zika vaccines provided herein. In some embodiments, an isolated nucleic acid molecule that encodes one or more proteins of selected from the group consisting of: CTACK, TECK, MEC and functional fragments thereof is administered to the mammal.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with a muscle or skin EP device described herein have high DNA concentrations, preferably concentrations that include microgram to tens of milligram quantities, and preferably milligram quantities, of DNA in small volumes that are optimal for delivery to the skin, preferably small injection volume, ideally 25-200 microliters (μL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the EP devices of the present invention can be formulated or manufactured using a combination of known devices and techniques, but preferably they are manufactured using an optimized plasmid manufacturing technique that is described in U.S. application Ser. No. 12/126,611 which published as US Publication No. 20090004716, which published Jan. 1, 2009. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in US Publication No. 20090004716 and those described in U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The publications, US Publication No. 20090004716 and U.S. Pat. No. 7,238,522, are hereby incorporated in their entirety.

Example 1: Zika prME Vaccine

Zika Vaccine Approach

Figure 2:
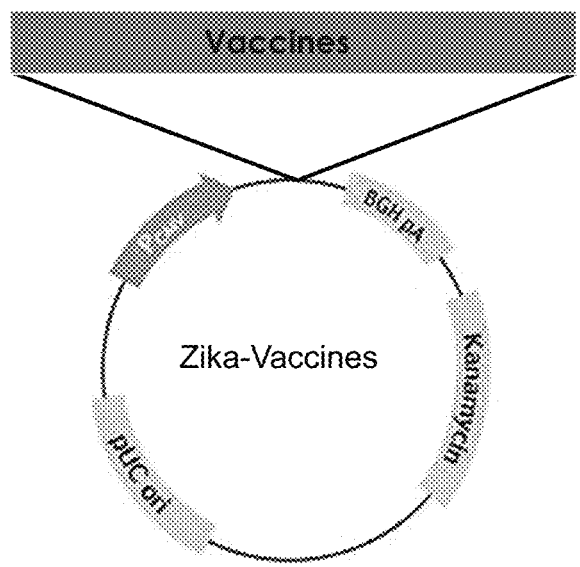
FIG. 2 displays a plasmid map for a Zika vaccine, showing the site of the location for the insert (expression cassette) that encodes the Zika antigens.
Figure 3:
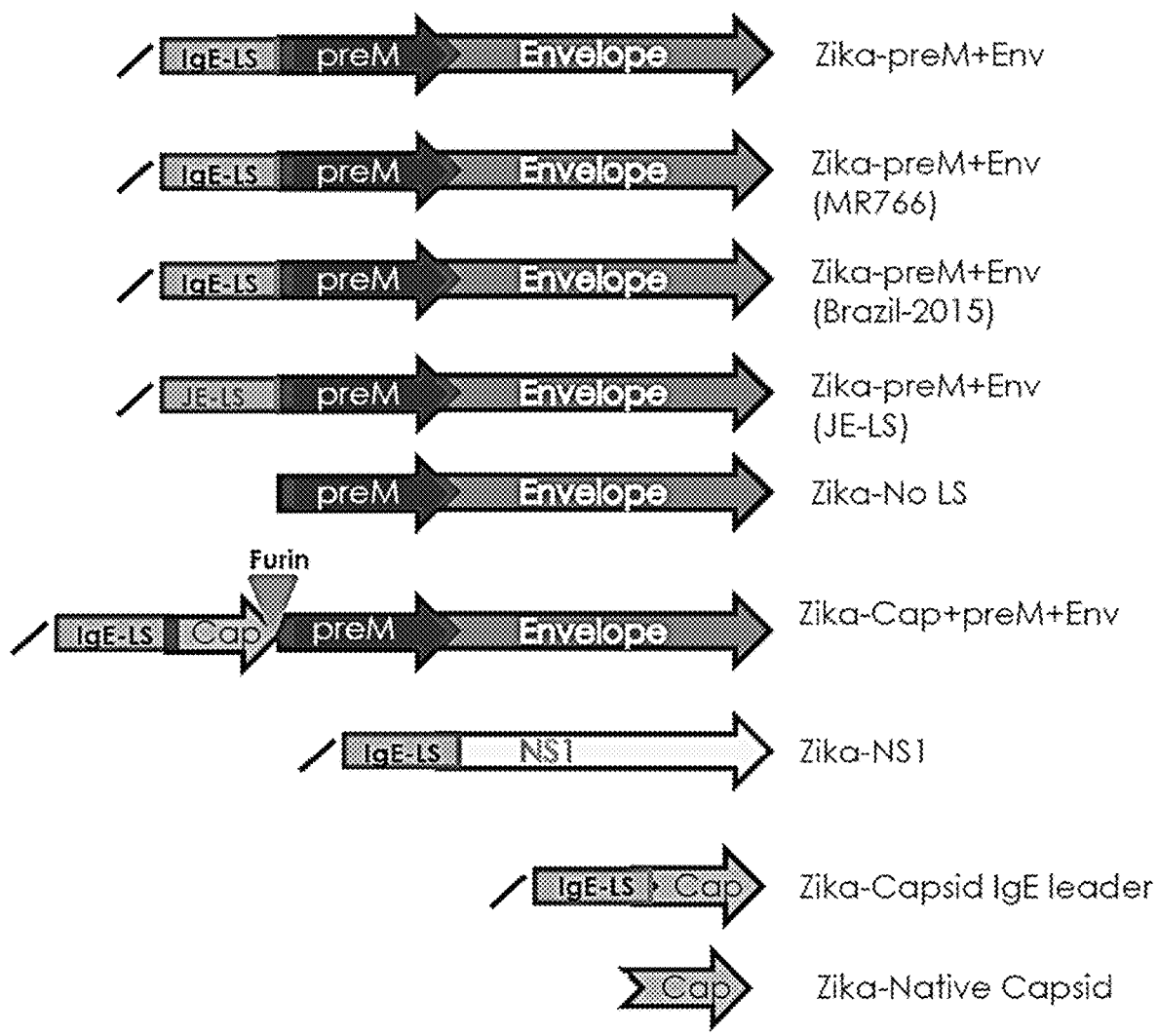
FIG. 3 displays drawings that show the linear structure of various Zika antigen designs.

As shown in FIG. 2, a Zika antigen expression construct was generated with the backbone shown therein. An expression cassette was inserted behind a CMV promoter and with a trailing polyadenylation tail. The cassette can include encoding sequences for the antigens shown in FIG. 3, including prME, NS1, and capsid.

Phylogenetic Analysis and Vaccine Design of Zika prME

Figure 5:
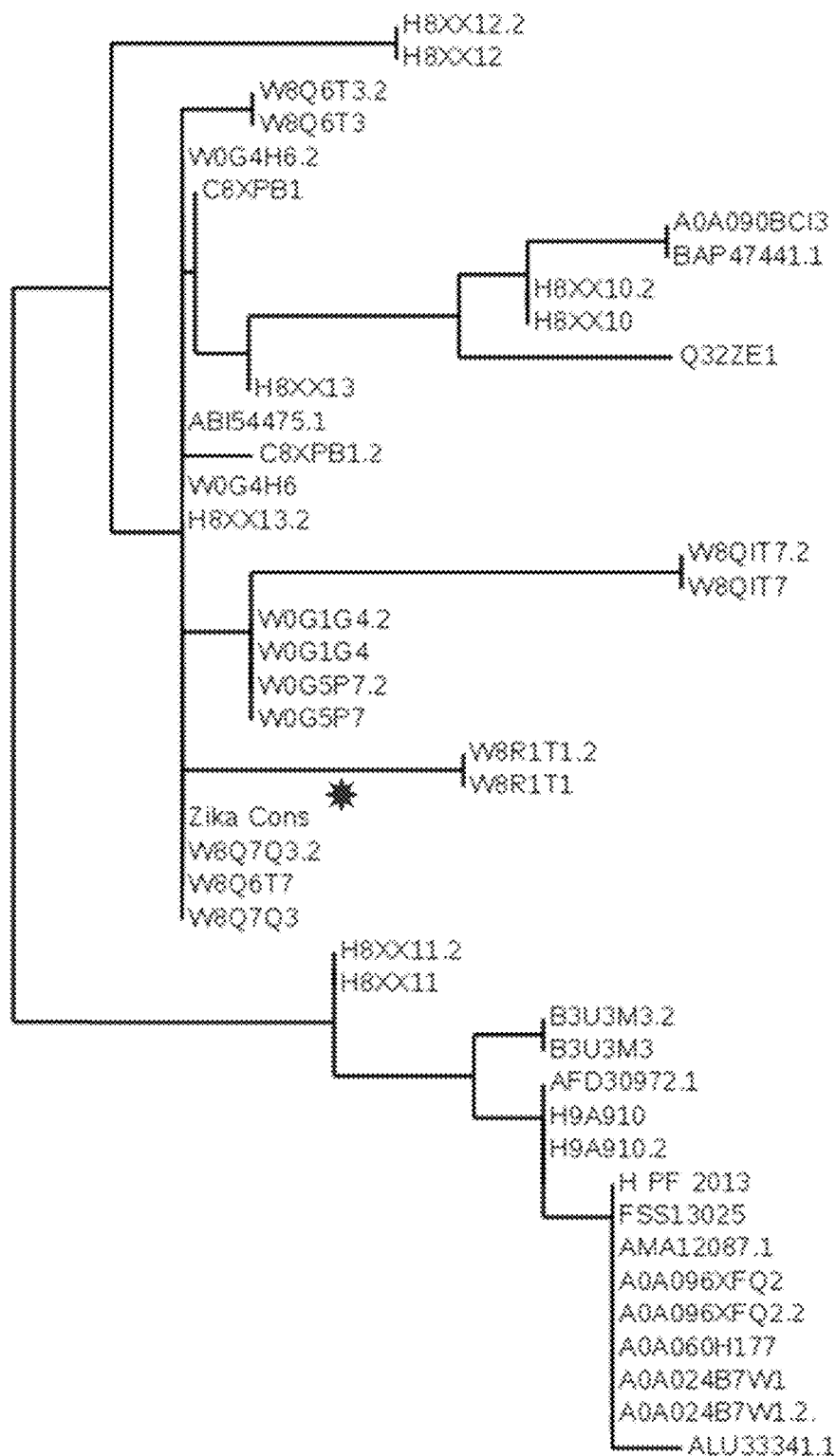
FIG. 5 and FIG. 6 display the genetic relationship between various Zika virus strains.
Figure 6:
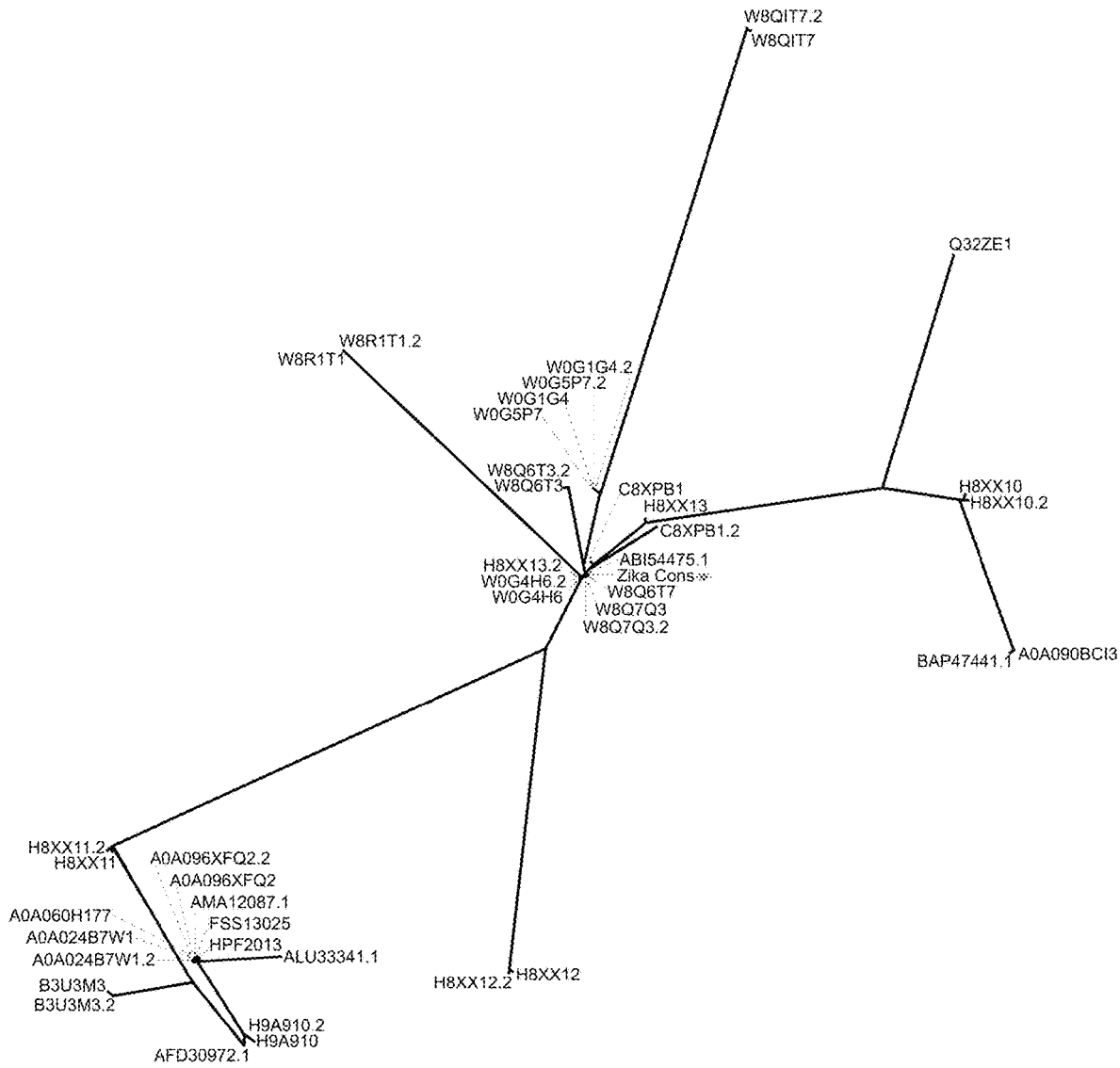
Figure 7:
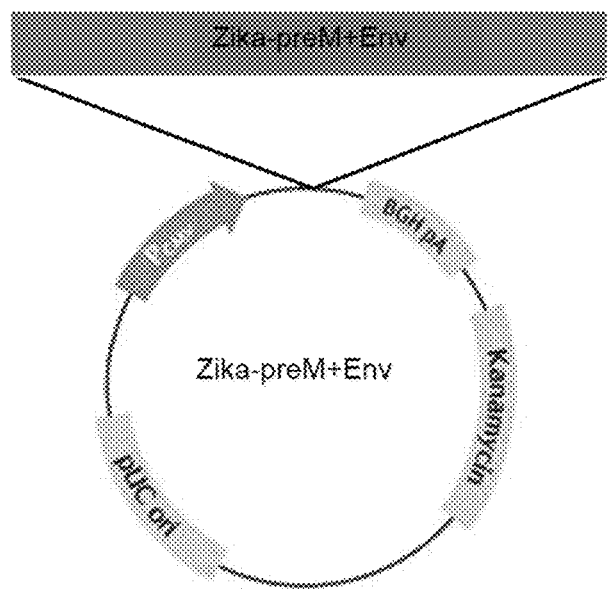
FIG. 7 displays a plasmid map for a Zika vaccine, showing the site of the location for the insert (expression cassette) that encodes Zika-prM+Env.
Figure 8:
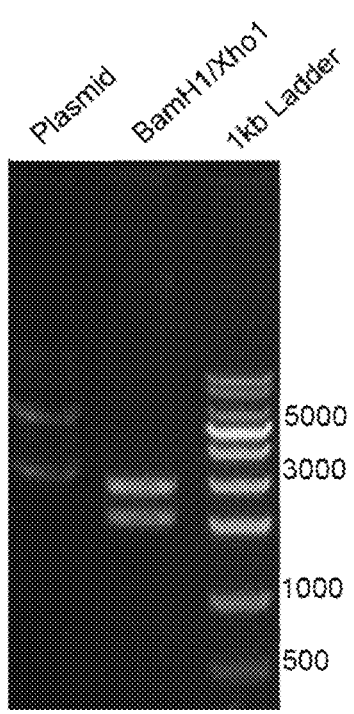
FIG. 8 displays a gel electrophoresis image that shows the presence of expression cassette.

A phylogenetic analysis was made as shown in FIG. 5 and FIG. 6. The star shows the location of the consensus prME sequence SEQ ID NO:3. This consensus prME is shown inserted into the cloning site in the expression vector according to that in FIG. 7.

Figure 9A:
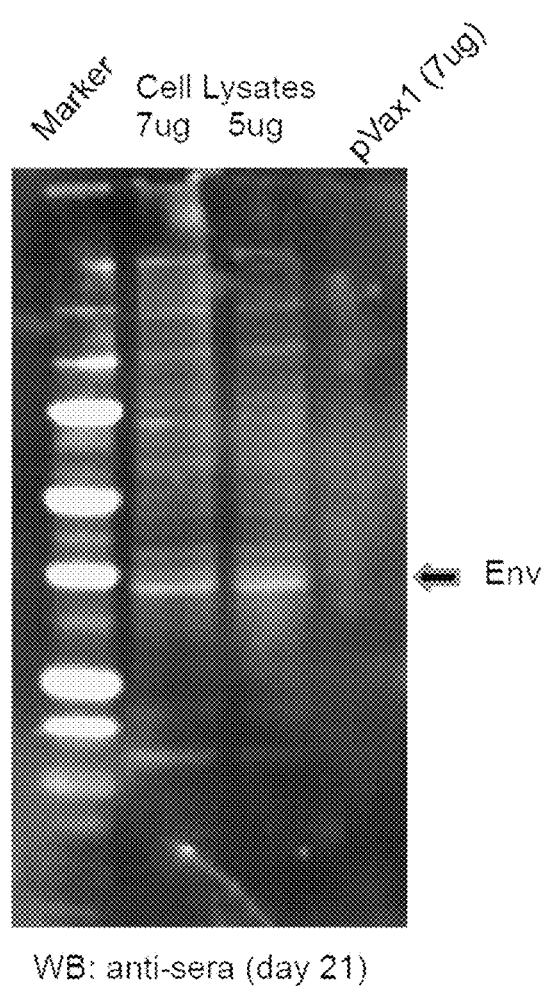
FIG. 9A and FIG. 9B displays western blot gels that show Zika-envelope protein.
Figure 9B:
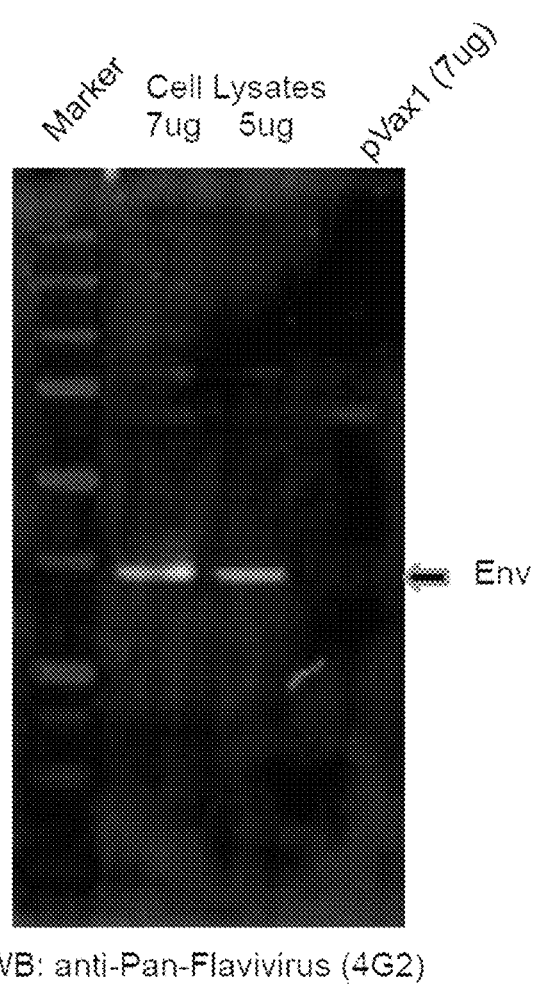

The expressed protein was characterized by Western blot analysis as shown in FIG. 9A and FIG. 9B, which shows specific binding to anti-flavivirus antibodies.

Figures 10A, 10B:
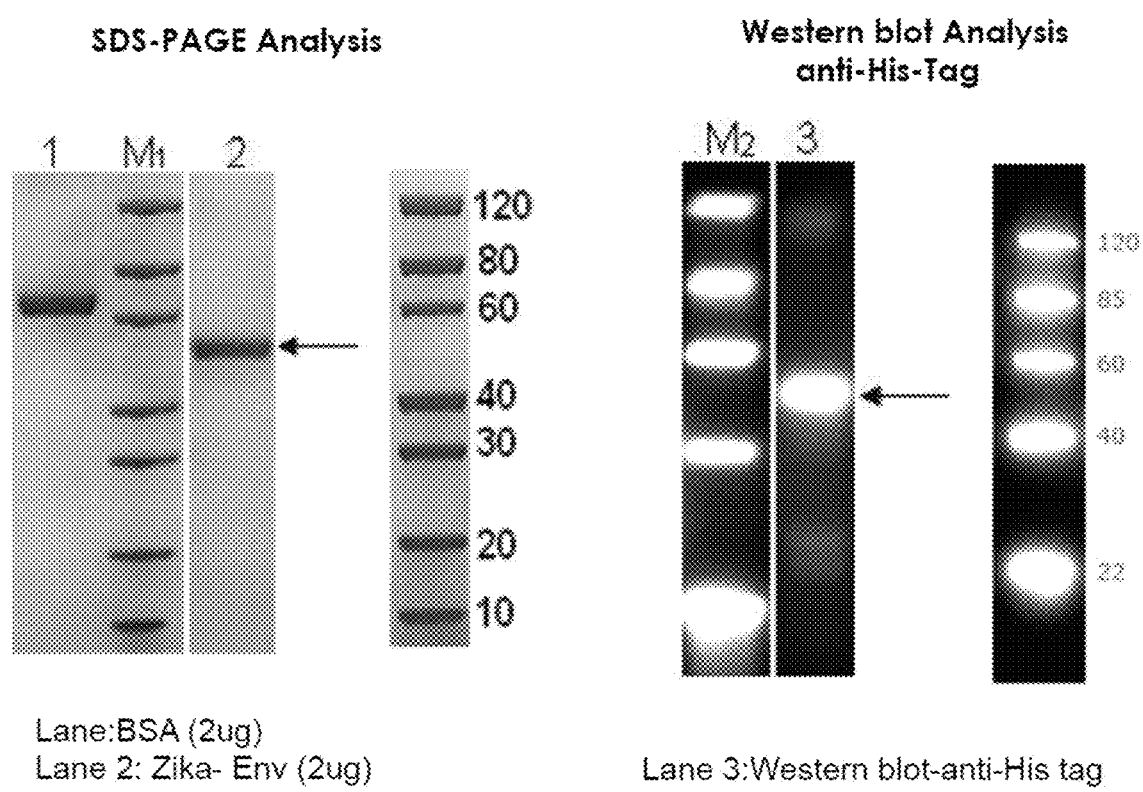
FIG. 10A displays an SDS-PAGE gel that shows purification of Zika-envelope protein.
FIG. 10B displays a western blot gel that shows purification of Zika-envelope protein.

The protein was then purified, as shown in FIG. 10A and FIG. 10B.

Mouse Immunization

Animals—Balb/C mice (group of 8)

Plasmids—Zika-prME (encoding sequence including SEQ ID NO:2)

Devices—3P electroporation device (Inovio Pharmaceuticals, Plymouth Meeting, PA) Immunization Schedule:

Mice were immunized a total of 3 times with DNA: once (prime) at day 0, and boost at days 14, & 28. Immune analysis was performed one week post DNA 3rd immunization.

Injection method—intramuscular

Bleeding Schedule—Pre bleed and at day 14, 28 & 35

Bleed Method—retro orbital

Groups &Animals—10 animals/group×3 Groups=30

1) pVax1
2) pVax-1 Zika preME (SEQ ID NO:2)

Cellular Immune Responses Elicited by Zika prME Vaccine

Figure 11:
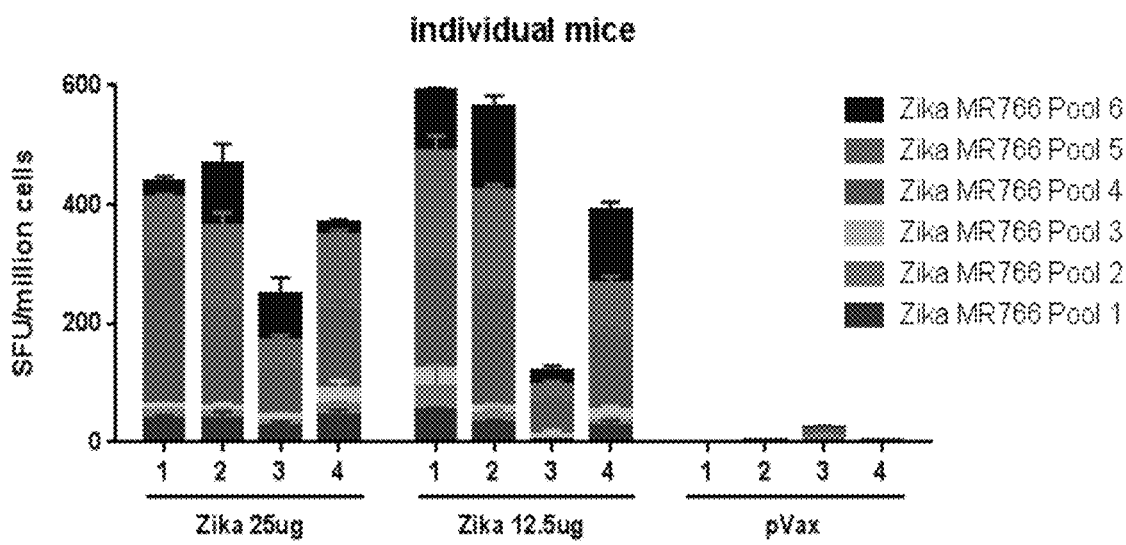
FIG. 11 and FIG. 12 display bar graphs showing spike-specific CD8 T-lymphocyte responses assessed by IFN-gamma ELISpot assay against peptide pools covering pre-M+envelope antigen.
Figure 12:
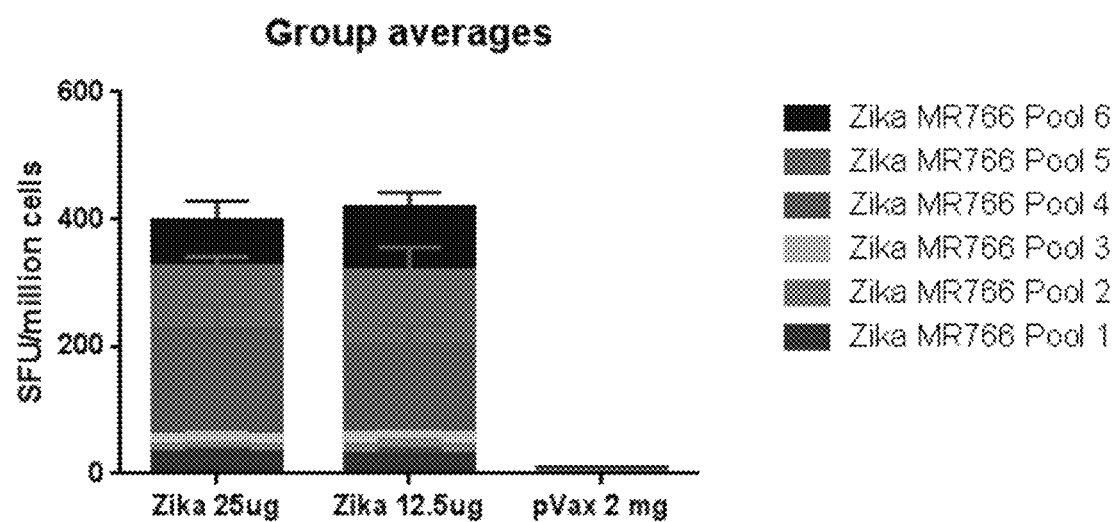

Spike-specific CD8 T-lymphocyte responses were assessed by IFN-g ELISpot assay against peptide pools covering prME antigen. See FIG. 11 and FIG. 12. Mean responses in each group are one week after the third immunization. Error bars indicate standard errors. Responses to pVax control are shown.

Induction of Antibodies in Mice

Figure 13A:
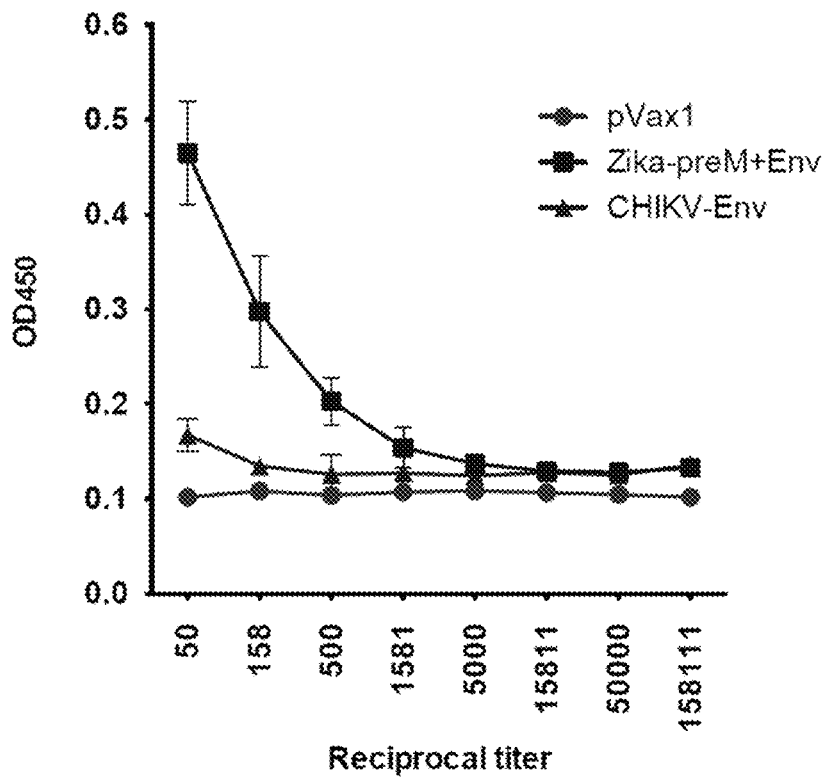
FIG. 13A and FIG. 13B display a graph that represents binding ELISA of samples, showing Zika prM+Env vaccination of mice elicits a positive antibody response which reacts with Zika-envelope antigen.
Figure 13B:
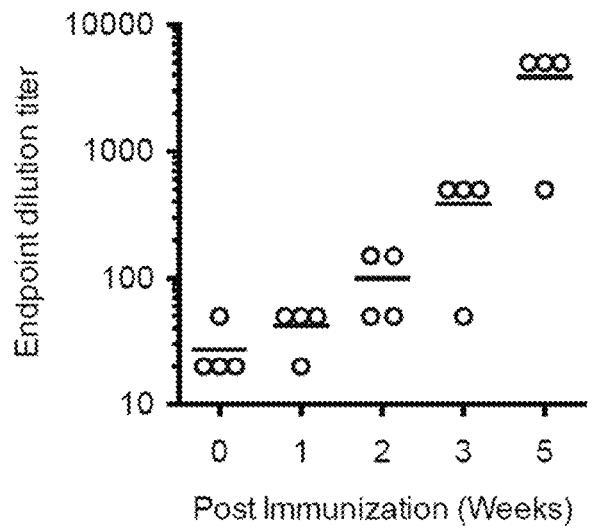
Figure 14A:
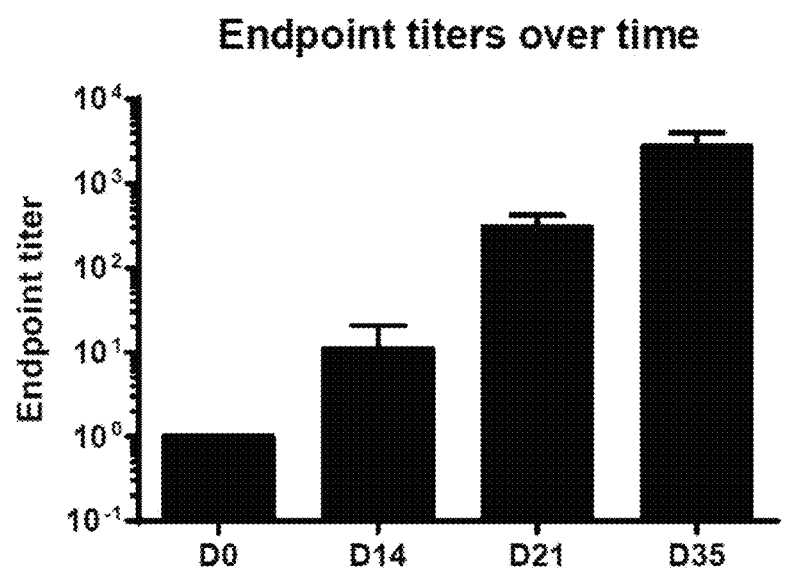
FIG. 14A and FIG. 14B displays graphs that show that ZV-prME immunogen elicits a considerable antibody response which reacts specifically with Zika-Envelope antigen. The cross reactivity of the ZpME sera against Dengue 1, 2, 3, and 4 antigen Envs were negative, while against Zika Env showed strong binding.
Figure 14B:
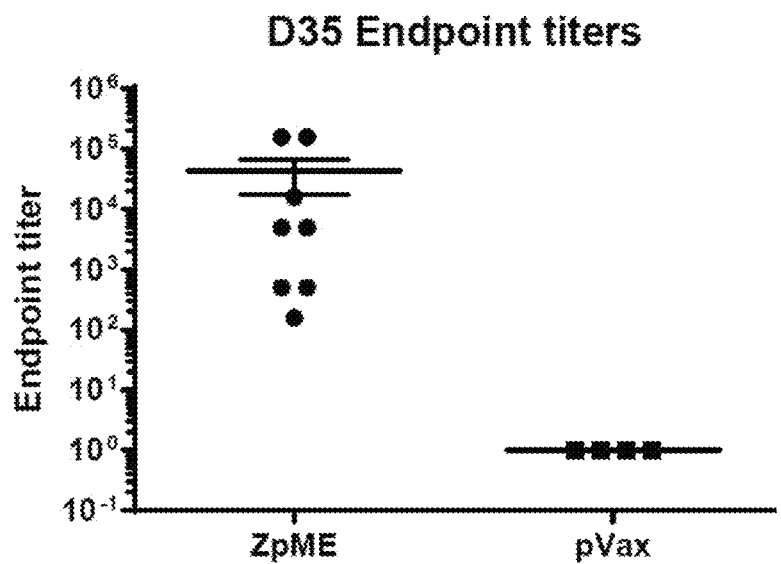

Zika prME vaccination of mice elicited a positive antibody response which reacts with Zika-Envelope antigen. See FIG. 13 and FIG. 14.

Zika prME vaccine were found to be immunogenic in mice based on binding to recombinant protein E antigen. Seroconversion was observed in immunized animals by Western blot analysis and ELISA.

Example 2: Novel DNA Vaccine Against Zika Virus prME Induces Protective Immunity In Vivo Described herein is a novel synthetic DNA consensus-based vaccine targeting the pre-membrane+envelope proteins of Zika virus. Following construct expression confirmation, mice and non-human primates were immunized, through electroporation, showing the induction of both cellular and humoral immunity with neutralization activity in vaccinated animals. In IFN-α/β $R^{-/-}$ mice, either a single or two-injection immunization was 100% protective against weight loss or death in this lethal challenge model. This represents the first Zika viral vaccine approved for human trials.

The materials and methods are now described.

Cells, Virus, and Animals

Human embryonic kidney (HEK) 293T (American Type Culture Collection (ATCC) #CRL-N268, Manassas, VA) and Vero CCL-81 (ATCC #CCL-81) cells were maintained in Dulbecco's modified Eagle's medium (DMEM; Gibco-Invitrogen) supplemented with 10% Fetal Bovine Serum (FBS) and 1% Penicillin and Streptomycin and passaged upon confluence. Neuronal tumor cell lines SK-N-SH (ATCC HTB-11) and U87MG (ATCC HTB-14) were maintained in Eagle Minimum Essential Medium (MEM; Corning-cellgro) supplemented with 10% Fetal Bovine Serum (FBS) and 1% Penicillin and Streptomycin and passaged upon confluence. Both Zika virus strains MR766 (a kind gift from Dr. Susan Weiss) and PR209 (Bioqual, MD) were amplified in Vero cells and stocks were titered by standard plaque assay on Vero cells.

C57/BL6 and IFNAR$^{-/-}$ mice and rhesus macaques procedures were carried out under ketamine anesthesia. The animals were housed in adjoining individual primate cages allowing social interactions, under controlled conditions of humidity, temperature, and light (12-hour light/12-hour dark cycles). Food and water were available ad libitum. The animals were monitored twice daily and fed commercial monkey chow, treats, and fruits twice daily.

DNA Vaccine Construct and Synthesis

The Zika-prM+Env plasmid DNA construct encodes full-length precursor of membrane (prM) and Envelope (E) proteins. A consensus strategy was used and the consensus sequences were determined by the alignment of current Zika prM+E protein sequences. The vaccine insert was genetically optimized (i.e. codon and RNA optimization) for enhanced expression in humans and an IgE leader sequence was added to facilitate expression. The construct was synthesized commercially (Genscript, NJ), and then sub cloned into a modified pVax1 expression vector under the control of the cytomegalovirus immediate-early promoter as described before (Muthumani et al., 2015, Sci Trans Med 7:301ra132). The final construct is named ZIKV-prME vaccine and the control plasmid backbone is pVax1. In addition, a number of other matched DNA constructs encoding the prM and Env genes from MR766 and a 2016 Brazilin outbreak strain were also designed, for further evaluation. Large-scale amplifications of DNA constructs were carried out by Inovio, (Plymouth Meeting, PA) and purified plasmid DNA was formulated in water for immunizations. The size of the DNA inserts was confirmed via agarose gel electrophoresis. Phylogenetic analysis was performed by multiple-alignment with ClustalW using MEGA version 5 software (Muthumani et al., 2015, Sci Trans Med 7:301ra132).

DNA Immunizations and Electroporation

Mouse immunogenicity studies: Female C57BL/6 mice (6 to 8 weeks old) and IFNAR$^{-/-}$ mice (5 to 7 weeks old) were immunized (n=4) with 25 μg of DNA in a total volume of 20 or 30 μl of water delivered into the tibialis anterior muscle with in vivo EP delivery. In vivo EP was delivered, with the CELLECTRA adaptive constant current EP device (Inovio Pharmaceuticals, PA), at the same site immediately following immunization. A three-pronged CELLECTRA minimally invasive device was inserted ~2 mm into the muscle. Square-wave pulses were delivered through a triangular 3-electrode array consisting of 26-gauge solid stainless steel electrodes and two constant current pulses of 0.1 Amps were delivered for 52 microsecond/pulse separated by a 1 second delay. Further protocols for the use of EP have been previously described in detail. Mice were immunized three times at two-week intervals and sacrificed 1 week after final immunization. Blood was collected after each immunization for analysis of cellular and humoral immune responses (Muthumani et al., 2015, Sci Trans Med 7:301ra132). Rhesus macaque immunogenicity studies: 5 rhesus macaques were immunized ID at 2 sites twice 4 weeks apart with 2 mg ZIKV-prME vaccine. EP was delivered immediately using the same device described for mouse immunizations.

Challenge studies in IFNAR$^{-/-}$ Mice

IFNAR$^{-/-}$ mice were split into three groups. The first group of mice were immunized once and challenged with $10^6$ PFU ZIKV PR209 2 weeks after immunization. The second group of mice were immunized twice at two week intervals and challenged with 106 PFU ZIKV PR209 1 week after the second immunization. The third group of mice were immunized twice at two week intervals and challenged with $2 \times 10^6$ PFU ZIKV PR209 1 week after the second immunization. Post challenge, animals were weighed and body temperature measured daily by a subcutaneously located temperature chip. In addition, they were observed for clinical signs of disease twice daily (decreased mobility; hunched posture; hind limb knuckle walking (partial paralysis), paralysis of one hind limb or both hind limbs). Criteria for euthanasia on welfare grounds consisted of 20% weight loss or observation of any abnormal clinical signs.

Western Blot and Immunofluorescence Assays

For in vitro expression studies, transfections were performed using the GeneJammer reagent, following the manufacturer's protocols (Agilent). Briefly, cells were grown to 50% confluence in a 35-mm dish and transfected with 1 ug of Zika prME vaccine. The cells were harvested 2 days after transfection, washed twice with phosphate-buffered. saline (PBS), and lysed with cell lysis buffer (Cell Signaling Technology). Western Blot was used to verify the expression of the Zika preM+Env protein from the harvested cell lysate, as described previously (Muthumani et al., 2015, Sci Trans Med 7:301ra132).

The specificity of the mouse and RM immune serum was confirmed using Western Blot analysis. 3-12% Bis-Tris NuPAGE gels (Life Technologies) were loaded with 5 μg or 1 ug of ZIKV Env recombinant protein and the Odyssey protein Molecular Weight Marker (Product #928-40000). Gels were run at 200 V for 50 minutes in MOPS buffer. The proteins were transferred onto nitrocellulose membranes using the iBlot 2 Gel Transfer Device (Life Technologies). The membranes were blocked in PBS Odyssey blocking buffer (LI-COR Biosciences) for 1 hour at room temperature. The anti-Flavivirus group antigen (MAB10216-Clone D1-4G2-4-15) antibody was diluted 1:500 to detect vaccine expression and the immune serum from mice and RM was diluted 1:50 in Odyssey blocking buffer with 0.2% Tween 20 (Bio-Rad) and incubated with the membranes overnight at 4° C. The membranes were washed with PBST and then incubated with the appropriate secondary antibody [Goat anti-mouse IRDye680CW (LICOR) for mouse serum and flavivirus antibody; and Goat anti-human IRDye800CW (LICOR) for RM Sera] at 1:15,000 dilution for mouse sera for 1 hour at room temperature. After washing, the membranes were imaged on the Odyssey infrared imager (LI-COR).

For the immunofluorescence assay, HeLa or Vero cells were grown on coverslips and transfected with 5 μg of Zika preM+Env vaccine. Two days after transfection, the cells were fixed with 4% PFA for 15 min. Non-specific binding was then blocked with Normal Goat Serum diluted in PBS at room temperature for 1 hour. The slides were then washed in PBS for 5 min and subsequently incubated with sera from immunized mice or RM at a 1:100 dilution overnight at 4° C. Slides were washed as described above and incubated with appropriate secondary antibody [Goat anti-mouse IgG-AF488 (Sigma) for mouse serum and Goat anti-human IgG-AF488 for RM serum] at 1:200 dilution at room temperature for 1 hour. After washing, Flouroshield Mounting media with DAPI (Abcam) was added to stain the nuclei of all cells. After which, coverslips were mounted and the slides were observed under a microscope (EVOS Cell Imaging Systems; Life Technologies) (Muthumani et al., 2015, Sci Trans Med 7:301ra132). Additionally, Vero, SK-N-SH, or U87-MB cells were grown on four chamber tissue culture treated glass slides (Falcon cat #354114) and infected with MR766 ZV at an MOI of 0.01 for 4-6 days and then stained as described.

Splenocyte and PBMC Isolation

Single-cell suspensions of splenocytes were prepared from all mice. Briefly, spleens from mice were collected individually in 5 ml of RPMI 1640 supplemented with 10% FBS (R10), then processed with a Stomacher 80 paddle blender (A.J. Seward and Co. Ltd.) for 30 seconds on high speed. Processed spleen samples were filtered through 45-mm nylon filters and then centrifuged at 1500 rpm for 10 min at 4° C. Cell pellets were resuspended in 5 ml of ACK (ammonium-chloride-potassium) lysis buffer (Life Technologies) for 5 min at room temperature, and PBS was then added to stop the reaction. Samples were again centrifuged at 1500 rpm for 10 min at 4° C. Cell pellets were resuspended in R10 at a concentration of $1 \times 10^7$ cells/ml and then passed through a 45-mm nylon filter before use in ELISpot assay and flow cytometric analysis (Muthumani et al., 2015, Sci Trans Med 7:301ra132). For RM, blood (20 ml at each time point) was collected in EDTA tubes, and peripheral blood mononuclear cells (PBMCs) were isolated using a standard Ficoll-Hypaque procedure with Accuspin tubes (Sigma-Aldrich, St. Louis, MO).

ELISpot Assay

Briefly, 96-well ELISpot plates (Millipore) were coated with anti-mouse IFN-γ capture Ab (R&D Systems) and incubated overnight at 4° C. The following day, plates were washed with PBS and blocked for 2 h with PBST+1% BSA. Two hundred thousand splenocytes from the pZV-prM+Env-immunized mice were added to each well and incubated overnight at 37° C. in 5% $CO_2$ in the presence of media alone (negative control), media with PMA/Ionomycin (positive control), or media with peptide pools (1 µg/ml) consisting of 15-mers overlapping by 9 amino acids and spanning the length of the Zika envelope protein (Genscript). After 24 h, the cells were washed and then incubated overnight at 4° C. with biotinylated anti-mouse IFN-γ Ab (R&D Systems). Streptavidin-alkaline phosphatase (R&D Systems) was added to each well after washing and then incubated for 2 h at room temperature. The plate was washed, and then 5-bromo-4-chloro-3'-indolylphosphate p-toluidine salt and nitro blue tetrazolium chloride (chromogen color reagent; R&D Systems) was added. Lastly, the plates were rinsed with distilled water, dried at room temperature, and spot forming units were quantified by an automated ELISpot reader (CTL Limited), and the raw values were normalized to SFU per million splenocytes. For RM samples, the ELISPOTPRO for monkey IFN-γ kit (MABTECH) was used as described by the manufacturer, two hundred thousand PBMC's were stimulated with peptide pools, and plates were washed and spots were developed and counted as described before (Muthumani et al., 2015, Sci Trans Med 7:301ra132; Mallilankaraman et al., 12011, PLoS Negl Trop Dis 5:e928).

Humoral Immune Response: Antibody-Binding ELISA

An enzyme-linked immunosorbent assay (ELISA) was used to determine the titers of mouse and RM sera as previously described (Muthumani et al., 2015, Sci Trans Med 7:301ra132). Briefly, 1 µg/ml of purified Zika Envelope protein was used to coat 96-well microtiter plates (Nalgene Nunc International, Naperville, IL) at 4° C. overnight. After blocking with 10% FBS in PBS for at least an hour, plates were washed 4 times with 0.05% PBST (Tween20 in PBS). Serum samples from immunized mice and RMs were serially diluted in 1% FBS, 0.2% PBST, added to the plates, then incubated for 1 h at room temperature. Plates were again washed 4 times in 0.05% PBST then incubated with HRP-conjugated anti-mouse IgG (Sigma) at 1:35000 dilution for mouse sera for 1 h at room temperature. For RM sera, anti-monkey IgG HRP (Southern Biotech) was used at 1:5000 dilutions for 1 h at room temperature. Bound enzyme was detected by adding SIGMAFAST™ OPD (o-Phenylenediamine dihydrochloride) tablets according to the manufacturer's instructions (Sigma Aldrich). The reaction was stopped after 15 minutes with the addition of 1N $H_2SO_4$. Plates were then read at an optical density of 450 nm. All mouse serum and RM serum samples were assayed in duplicate. Endpoint titers were determined using the method described by Frey et al (Frey et al., 1998, J Immunol Methods 221:35-41).

Neutralization ($PRNT_{50}$) Assay

The plaque-reduction neutralization test (PRNT) involving MR766 and Vero cells was described previously (Sun et al., 2006, J Infect Dis 193:1658-65). Briefly, the mouse or RM sera was serially diluted in serum free DMEM (1:10 to 1:1280) and incubated with an equal volume of MR766 Zika virus (100 pfu) at 37° C. for two hours. Mixtures were added to confluent layers of Vero cells and left at 37° C. for adsorption for two hours. An 2×DMEM media:soft-agar (1:1) overlay was added over cells and plate was incubated 5 days at 37° C. Agar overlay was removed from wells and cells were fixed with 4% paraformaldehyde, washed with 1×PBS, stained with crystal violet solution, washed with 1×PBS, and plates left to dry. Plaques in assays done in 24 well plates were counted manually. Plaques in assays done in 96 well plates were scanned with an automated Immunospot reader (CTL Limited), and plaques in sample wells as well as plaques in negative control (DMEM only) and positive control (100 pfu MR766 Zika virus only) were counted using the automated software provided with the ELISpot Reader. Percent plaque reduction was calculated as follows: % reduction=100×[1−(average number of plaques for each dilution/average number of plaques in positive control wells)]. GraphPad Prism software was used to perform non-linear regression analysis of % plaque reduction vs. a log transformation of each individual serum dilution to facilitate linear interpolation of actual 50% PRNT titers at peak post vaccination response. The medians and interquartile ranges at 50% neutralization were calculated for each neutralization target overall and by vaccine treatment group; the geometric mean titers were also calculated. Titers represent the reciprocal of the highest dilution resulting in a 50% reduction in the number of plaques.

Flow Cytometry and Intracellular Cytokine Staining (ICS) Assay

Splenocytes were added to a 96-well plate (2×106/well) and were stimulated with ZikapreM and Envelope pooled peptides for 5 hours at 37° C./5% $CO_2$ in the presence of Protein Transport Inhibitor Cocktail (Brefeldin A and Monensin) (eBioscience). The Cell Stimulation Cocktail (plus protein transport inhibitors) (phorbol 12-myristate 13-acetate (PMA), ionomycin, brefeldin A and monensin) (eBioscience) was used as a positive control and R10 media as negative control. All cells were then stained for surface and intracellular proteins as described by the manufacturer's instructions (BD, San Diego, CA). Briefly, the cells were washed in FACS buffer (PBS containing 0.1% sodium azide and 1% FCS) before surface staining with flourochrome-conjugated antibodies. Cells were washed with FACS buffer, fixed and permeabilized using the BD Cytofix/Ctyoperm™ (BD, San Diego, CA, USA) according to the manufacturer's protocol followed by intracellular staining. The following antibodies were used for surface staining: LIVE/DEAD Fixable Violet Dead Cell stain kit (Invitrogen), CD19 (V450; clone 1D3; BD Biosciences) CD4 (FITC; clone RM4-5; ebioscience), CD8 (APC-Cy7; clone 53-6.7; BD Biosciences); CD44 (BV711; clone IM7; Biolegend). For intracellular staining the following antibodies were used: IFN-γ (APC; clone XMG1.2; Biolegend), TNF-α (PE; clone MP6-XT22; ebioscience), CD3 (PerCP/Cy5.5; clone 145-2C11; Biolegend); IL-2 (PeCy7; clone JES6-5F14; ebioscience). All data was collected using a LSRII flow cytometer (BD Biosciences) and analyzed using FlowJo software (Tree Star, Ashland, OR).

Statistical Analysis

Graphpad, Prism 4 (Graphpad software, Inc. San Diego, CA) was utilized for statistical analysis. Log 10 transformations were applied to end point binding ELISA titers and whole virus PRNT50 titers The results of these experiments are now described.

Construction of the ZIKV-prME Consensus DNA Vaccine

A consensus sequence of Zika prM (precursor membrane) and E (envelope) genes (ZIKV-prME) was generated using prM and E sequences from various ZIKA isolated between 1952 and 2015 that caused infection in humans (FIG. 16A). The ZIKA-prME consensus sequence was cloned into the pVax1 vector after additional modifications and optimizations were made to improve its in vivo expression including the addition of a highly efficient immunoglobulin E (IgE) leader peptide sequence (FIG. 16B). Endonuclease restriction digest and gene sequencing were used to validate the final vaccine plasmid (FIG. 16C). Expression of the ZIKA-prME protein off the plasmid was confirmed by performing Western analysis and indirect immunofluorescence assay from vaccine-transfected 293T cells at 48 hours post84 transfection (FIG. 16D and FIG. 16E).

Zika-pME DNA Vaccine Induces Antigen-Specific T Cell or Functional Humoral Responses in Mice The ability of the ZIKA-prME plasmid vaccine to induce cellular immune responses was evaluated. Groups of five C57/BL6 mice were immunized with either control plasmid backbone (pVax1) or the ZIKA-prME plasmid vaccine three times at 2-week intervals by intramuscular injection followed by electroporation (EP) at the 92 site of delivery as described (Muthumani et al., 2015, Sci Trans Med 7:301ra132). Animals were sacrificed one week after their third injection and bulk splenocytes harvested from each animal were evaluated in standard enzyme-linked immunospot assays for their ability to secrete interferon-γ after ex-vivo exposure to peptide pools encompassing ZIKA-Env. The assay results show that splenocytes from ZIKA-prME immunized mice produced clear cellular immune response after stimulation with multiple ZIKA-Env peptide pools (FIG. 17A). The region(s) of ZIKA-Env that elicited the strongest cellular response(s) were evaluated by mapping analysis ELISpot in a matrix format using 22 peptide pools consisting of 15-mers (overlapping by 11 amino acids) spanning the entire ZIKA-prME protein. As seen in FIG. 17B, several pools induced elevated T cell responses, but peptide pool 15 induced the highest SFU per $10^6$ responses. The mapping data revealed one dominant prME epitopes 'IRCIGVSNRDFVEGM (SEQ ID NO: 18)' for the sequences. The dominant peptides listed were confirmed to contain one H2-db restricted epitope by using Immune Epitope Database analysis resource IDEP consensus tool, suggesting effective processing of this antigen.

Further evaluation of the cellular immunogenicity of the ZIKA-prME vaccine entailed the determination of the polyfunctional properties of CD8+ T cells collected one week after the final immunization. The results show that the ZIKA-prME vaccine increased the proportion of bifunctional vaccine-specific T cells expressing tumor necrosis factor-α (TNF-α) and IFN-γ (FIG. 17C). Importantly, ZIKA-prME vaccination exhibited a strong ability to expand T-cell functionality. Further vaccine studies were performed with plasmids 115 encoding the prME sequence of either a recently identified Brazilian ZIKA strain or of the original MR766 ZIKA strain for comparative studies. Induction of cellular immune responses in mice immunized with either plasmid was measured one week after the third injection by IFN-γ ELISpot after stimulating splenocytes with the same ZIKA-preME peptide pools as used in FIG. 17A. The result shows that the T cell responses and antibody responses induced by the novel consensus ZIKA-prME DNA vaccine construct were at least two fold higher than those generated by either of these two non-consensus plasmid vaccines (FIG. 18A and FIG. 18B). Detailed mapping analysis of the cellular responses induced by either the Brazilian or MR766 prME vaccine revealed that both also induced their most significant cellular response to the dominant Env-specific CTL epitope identified in FIG. 17B for the consensus ZIKA-prME plasmid (data not shown). Overall the consensus immunogen appeared consistently more robust in these assays and was studied further.

The ability of the consensus ZIKA-prME vaccine to induce humoral immune responses in mice was evaluated. Groups of C57/BL6 mice were immunized three times at 2-week intervals with 25 μg of either empty control plasmid or consensus ZIKAprME vaccine plasmid by i.m. injection followed by EP. Serum was obtained from each injected mice at day 0 (prior to first immunization), day 14 (two weeks after the first immunization), day 21 (one week after the second immunization) and day 35 (one week after the third immunization). Each sera collected was tested by ELISA for ZIKA specific IgG responses using immobilized rZIKA-Env as the capture antigen. A significant increase in anti-ZIKA-specific IgG was observed on day 21 with a further boost in sera IgG levels seen in day 35 sera (FIG. 19A). Day 138 60 sera from vaccinated animals show that the high antibody responses seen in day 35 sera were maintained long-term following the final boost. Most importantly, sera from vaccinated mice contained very high levels of antibody as indicated by the endpoint titers (FIG. 19B). Additional assessment of the specificity of the vaccine-induced antibodies was performed by screening day 35 pooled-sera for its ability to detect rZIKA-E by Western analysis (FIG. 19C) and to stain Zika-infected cells by an immunofluorescent assay (FIG. 19D). Results from both of these analyses confirmed specificity.

Furthermore, ZIKA-specific binding antibody responses were also assessed in mice immunized with plasmids encoding the prME sequences from a Brazilian strain and the MR766 strain described above. Day 35 sera from sham- or vaccine-immunized mice were analyzed in ELISA for binding to rZIKA-E. This analysis indicates that both plasmids induced significant antibody binding (FIG. 18C and FIG. 18D) and that immunization with the consensus ZIKA-prME DNA vaccine generates a good humoral response with increased affinity to heterologous ZIKA Envelopes.

A plaque reduction neutralization test (PRNT) assay was performed on day 35 pooled-sera from mice immunized three times with either empty pVax1, consensus ZIKA-prME plasmid vaccine, or a consensus ZIKA-capsid plasmid vaccine using a method adapted from a previously described technique for analyzing DV, WNV and other flaviviruses. As shown in FIG. 19E, anti-ZIKA reciprocal PRNT50 dilution titers after the third vaccination were significantly higher in mice that 160 received the ZIKA-prME vaccine than in those that received the ZIKA-Capsid DNA vaccine or the control DNA pVax1. Neutralizing antibodies induced by the ZIKA-prME vaccine used in this experiment had a PRNT50 titer=456. Representative photographs of viral plaques are shown in the bottom for 1:100 dilutions of sera.

Cellular and Humoral Responses Elicited by the ZIKA-prME DNA Vaccine in Non-Human Primates NHPs were immunized by intradermal (ID) immunization followed by electroporation based on previous studies showing that this method may enhance antigen-specific humoral immune responses by DNA vaccines. Rhesus macaque (RM; n=5/group) were administered 2.0 mg of vaccine plasmid ID with EP, and sera and PBMCs were collected from RM at day 0 (pre-immunization prior to first immunization), week 2 (2 weeks post first immunization), week 6 (2 weeks post second immunization). To measure vaccine-induced cellular immune responses, ELISpot analysis was performed on Wk6 PBMCs ex vivo stimulated with the ZIKA-E peptide pools used in FIG. 17A. The results show that the ZIKA prME immunization boosted anti-Zika T cell responses in all RM and broadened their antigen recognition compared to responses in pre-immune sera (FIG. 20A).

Specific anti-Zika virus antibody responses in sera 181 from ID+EP vaccinated RM were assessed by ELISA. Following primary vaccination, ZIKA-Env-specific binding antibodies were detectable in RM two weeks after the first immunization with further boosting with a subsequent immunization (FIG. 20B). Sera from vaccinated RM from the same post-immunization time point were diluted to study end points titers and assayed again the rZIKA-Env (FIG. 20C). ELISA results were confirmed by Western analysis using pooled RM sera from the vaccinated group (FIG. 20D). Further, sera from immunized RM were also able to recognize ZIKA-MR766-infected Vero cells in an immunoflourescence assay (FIG. 20E). Next, it was attempted to detect the neutralization antibody (nAb) response in the sera from ZIKA-immunized RM. The PRNT50 (inverse of the serum dilution at which 50% of the control ZIKA infection was inhibited) was used to test for NAb activity and was performed on each individual immunized animal. Samples with an antibody titer <10, which were the limit of the detection of the assay, were assigned for each group of animals. Interestingly, ZIKA-prME immunized monkey had titers range from 161 to 1380 (average 501±224) (FIG. 21A).

The ability of the NHP immune sera to block infection in ZIKA infected neuroblastoma cells (SK-N-SH cells) and neural progenitor cells (U-87MG) of importance. Cell lines with MR766 or PR209 with control or vaccine sera and analyzed for infection at 24 hours. Sera from vaccinated RM inhibited either virus in both cell lines post infection (multiplicity of infection of 1.0) (FIG. 21B and FIG. 21C). These data support the effectiveness of sera from ZIKA-prME DNA vaccinated RM to inhibit ZIKA infection.

ZIKA-Specific Functional Immune Responses and Protection Against Zika Virus in Mice Lacking the Receptor for Type I Interferon (IFNAR), Immunized with the ZIKAprME DNA Vaccine Mechanisms of ZIKA-induced disease and immunity are poorly defined, and the protective versus the hypothetical pathogenic nature of the immune response to ZIKA infection is as yet unclear. Most strains of mice are resistant to ZIKA infection, however, mice lacking IFN-α/β receptor (IFNAR) were found to be susceptible to infection and disease, most succumbing within 6-7 days of challenge 16. The ability of the consensus ZIKA-prME plasmid vaccine to induce cellular and humoral immune responses in this mouse strain was investigated. Groups of IFNAR mice were immunized 3 times at 2-week intervals with empty control plasmid or with the consensus ZIKA-prME plasmid by EP. Serum was collected from immunized mice at days 0, 14, 21, and 35 and splenocytes were harvested from mice one week following the final immunization. Splenocytes from vaccine-immunized IFNAR mice produced a clear cellular immune response as indicated by levels of SFU per 106 cells in an ELISpot assay (FIG. 22A). Results from ELISAs using rZIKA-Env as a capture antigen show that animals had detectable anti-ZIKA serum IgG by day 14 and these levels were boosted at subsequent collection times (FIG. 22B). Sera from vaccinated mice contained significant levels of antibody as indicated by the endpoint titers (FIG. 22B). The results indicate that IFNAR mice immunized with the consensus ZIKA-prME vaccine are capable anti-ZIKA cellular and humoral immune responses supporting further study for vaccine protection in this potential challenge model.

In exploratory studies, IFNAR mice were challenged with $1 \times 10^6$ PFU of the PR209 isolate, administered subcutaneously (s.c.); intraperitoneal (i.v); intracranial (i.c.) and intravenously (i.v). After challenge, all animals were monitored for clinical signs including routine body weight, recording body temperature measurement well as other signs of a moribund condition such as hind limb weakness and paralysis. No change in the general appearance of the mice was observed during the first 2 days after inoculation. However, after the third day, all four routes of infection showed reduced activity, decreased mobility, hunched posture; accompanied by hind limb weakness and water intake and obvious weight loss. Animals regardless of challenge site succumbed to the infection between day 6 and day 8 and this challenge dose was utilized in subsequent studies.

Two groups of vaccinated animals (10 per group) or two sets of pVax1 immunized controls, were vaccinated 1× on day 0 and 1× on day 14 and challenged on day 21 with either $1 \times 10^6$ PFU or $2 \times 10^6$ PFU of PR209 (FIG. 23B and FIG. 23C). 100% of the vaccinated animals survived while only 30% of the $1 \times 10^6$ PFU or 10% of the $2 \times 10^6$ PFU challenged controls survived. Next, a group of animals was immunized 1× and challenged them on Day 14 post immunization. 100% of these animals survived, while 10% of the control animals survived. All mice vaccinated with ZIKA-prME once and then challenged with Zika virus were protected from the lethal challenge (FIG. 23A). In all challenges, vaccinated animals also did not exhibit symptoms of disease and were protected from weight loss (FIG. 23D). Infection of control mice with Zika virus produced a marked decrease in body weight often combined to decreased mobility, hunched posture, hind limb knuckle-walking and/or paralysis both hind limbs with significant mortality (FIG. 23E and FIG. 23F). Taken together, these data illustrate that ZV-prME DNA vaccine mediated immune responses that protect mice against Zika challenge.

In the present studies, humoral and cellular responses using prME as antigen produced from a DNA-based vaccine plus electroporation were documented in rodents and non-human primates. The optimized enhanced DNA vaccine technology by EP delivery approach was effective at stimulating robust and broad immune responses and a single immunization induced immunity that was protective from disease and mortality in IFNAR mice. This study supports the concept that protective immunity can be generated using a flexible and rapidly clinically implementable DNA vaccination strategy against this serious emerging viral infection.

Example 3: In Vivo Protection Against ZIKV Infection and Pathogenesis Through Passive Antibody Transfer and Active Immunization with a prMEnv DNA Vaccine In this study, novel, synthetic, DNA vaccine targeting the pre-membrane+envelope proteins (prMEnv) of ZIKV generated and evaluated for in vivo efficacy. Following initial in vitro development and evaluation studies of the plasmid construct, mice and non-human primates were immunized with this prMEnv DNA-based immunogen through electroporation-mediated enhanced DNA delivery. Vaccinated animals were found to generate antigen-specific cellular and humoral immunity and neutralization activity. In mice lacking receptors for interferon (IFN)-α/β (designated IFNAR$^{-/-}$) immunization with this DNA vaccine induced, following in vivo viral challenge, 100% protection against infection-associated weight loss or death in addition to preventing viral pathology in brain tissue. In addition, passive transfer of non-human primate anti-ZIKV immune serum protected IFNAR$^{-/-}$ mice against subsequent viral challenge. This initial study of this ZIKV vaccine in a pathogenic mouse model supports the importance of immune responses targeting prME in ZIKV infection and suggests that additional research on this vaccine approach may have relevance for ZIKV control in humans.

The materials and methods are now described.

Cells, Virus and Animals

Human embryonic kidney 293T (American Type Culture Collection (ATCC) #CRL-N268, Manassas, VA, USA) and Vero CCL-81 (ATCC #CCL-81) cells were maintained in DMEM (Dulbecco's modified Eagle's medium; Gibco-Q3 Invitrogen) supplemented with 10% fetal bovine serum (FBS) and 1% penicillin and streptomycin and passaged upon confluence. Both ZIKV virus strains MR766 (a kind gift from Dr Susan Weiss) and PR209 (Bioqual, MD) were amplified in Vero cells and stocks were titred by standard plaque assay on Vero cells. Five- to six-week-old female C57BL/6 (The Jackson Laboratory) and IFNAR$^{-/-}$ (MMRRC repository—The Jackson Laboratory) mice were housed and treated/vaccinated in a temperature-controlled, light-cycled facility in accordance with the National Institutes of Health, Wistar and the Public Health Agency of Canada IACUC (Institutional Animal Care and Use Committee) guidelines.

The RMs were housed and treated/vaccinated at Bioqual, MD, USA. This study was carried out in strict accordance with the recommendations described in the Guide for the Care and Use of Laboratory Animals of the NIH, the Office of Animal Welfare, and the U.S. Department of Agriculture. All animal immunization work was approved by the Bioqual Animal Care and Use Committee (IACUC). Bioqual is accredited by the American Association for Accreditation of Laboratory Animal Care. All the procedures were carried out under ketamine anesthesia by trained personnel under the supervision of veterinary staff, and all the efforts were made to protect the welfare of the animals and to minimize animal suffering in accordance with the 'Weatherall report for the use of non-human primates' recommendations. The animals were housed in adjoining individual primate cages allowing social interactions, under controlled conditions of humidity, temperature and light (12 h light/12 h dark cycles). Food and water were available ad libitum. The animals were monitored twice daily and fed commercial monkey chow, treats and fruits twice daily by trained personnel.

Construction of ZIKV-prME DNA Vaccine

The ZIKV-prME plasmid DNA constructs encodes full-length precursor of membrane (prM) plus envelope (E) and Capsid proteins were synthesized. A consensus strategy was used and the consensus sequences were determined by the alignment of current ZIKV prME protein sequences. The vaccine insert was genetically optimized (i.e., codon and RNA optimization) for enhanced expression in humans and an IgE leader sequence was added to facilitate expression. The construct was synthesized commercially (Genscript, NJ, USA), and then subcloned into a modified pVax1 expression vector under the control of the cytomegalovirus immediate-early promoter as described before (Muthumani et al., 2016, Sci Transl Med 7:301ra132). The final construct is named ZIKV-prME vaccine and the control plasmid backbone is pVax1. In addition, a number of other matched DNA constructs encoding the prM and E genes from MR766 (DQ859059.1) and a 2016 Brazilin (AMA12084.1) outbreak strain were also designed, for further evaluation. Large-scale amplifications of DNA constructs were carried out by Inovio Pharmaceuticals Inc. (Plymouth Meeting, PA, USA) and purified plasmid DNA was formulated in water for immunizations. The size of the DNA inserts was confirmed via agarose gel electrophoresis. Phylogenetic analysis was performed by multiple alignment with ClustalW using MEGA version 5 software (Muthumani et al., 2016, Sci Transl Med 7:301ra132).

DNA Immunizations and Electroporation-Mediated Delivery Enhancement

Female C57BL/6 mice (6-8 weeks old) and IFNAR$^{-/-}$ mice (5-6 weeks old) were immunized with 25 µg of DNA in a total volume of 20 or 30 µl of water delivered into the tibialis anterior muscle with in vivo electroporation delivery. In vivo electroporation was delivered with the CELLECTRA adaptive constant current electroporation device (Inovio Pharmaceuticals) at the same site immediately following DNA injection. A three-pronged CELLECTRA minimally invasive device was inserted ~2 mm into the muscle. Square-wave pulses were delivered through a triangular three-electrode array consisting of 26-gauge solid stainless steel electrodes and two constant current pulses of 0.1 Amps were delivered for 52 µs/pulse separated by a 1 s delay. Further protocols for the use of electroporation have been previously described in detail (Flingai et al., 2015, Sci Rep 5:12616). The mice were immunized three times at 2-week intervals and killed 1 week after the final immunization. The blood was collected after each immunization for the analysis of cellular and humoral immune responses (Muthumani et al., 2016, Sci Transl Med 7:301ra132). Rhesus macaque immunogenicity studies: five rhesus macaques were immunized intradermally at two sites two times at 5-week intervals with 2 mg ZIKV-prME vaccine. Electroporation was delivered immediately using the same device described for mouse immunizations.

Western Blot Analysis

For in vitro expression studies, transfections were performed using the GeneJammer reagent, following the manufacturer's protocols (Agilent). Briefly, the cells were grown to 50% confluence in a 35 mm dish and transfected with 1 µg of ZIKV-prME vaccine. The cells were collected 2 days after transfection, washed twice with PBS and lysed with cell lysis buffer (Cell Signaling Technology). Western Blot was used to verify the expression of the ZIKV-prME protein from the harvested cell lysate and the immune specificity of the mouse and RM serum through the use of either anti- Flavivirus or immune sera from the ZIKV-prME vaccinated mice, as described previously (Muthumani et al., 2016, Sci Transl Med 7:301ra132). In brief, 3-12% Bis-Tris NuPAGE gels (Life Technologies) were loaded with 5 μg or 1 μg of ZIKV envelope recombinant protein (rZIKV-E); transfected cell lysates or supernatant and the Odyssey protein Molecular Weight Marker (Product #928-40000). The gels were run at 200 V for 50 min in MOPS buffer. The proteins were transferred onto nitrocellulose membranes using the iBlot 2 Gel Transfer Device (Life Technologies). The membranes were blocked in PBS Odyssey blocking buffer (LI-COR Biosciences) for 1 h at room temperature. To detect vaccine expression, the anti-Flavivirus group antigen (MAB10216-Clone D1-4G2-4-15) antibody was diluted 1:500 and the immune serum from mice and RM was diluted 1:50 in Odyssey blocking buffer with 0.2% Tween 20 (Bio-Rad) and incubated with the membranes overnight at 4° C. The membranes were washed with PBST and then incubated with the appropriate secondary antibody (goat anti-mouse IRDye680CW; LI-COR Biosciences) for mouse serum and flavivirus antibody; and goat anti-human IRDye800CW (LI-COR Biosciences) for RM sera at 1:15,000 dilution for mouse sera for 1 h at room temperature. After washing, the membranes were imaged on the Odyssey infrared imager (LI-COR Biosciences).

Immunofluorescence Assays

For the immunofluorescence assay, the cells were grown on coverslips and transfected with 5 μg of ZIKV-prME vaccine. Two days after transfection, the cells were fixed with 4% paraformaldehyde for 15 min. Nonspecific binding was then blocked with normal goat serum diluted in PBS at room temperature for 1 h. The slides were then washed in PBS for 5 min and subsequently incubated with sera from immunized mice or RM at a 1:100 dilutions overnight at 4° C. The slides were washed as described above and incubated with appropriate secondary antibody (goat anti-mouse IgGAF488; for mouse serum and goat anti-human IgG-AF488 for RM serum; Sigma) at 1:200 dilutions at room temperature for 1 h. After washing, Flouroshield mounting media with DAPI (Abcam) was added to stain the nuclei of all cells. After which, coverslips were mounted and the slides were observed under a microscope (EVOS Cell Imaging Systems; Life Technologies) (Muthumani et al., 2016, Sci Transl Med 7:301ra132). In addition, Vero, SK-N-SH or U87-MB cells were grown on four-chamber tissue culture treated glass slides and infected at MOI of 0.01 with ZIKV-MR766 or PR209 that were preincubated with/without RM immune sera (1:200), and stained at 4 days post ZIKV infection using pan flavirus antibody as described (Rossi et al., 2016, J Rop Med Hyg 94:1362-9).

Histopathology Analysis

For histopathology, formalin-fixed, paraffin-embedded brain tissue was sectioned into 5 μm thick sagittal sections, placed on Superfrost microscope slides (Fisher Scientific) and backed at 37° C. overnight. The sections were deparaffinised using two changes of xylene and rehydrated by immersing in 100%, 90% and then 70% ethanol. The sections were stained for nuclear structures using Harris haematoxylin (Surgipath) for 2 min followed by differentiation in 1% acid alcohol (Surgipath) and treatment with Scott's tap water for 2 min. Subsequently, the sections were counterstained for cytoplasmic structures using eosin (Surgipath) for 2 min. The slides were dehydrated with 70%, 90% and 100% ethanol, cleared in xylene and mounted using Permount (Fisher Scientific).

Splenocyte and PBMC Isolation

Single-cell suspensions of splenocytes were prepared from all the mice. Briefly, the spleens from mice were collected individually in 5 ml of RPMI 1640 supplemented with 10% FBS (R10), then processed with a Stomacher 80 paddle blender (A.J. Seward and Co. Ltd.) for 30 s on high speed. The processed spleen samples were filtered through 45 mm nylon filters and then centrifuged at 1,500 g for 10 min at 4° C. The cell pellets were resuspended in 5 ml of ACK (ammonium-chloride-potassium) lysis buffer (Life Technologies) for 5 min at room temperature, and PBS was then added to stop the reaction. The samples were again centrifuged at 1,500 g for 10 min at 4° C. The cell pellets were resuspended in R10 and then passed through a 45 mm nylon filter before use in ELISpot assay and flow cytometric analysis (Muthumani et al., 2016, Sci Transl Med 7:301ra132). For RM, blood (20 ml at each time point) was collected in EDTA tubes and the PBMCs were isolated using a standard Ficoll-hypaque procedure with Accuspin tubes (Sigma-Aldrich, St. Louis, MO, USA). Five millitres of blood was also collected into sera tubes at each time point for sera isolation.

Flow Cytometry and Intracellular Cytokine Staining Assay

The splenocytes were added to a 96-well plate ($2 \times 10^6$/well) and were stimulated with ZIKV-prME pooled peptides for 5 h at 37° C./5% CO2 in the presence of Protein Transport Inhibitor Cocktail (brefeldin A and monensin; eBioscience). The cell stimulation cocktail (plus protein transport inhibitors; PMA (phorbol 12-myristate 13-acetate), ionomycin, brefeldin A and monensin; eBioscience) was used as a positive control and R10 media as the negative control. All the cells were then stained for surface and intracellular proteins as described by the manufacturer's instructions (BD Biosciences, San Diego, CA, USA). Briefly, the cells were washed in FACS buffer (PBS containing 0.1% sodium azide and 1% FBS) before surface staining with flourochrome-conjugated antibodies. The cells were washed with FACS buffer, fixed and permeabilised using the BD Cytofix/Ctyoperm™ (BD Biosciences) according to the manufacturer's protocol followed by intracellular staining. The following antibodies were used for surface staining: LIVE/DEAD Fixable Violet Dead Cell stain kit (Invitrogen), CD19 (V450; clone 1D3; BD Biosciences), CD4 (FITC; clone RM4-5; eBioscience), CD8 (APC-Cy7; clone 53-6.7; BD Biosciences); CD44 (BV711; clone IM7; BioLegend). For intracellular staining, the following antibodies were used: IFN-γ (APC; clone XMG1.2; BioLegend), TNF-α (PE; clone MP6-XT22; eBioscience), CD3 (PerCP/Cy5.5; clone 145-2C11; BioLegend); IL-2 (PeCy7; clone JES6-5F14; eBioscience). All the data were collected using a LSRII flow cytometer (BD Biosciences) and analyzed using FlowJo software (Tree Star, Ashland, OR, USA).

ELISpot Assay

Briefly, 96-well ELISpot plates (Millipore) were coated with anti-mouse IFN-γ capture Ab (R&D Systems) and incubated overnight at 4° C. The following day, the plates were washed with PBS and blocked for 2 h with PBST+1% BSA. Two hundred thousand splenocytes from immunized mice were added to each well and incubated overnight at 37° C. in 5% $CO_2$ in the presence of media alone (negative control), media with PMA/ionomycin (positive control) or media with peptide pools (1 μg/ml) consisting of 15-mers overlapping by nine amino acids and spanning the length of the ZIKV prME protein (Genscript). After 24 h, the cells were washed and then incubated overnight at 4° C. with biotinylated anti-mouse IFN-γ Ab (R&D Systems). Streptavidin-alkaline phosphatase (R&D Systems) was added to each well after washing and then incubated for 2 h at room temperature. The plate was washed, and then 5-bromo-4-chloro-3'-indolylphosphate p-toluidine salt and nitro blue tetrazolium chloride (chromogen colour reagent; R&D Systems) was added. Last, the plates were rinsed with distilled water, dried at room temperature and SFU were quantified by an automated ELISpot reader (CTL Limited), and the raw values were normalised to SFU per million splenocytes. For RM samples, the ELISPOT$^{PRO}$ for monkey IFN-γ kit (MABTECH) was used as described by the manufacturer; two hundred thousand PBMCs were stimulated with peptide pools; and the plates were washed and spots were developed and counted as described before (Muthumani et al., 2016, Sci Transl Med 7:301ra132).

Humoral Immune Response: Antibody-Binding ELISA

An ELISA was used to determine the titers of mouse and RM sera as previously described (Muthumani et al., 2016, Sci Transl Med 7:301ra132). Briefly, 1 μg of purified rZIKV-E protein was used to coat 96-well microtiter plates (Nalgene Nunc International, Naperville, IL, USA) at 4° C. overnight. After blocking with 10% FBS in PBS for at least an hour, the plates were washed four times with 0.05% PBST (Tween20 in PBS). Serum samples from immunized mice and RMs were serially diluted in 1% FBS, added to the plates, then incubated for 1 h at room temperature. The plates were again washed four times in 0.05% PBST, then incubated with HRP-conjugated anti-mouse IgG (Sigma) at a 1:35,000 dilution for mouse sera for 1 h at room temperature. For RM sera, anti-monkey IgG HRP (Southern Biotech) was used at a 1:5,000 dilutions for 1 h at room temperature. The bound enzyme was detected by adding SIGMAFAST OPD (o-phenylenediamine dihydrochloride) substrate solution according to the manufacturer's instructions (Sigma-Aldrich). The reaction was stopped after 15 min with the addition of 1 N $H_2SO_4$. The optical density at 450 nm was read on a Synergy plate reader. All the mouse and RM serum samples were assayed in duplicate. End point titers were determined using the method described previously (Frey et al., 1998, J Immunol Methods 21:35-41).

Neutralization ($PRNT_{50}$) Assay

The PRNT involving MR766 and Vero cells was described previously (Sun et al., 2006, J Infect Dis 193:1658-65). Briefly, heat-inactivated mouse or RM sera were serially diluted in serum-free DMEM (1:10 to 1:1280) and incubated with an equal volume of ZIKV MR766 (100 PFU) at 37° C. for 2 h. The mixtures were added to the confluent layers of Vero cells and left at 37° C. for adsorption for 2 h. A 2×DMEM media:soft-agar (1:1) overlay was added over cells and the plate was incubated for 5 days at 37° C. The agar overlay was removed and the cells were fixed with 4% paraformaldehyde, washed with 1×PBS, stained with crystal violet solution, washed with 1×PBS and the plates were left to dry. The plaques in assays done in 24-well plates were scanned with an automated Immunospot reader (CTL Limited), and the plaques in sample wells and in negative control (DMEM only) and positive control (100 PFU MR766 ZIKV virus only) wells were counted using the automated software provided with the ELISpot reader. The percentage plaque reduction was calculated as follows: % reduction=100×{1− (average number of plaques for each dilution/average number of plaques in positive control wells)}. GraphPad Prism software was used to perform nonlinear regression analysis of % plaque reduction versus a log transformation of each individual serum dilution to facilitate linear interpolation of actual 50% PRNT titers at peak post vaccination response. The medians and interquartile ranges at 50% neutralization were calculated for each neutralization target overall and by vaccine treatment group; the geometric mean titers were also calculated. The titers represent the reciprocal of the highest dilution resulting in a 50% reduction in the number of plaques.

ZIKV Challenge Studies in IFNAR$^{-/-}$ Mice

For the ZIKA challenge studies, IFNAR$^{-/-}$ mice (n=10/group) were immunized once or twice with the ZIKA-prME vaccine or pVax1. The mice were with either 1×10$^6$ PFU or 2×10$^6$ PFU ZIKV-PR209 virus on day 15 (single immunization group) or day 21 one week after the second immunization (two immunization groups). Also, additional groups of IFNAR$^{-/-}$ mice (n=10/group) were immunized once and challenged with 2×10$^6$ PFU ZIKV-PR209 virus on day 15. Post challenge, the animals were weighed and body temperature was measured daily by a subcutaneously located temperature chip. In addition, they were observed for clinical signs of disease twice daily (decreased mobility; hunched posture; hind-limb knuckle walking (partial paralysis), paralysis of one hind limb or both hind limbs) and the blood was drawn for viral load determination. The criteria for killing on welfare grounds consisted of 20% weight loss or paralysis in one or both hind limbs.

Real-Time RT-PCR Assay for Measurement of ZIKV Load

The brains from treated mice were immersed in RNAlater (Ambion) 4° C. for 1 week, then stored at −80° C. The brain tissue was then weighed and homogenized in 600 μl RLT buffer in a 2 ml cryovial using a TissueLyser (Qiagen) with a stainless steel bead for 6 min at 30 cycles/s. Viral RNA was also isolated from blood with the RNeasy Plus mini kit (Qiagen). A ZIKV specific real-time RT-PCR assay was utilized for the detection of viral RNA from subject animals. RNA was reverse transcribed and amplified using the primers ZIKV 835 and ZIKV 911c and probe ZIKV 860FAM with the TaqMan Fast Virus 1-Step Master Mix (Applied Biosystems). A standard curve was generated in parallel for each plate and used for the quantification of viral genome copy numbers. The StepOnePlus Real-Time PCR System (ABI) software version 2.3 was used to calculate the cycle threshold (Ct) values, and a Ct value ≤38 for at least one of the replicates was considered positive, as previously described (Lanciotti et al., 2008, Emerg Infect Dis 14:1232-9). Pre-bleeds were negative in this assay.

Statistical Analysis

Differences in fold increases in antibody titers were compared using Mann-Whitney analysis. Statistical analysis was performed using Graphpad, Prism 4 (Graphpad software, Inc. San Diego, CA, USA). For all the analyses, P<0.05 was considered to be significant. $Log_{10}$ transformations were applied to end point binding ELISA titers and whole-virus $PRNT_{50}$ titers.

The results of these experiments are now described.

Construction of the ZIKV-prME Consensus DNA Vaccine

A consensus sequence of ZIKV prM (precursor membrane) and Env (envelope) genes (ZIKV-prME) was generated using prM and Env sequences from various ZIKV isolated between the years of 1952 and 2015, which caused infection in humans. The ZIKV-prME consensus sequence was cloned into the pVax1 vector after additional modifications and optimizations were made to improve its in vivo expression including the addition of a highly efficient immunoglobulin E (IgE) leader peptide sequence (FIG. 24A). Optimal alignment of ZIKV-envelope sequences was performed using homology models and visualization on Discovery Studio 4.5. Reference models included PDB 5JHM and PDB 5IZ7. Aligned residues corresponding to specific regions on the prME antigen were labelled in the models for visualization purposes (FIG. 24B). The optimized consensus vaccine selections are in general conservative or semi-conservative relative to multiple ZIKV strains analyzed in this study. Structural studies of EDE-specific neutralizing antibodies have revealed that these recognition determinants can be found at a serotype-invariant site at the envelope-dimer interface, which includes the exposed main chain of the fusion loop and two conserved glycan chains (N67- and N153-linked glycans) (Rouvinski et al., 2015, Nature 520: 109-13). These two glycosylation sites are not highly conserved in other flaviviruses. Moreover, ZIKV does not possess the N67-linked glycosylation site, and the N154-linked glycosylation site (equivalent to the N153-linked glycosylation site in dengue) is absent in some of the isolated ZIKV strains. As part of the consensus design, therefore the construct was designed leaving out this glycosylation site. Lack of glycosylation at this site has been correlated with improved binding of EDE1 type broadly neutralizing antibodies (bnAbs) to ZIKV-envelope protein (Rouvinski et al., 2015, Nature 520:109-13).

Subsequent to construction, expression of the ZIKV-prME protein from the plasmid was confirmed by western blot analysis and an indirect immunofluorescence assay. The protein extracts prepared from the cells transiently transfected with ZIKV-prME were analyzed for expression by western blot using panflavivirus antibody (FIG. 24C) and sera collected from ZIKV-prME immunized mice (FIG. 24D). ZIKV-prME expression was further detected by IFA by the staining of 293T cells transfected with ZIKV-prME plasmid at 48 h post transfection with anti-ZIKV-prME specific antibodies (FIG. 24E).

ZIKV-prMEnv DNA Vaccine Induces Antigen-Specific T Cells in C57BL/6 Mice

The ability of the ZIKV-prMEnv plasmid vaccine to induce cellular immune responses was evaluated. Groups of four female C57BL/6 mice were immunized with either the control plasmid backbone (pVax1) or the ZIKV-prME plasmid vaccine three times at 2 week intervals through intramuscular (i.m.) injection followed by electroporation at the site of delivery (FIG. 25A). The animals were killed 1 week after their third injection and bulk splenocytes harvested from each animal were evaluated in ELISpot assays for their ability to secrete interferon-γ (IFN-γ) after ex vivo exposure to peptide pools encompassing ZIKV-prME is included. The assay results show that splenocytes from ZIKV-prME immunized mice produced a cellular immune response after stimulation with multiple ZIKV-E peptide pools (FIG. 25B). The region(s) of ZIKVEnv, which elicited the strongest cellular response(s) were evaluated by ELISpot assay in a matrix format using 22 peptide pools consisting of 15-mers (overlapping by 11 amino acids) spanning the entire ZIKV-prME protein. Several pools demonstrated elevated T cell responses, with peptide pool 15 exhibiting the highest number of spot-forming units (SFU) (FIG. 25C). This matrix mapping analysis revealed a dominant prME epitope, 'IRCIGVSNRDFVEGM (SEQ ID NO:17)' (aa167-181). This peptide was confirmed to contain a H2-db restricted epitope through analysis utilising the Immune Epitope Database Analysis Resource tool, which supports that in this haplotype the antigen is effectively processed.

Further evaluation of the cellular immunogenicity of the ZIKV-prMEnv vaccine entailed the determination of the polyfunctional properties of CD8$^+$ T cells collected 1 week after the final immunization. The results show that the ZIKV-prMEnv vaccination increased the proportion of bifunctional vaccine-specific T cells expressing TNF-α (tumour necrosis factor-α) and IFN-γ. Importantly, ZIKV-prMEnv vaccination exhibited a strong ability to expand T cell functionality (FIG. 25D).

In addition, comparative immune studies were performed with optimized plasmids encoding the prMEnv sequence of either a recently identified Brazilian ZIKV strain or of the original MR766 ZIKV strain. Induction of cellular immune responses in mice immunized with either plasmid was measured 1 week after the third vaccination through IFN-γ ELISpot analysis after stimulating splenocytes with the ZIKV-prMEnv peptide pools. The results illustrate that the T-cell responses induced by the consensus ZIKVprME DNA vaccine construct were consistently higher than those generated by either of these two non-consensus plasmid vaccines (FIG. 31A and FIG. 31B). Detailed mapping analysis of the cellular responses induced by either the Brazilian or MR766 prME vaccines revealed that both vaccines induced significant cellular response against the dominant Env-specific CTL epitope as identified in FIG. 25B and FIG. 25C for the consensus ZIKV-prMEnv plasmid (data not shown). The consensus immunogen consistently induced more robust responses in these T-cell assays at the same dose and was evaluated further in additional assays.

Generation of a ZIKV Recombinant Envelope Protein

At the onset of these studies, there were no available commercial reagents to evaluate specific anti-ZIKV immune responses. Therefore, by necessity, recombinant ZIKV-envelope protein (rZIKV-E) was generated to support the assays performed in this study. To generate this reagent, a consensus ZIKV-Envelope sequence based on the ZIKV-prME vaccine consensus antigen was cloned into a pET30a *Escherichia coli* expression vector (FIG. 32A). The rZIKV-E antigen was produced in *E. coli* cultures, purified using nickel column chromatography and analyzed using SDS-PAGE, which showed overexpressed proteins of the predicted size in lysate from rZIKV-E transfected bacteria that could be detected by western analysis using an anti-His tag antibody (FIG. 32B). The sera from mice immunized with the ZIKV-prME vaccine bound to rZIKV-Env that was used as a capture antigen in an ELISA (enzyme-linked immunosorbent assay; FIG. 32C). A commercial antibody (designated panflavivirus) that reacts to the envelope protein of multiple flaviviruses, also bound to rZIKV-E. Western analysis demonstrated that immune sera from ZIKV-prMEnv immunized mice specifically recognized rZIKV-E (FIG. 32D). These data indicate that the generated rZIKV-E reacted specifically with immune sera from ZIKV-prMEnv vaccinated mice, thus this recombinant protein was used for further immunogenicity studies.

Induction of Functional Humoral Responses in C57BL/6 Mice by the ZIKV-prME DNA Vaccine The ability of the consensus ZIKV-prMEnv vaccine to induce humoral immune responses in mice was evaluated. Groups of four C57BL/6 mice were immunized intramuscularly (i.m.) through electroporation-mediated delivery three times at 2-week intervals with 25 μg of either the empty control pVax1 or the consensus ZIKV-prMEnv vaccine plasmids. The sera were obtained from each immunized mouse and were tested by ELISA for ZIKV-specific IgG responses using immobilized rZIKV-E as the capture antigen. A significant increase in anti-ZIKV-specific IgG was observed on day 21 with a further boost in the sera IgG levels noted on day 35 (FIG. 26A). Day 60 sera from vaccinated animals show that elevated ZIKV-specific antibody responses were maintained long term following the final boost. Most importantly, the sera from vaccinated mice contained very high levels of rZIKV-E-specific antibodies as indicated by the end point titers (FIG. 26B). Additional assessment of the specificity of the vaccine-induced antibodies was performed by screening pooled sera from ZIKVprMEnv plasmid inoculated mice for its ability to detect rZIKV-E (envelope) by western analysis (FIG. 26C) and to stain ZIKV (MR766 strain)-infected cells by an immunofluorescence assay (FIG. 26D). The results from both these analyses confirmed specificity of the vaccine-induced humoral responses.

Furthermore, ZIKV-specific binding antibody responses were also assessed in mice immunized with plasmids encoding the prMEnv sequences from a Brazilian strain and the MR766 strain described above. Day 35 (1 week after third immunization) sera from pVax1- and both non-consensus vaccine-immunized mice were analyzed by ELISA for binding to rZIKV-E. This analysis indicates that both MR766 and Brazil vaccine plasmids induced significant antibody binding, and that immunization with the consensus ZIKV-prME DNA vaccine generates an effective humoral response against rZIKV-E (FIG. 31C and FIG. 31D).

A plaque reduction neutralization test (PRNT) assay was performed on pooled day 35 sera from mice immunized (3×) with either the control pVax1 plasmid, the consensus ZIKV-prMEnv plasmid vaccine or a consensus ZIKV-C (capsid) plasmid vaccine. The PRNT assay used was a method adapted from a previously described technique for analyzing dengue virus, West Nile virus and other flaviviruses (Davis et al., 2001, J Virol 75:4040-7). As shown in FIG. 26E, ZIKV-prME vaccination yielded significant neutralization response with anti-ZIKV reciprocal $PRNT_{50}$ dilution titers (inverse of the serum dilution at which 50% of the control ZIKV infection was inhibited) of 456±5, whereas mice vaccinated with the ZIKV-Cap DNA vaccine demonstrated titers (33±6) that were only minimally over pVax1 control plasmid vaccinated animals (titre=15±2).

Immune Responses and Protection Against ZIKV in Mice Lacking the Type I Interferon Receptor ($IFNAR^{-/-}$) Following Immunization with the ZIKV-prME DNA Vaccine Mechanisms of ZIKV-induced disease and immunity are poorly defined, and the protective versus the hypothetical pathogenic nature of the immune response to ZIKV infection is as yet unclear (Rossi et al., 2016, J Rop Med Hyg 94:1362-9). Most strains of mice are resistant to ZIKV infection, however, mice lacking IFN-α/β receptor ($IFNAR^{-/-}$) were found to be susceptible to infection and disease with most succumbing within 6-7 days post challenge (Lazear et al., 2016, Cell Host Microbe 19:720-30). The ability of the consensus ZIKV-prME plasmid vaccine to induce cellular and humoral immune responses in this mouse strain was investigated. Five to six week old female $IFNAR^{-/-}$ mice (n=4) were immunized i.m., with electroporation-mediated delivery, three times at 2-week intervals with either the control pVax1 plasmid or ZIKV prME vaccine plasmid vaccine. The serum was collected from immunized mice at days 0, 14, 21, and 35, and splenocytes were harvested from mice 1 week following the final immunization (day 35). The splenocytes from vaccine-immunized mice produced a clear cellular immune response as indicated by levels of SFU per $10^6$ cells in an ELISpot assay (FIG. 33A). The results from ELISA analysis, using rZIKV-E as a capture antigen, show detectable anti-ZIKV serum IgG by day 14 (titers of ~1:1,000) and these levels were boosted with subsequent vaccinations with binding antibody titers reaching at least 1:100,000 (FIG. 33B and FIG. 33C). By comparison, the $PRNT_{50}$ titer for the day 35 postimmunization samples was 1:60. The results indicate that $IFNAR^{-/-}$ mice immunized with the consensus ZIKV-prMEnv vaccine are capable of generating anti-ZIKV cellular and humoral immune responses supporting further study in this model of putative vaccine effects in a pathogenic challenge.

ZIKV-Specific Functional Cellular and Humoral Responses Elicited by the ZIKV-prMEnv DNA Vaccine in Non-Human Primates NHPs were immunized by intradermal immunization using intradermal electroporation, based on recent studies showing potent immune responses in a lower voltage intradermal format (Hutnick et al., 2012, Hum gene Ther 23:943-50; Broderick et al., Mol Ther Nucleic Acids 1:e11). Rhesus macaques (RM; n=5/group) were administered 2.0 mg of vaccine plasmid intradermally with electroporation, with each animal vaccinated twice 4 weeks apart. The sera and peripheral blood mononuclear cells (PBMCs) were collected at day 0 (pre-immunization) and week 6 (2 weeks post second immunization). ELISpot analysis of pre-immunization and week 6 PBMCs ex vivo stimulated with the ZIKV-prMEnv peptide pools showed that ZIKV-prMEnv immunization induced robust anti-ZIKV T cell responses in RM (FIG. 27A).

Specific anti-ZIKV antibody responses in sera from vaccinated RM were assessed by ELISA. At week 6, rZIKV-Env-specific binding antibodies were detectable in animals vaccinated with ZIKV-prMEnv (FIG. 27B). End point titers were determined for each animal at week 2 (after 1 immunization) and week 6 (after 2 immunizations; FIG. 27C). The ELISA results were confirmed by western blot analysis using RM sera from the individual vaccinated animals (FIG. 27D). The neutralization activity of the antibodies generated in RM at week 6 was evaluated by a $PRNT_{50}$ assay. All the vaccinated monkeys had significant neutralization activity with anti-ZIKV reciprocal $PRNT_{50}$ dilution titers ranging from 161 to 1380 (average 501±224 standard error of the mean; FIG. 27E). PRNT titers did not directly correlate with ELISA titer (data not shown).

The ability of the NHP vaccine immune sera to block ZIKV infection of Vero cells, neuroblastoma (SK—N-SH) or neural progenitor (U-87MG) cells in vitro was examined by IFA. ZIKV Q2 strains (MR766 or PR209) were pre-incubated in sera or dilution of NHP-immune sera and added to monolayers of each cell type. Four days post infection, ZIKV-positive cells were identified by IFA using pan flavirus antibody (FIG. 34A-34C) and quantified the ZIKV-positive cells (FIG. 34B-34D). The sera from ZIKA-prME vaccinated RM inhibited the ZIKV infection in each cell type.

Protection Against ZIKV Infection and Disease in $IFNAR^{-/-}$ Mice Following ZIKV-prME Immunization In exploratory studies, 5-6-week-old $IFNAR^{(-/-)}$ mice (n=10) were challenged with $1\times10^6$ plaque-forming units (PFU) of the ZIKV-PR209 isolate, administered by either subcutaneous (s.c.); intraperitoneal (i.p.); intracranial; or intravenous (i.v.) routes. After the challenge, all the animals were monitored for clinical signs of infection, which included routine measurement of body weight as well as inspection for other signs of a moribund condition such as hind limb weakness and paralysis. No change in the general appearance of the mice was observed during the first 4 days after inoculation. However, after the fourth day, the mice in each of the groups demonstrated reduced overall activity, decreased mobility and a hunched posture often accompanied by hind-limb weakness, decreased water intake and obvious weight loss. The animals succumbed to the infection between day 6 and day 8 regardless of the route of viral challenge (FIG. 35A-35E). On the basis of these data, the subsequent studies to evaluate ZIKV-prME-mediated protection in this model used the s.c. route for challenge.

The protective efficacy of the ZIKV-prMEnv vaccine was next evaluated in this IFNAR$^{-/-}$ mice model. Two groups of mice (n=10) were immunized (25 μg of vaccine) by the i.m. route, through electroporation-mediated delivery with the ZIKV-prME vaccine. Also, two groups of 10 mice were immunized by the i.m. route through electroporation-mediated delivery with the control pVax1 vector. The immunizations were performed two times, two weeks apart, and all the animals were challenged on day 21 (1 week post second immunization). One set of control and vaccinated mice received 1×10$^6$ PFU of ZIKV-PR209 by the s.c. route and the other set of each group were challenged with a total of 2×10$^6$ PFU ZIKV-PR209 by the s.c. route. At 3 weeks post challenge, 100% of all ZIKV-prME vaccinated animals survived, whereas only 30% of the single- or 10% of double-dose challenged controls survived (FIG. 28A and FIG. 28B). In all the challenges, the vaccinated animals were without signs of disease including no evidence of weight loss (FIG. 28C and FIG. 28D). The infection of control mice with ZIKV-PR209 virus produced a marked decrease in body weight along with decreased mobility, hunched posture, hindlimb knuckle walking and/or paralysis of one or both hind limbs (FIG. 28E and FIG. 28F).

The potential ability of a single immunization with the ZIKVprME DNA vaccine to protect IFNAR$^{-/-}$ mice from ZIKV challenge was evaluated. Groups of 10 mice were immunized i.m. with electroporation once with either control plasmid or ZIKV-prME vaccine and challenged 2 weeks later with a double total dose of 2×10$^6$ PFU ZIKV-PR209 administration. Three weeks post challenge, 100% of the ZIKV-prME vaccinated animals survived, whereas only 10% of the control animals survived (FIG. 29A). To determine gross histopathological changes, brain tissue was sectioned into 5 μm-thick sagittal sections, stained for nuclear structures and counterstained for cytoplasmic structures using eosin (FIG. 29B). The mice were killed at day 7 or 8 post challenge for the analysis of histology and viral load. The ZIKV infection caused severe brain pathology in the mice. The unvaccinated control (pVax1) mice brain sections showed nuclear fragments within neutrophils (FIG. 29B); perivascular cuffing of vessel within the cortex, lymphocyte infiltration and degenerating cells of the cerebral cortex (FIG. 29B) and degenerating neurons within the hippocampus (FIG. 29B). In contrast, however, the ZIKV prME vaccinated animals presented with normal histopathology in brain tissues (FIG. 29B) supporting that protective antibodies induced by immunization with the synthetic ZIKA-prME vaccine could limit viral-induced disease in the brain. This observation demonstrates the potential for vaccination to protect the brain in this model. Consistent with the amelioration of body weight loss and mobility impairment in vaccinated mice following ZIKV challenge, a significantly lower viral load was noted in the blood (FIG. 29C) and brain (FIG. 29D) of the ZIKV-prME vaccinated animals compared with viral challenged pVax1 vaccinated animals in the high (2×10$^6$ PFU) dose challenge groups. Taken together, these data illustrate that ZIKV-prME DNA vaccine-mediated immune responses can protect mice against ZIKV challenge.

Passive Transfer of Anti-ZIKV Immune Sera Protects Mice Against ZIKV Infection

Figure 30A:
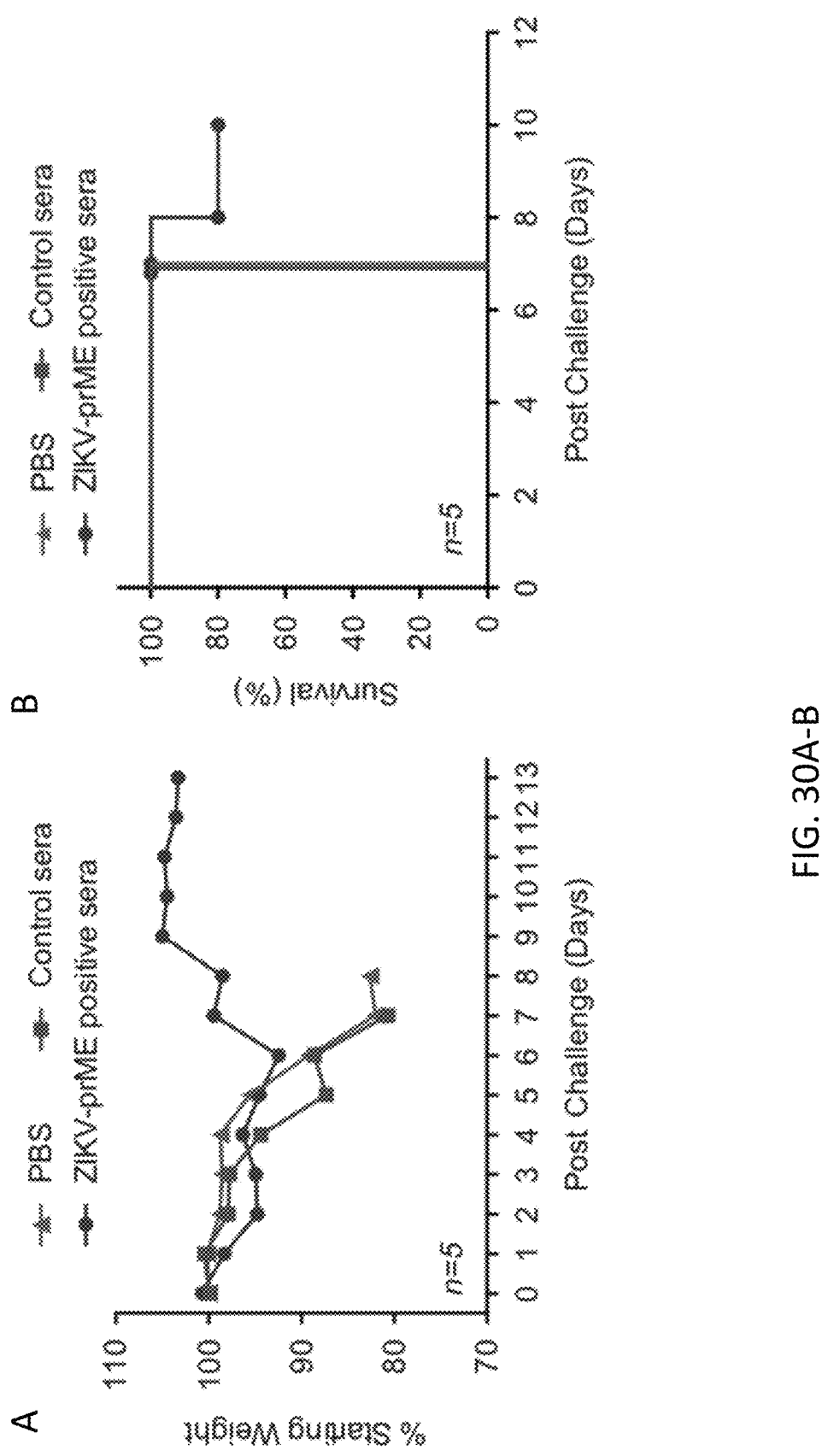

Next, whether transfer of immune sera from ZIKV-prMEnv vaccinated RM would prevent ZIKV-mediated pathogenesis in IFNAR$^{-/-}$ mice was tested. To this end, 150 μg equivalent IgG (PRNT$_{50}$≈1/160) from week 6 RM were adoptively transferred into IFNAR$^{-/-}$ mice 1 day after the ZIKV viral challenge. Two groups of control mice were included, one group receiving pre-immune sera from RM and the other group receiving phosphate-buffered saline (PBS). The mice that received PBS or control sera lost 15 to 25% of their original body weight during the course of infection, and all died 6-8 days post infection. When vaccine immune sera from RMs were transferred to infection-susceptible mice, the animals lost weight on day 3 and 4, but subsequently regained it beginning on day 5 and 80% ultimately survived infectious challenge (FIG. 30A) demonstrating the ability of the NHP sera transfer to confer protection against clinical manifestations of ZIKV infection following viral challenge (FIG. 30B). In repeated experiments performed to evaluate the efficacy of immune serum transfer in protection against challenge with ZIKV, the survival among ZIKV-prME immune sera recipients ranged from 80 to 100%. These studies show that anti-ZIKV vaccine immune sera had the ability to confer significant protection against ZIKV infection in the absence of an acquired adaptive anti-ZIKV immune response.

Vaccination with the ZIKV-prME Consensus Construct

Serious concerns have been raised by the recent spread of ZIKV and its associated pathogenesis in humans. Currently, there are no licensed vaccines or therapeutics for this emerging infectious agent. Very recently, a collection of experimental ZIKV vaccines have been shown to lower viral load post challenge in nonpathogenic animal infection models (Larocca et al., 2016, Nature 536:474-8; Abbink et al., 2016, Science 353:1192-32) These data are encouraging. In this regard, it is important to examine additional novel vaccine approaches targeting ZIKA in additional models. Here a synthetic DNA vaccine, designed to express a novel consensus ZIKV-prM and E antigen, was evaluated for immunogenicity following electroporation-enhanced immunization in mice and non-human primates. It was observed that ZIKV-prME DNA vaccination was immunogenic and generated antigen-specific T cells and binding and neutralizing antibodies in both mice and NHPs. Uniquely, the NHPs were immunized with ZIKV-prME through electroporation by the intradermal route, which uses lower voltage and a smaller transfection area than i.m. electroporation, as has been recently described (Trimble et al., 2016, Lancet 386:2078-88) Further study of such approaches may provide advantages in clinical settings.

The ZIKV-prME consensus construct includes a designed change of the potential NXS/T motif, which removes a putative glycosylation site. Deletion of glycosylation at this site has been correlated with improved binding of EDE1 type bnAbs (broadly neutralizing antibodies) against ZIKV-E protein (Muthumani et al., 2016, Sci Transl Med 7:301ra132). The antibody responses induced by the consensus ZIKV-prME appear as robust or in some cases superior in magnitude to those elicited by similarly developed ZIKV-prME-MR766 and ZIKV-prME-Brazil vaccines. These constructs were sequence matched with the original ZIKV-MR766 isolate or a recently circulating ZIKV strain from Brazil, respectively. While supportive, further study will provide more insight into the effects of such incorporated designed changes on induced immune responses.

As there are few pathogenic challenge models for ZIKV, the putative protective nature of the immune responses of the ZIKV-prME vaccine in C57BL/6 and IFNAR$^{-/-}$ mice was compared. Both the strains of mice responded with a robust humoral immune response when immunized with ZIKV-prME. The T-cell responses were also induced, but appear to be more robust in wild-type C57BL/6 compared with those induced in the IFNAR$^{-/-}$ animals, supporting a partial defect in innate to adaptive immunity transition as expected owing to the knock-out phenotype in the mouse.

However, based on the induction of antigen specific immunity, the model was useful for evaluation of the impact of the vaccine on both infection and pathogenesis. A single vaccination with ZIKV-prME in IFNAR$^{-/-}$ mice was protective against disease and death in this model, including protection of neuro-pathogenesis. Flavivirus-neutralizing antibodies directed against the Env antigen are thought to have a key role in protection against disease, an idea supported directly by passive antibody transfer experiments in animal models and indirectly by epidemiological data from prospective studies in geographical areas that are prone to mosquito-borne viral infections (Weaver et al., 2016, Antiviral Res 130:69-80; Roa et al., 2016, Lancet 387:843; Samarasekera et al., 2016, Lancet 387:521-4). Although immunization of IFNAR$^{-/-}$ mice with the ZIKV-prME DNA vaccine as well as serum transfer from immunized NHPs were protective in this murine model, the IFNAR$^{-/-}$ vaccinated as opposed to serum-transferred mice exhibited improved control of weight loss as an indication of control of pathogenesis. Although additional studies are needed, this result potentially suggests a role for the T-cell response in this aspect of protection in this model. In addition, it was observed that control IFNAR$^{-/-}$ mice who recovered from challenge remain viral positive by PCR for at least several weeks, suggesting an additional benefit of vaccination. This study supports the potential of vaccination and, in this case this synthetic DNA vaccination, to impact prevention of disease in a susceptible host.

Example 4: DNA Vaccine Against Zika Virus prME Induces Protective Immunity in Non-Human Primates Rhesus macaques were immunized intradermal (i.d.) with 2 mg of ZIKV-prME plasmid at weeks 0 and 4 administered as 1 mg at each of two sites, with immunization immediately followed by intradermal electroporation (EP). PBMCs were isolated pre-immunization and at week 6 and were used for the ELISPOT assay to detect IFN-g-secreting cells in response to stimulation with ZIKV-prME peptides (FIG. 36A). NHPs receiving one immunization and NHPs receiving two immunizations showed an increase in IFN-g producing cells obtained per million PBMCs against six peptide pools encompassing the entire prME protein (FIG. 36B and FIG. 36C) which demonstrates an induction of ZIKV specific cellular immune responses following ZIKV-prME vaccination. As shown in FIG. 37, anti-ZIKV antibody responses are induced by ZIKV-prME vaccination of NHPs.

Rhesus macaques were vaccinated twice at weeks 0 and 4 with pZV-prME DNA via ID route using EP. At week 8, the animals were subcutaneous challenged with Zika-PR209 viral strain. As a control, 5-naïve animals were infected with ZV-PR209 virus (FIG. 38A). Naïve NHPs infected with ZV-PR209 each exhibited significant viral loads (FIG. 38B). NHPs which were immunized once or twice with pZV-prME DNA did not have detectable viral loads (FIG. 37C and FIG. 38D). These studies demonstrate that Zika-prME immunization confers protection against Zika challenge.

Example 5: Phase 1 Zika DNA Vaccine Study ID-EP Interim Analysis

ZIKA-001 Clinical Protocol

A first phase I study was an open-label, dose-ranging study to evaluate the safety, tolerability, and immunogenicity of GLS-5700, administered ID followed by EP in dengue virus-naïve adults and was carried out at 3 sites in the US and Canada.

The primary objective of the study was evaluate the safety and tolerability of GLS-5700 when administered by ID injection followed by EP in healthy dengue-virus naïve adult subjects to 14 days from final vaccine administration.

The primary safety endpoints in this study include: (1) Incidence of adverse events classified by system organ class (SOC), preferred term (PT) severity, and relationship to study treatment and schedule to 14 days post-vaccination; (2) Administration (injection) site reactions (described by frequency and severity grade) and administration site pain to 14 days post-final vaccination; and (3) Changes in safety laboratory parameters described by frequency and severity grade (e.g., liver panel tests, vital signs).

The secondary objectives include: (1) Evaluate the safety to 1 year post vaccination of GLS-5700 in dengue-virus naïve adults; and (2) Evaluate cellular and humoral responses of GLS-5700 when delivered ID and followed by EP in dengue-virus naïve adults.

The secondary immunologic endpoints include: (1) Binding antibody titers to the Zika envelope (E) protein as measured by ELISA; (2) Neutralizing antibody titers against Zika virus as measured in viral neutralization assay; and (3) Antigen specific cellular immune responses to Zika virus as determined by Interferon-gamma (IFN-γ) ELISpot and/or Intracellular Staining (ICS) assays.

This Phase I clinical trial evaluates whether GLS-5700 administered via ID injection and followed by electroporation (EP) is safe, tolerated and able to generate an immune response against Zika virus in dengue virus-naïve participants and whether immune reactivity is dose-dependent. Injections will be given in the deltoid muscle followed immediately by EP with the CELLECTRA®-3P device.

GLS-5700 contains plasmid pGX7201 that encodes for a consensus sequence of the pre-membrane (prM) and envelope (E) proteins of Zika virus.

Currently there are no approved treatments or prophylactic vaccines for Zika virus. Nor have any vaccine candidates for Zika virus been advanced into human trials.
Evaluation of ID Administration of GLS-5700:

There are two arms for ZIKA-001 (Table 1). Participants (n=20 per group) will be administered GLS-5700 at one of two dose levels: 1 mg or 2 mg DNA/dose. Vaccine will be administered as 0.1 ml ID injections followed by EP with the CELLECTRA®-3P device. Participants will receive one or two injections into the deltoid region at vaccination at 0, 4, and 12 weeks (3 vaccination series).

TABLE 1

Dosing Arms and Regimens

| Group | Vaccine | Schedule | n | Route | # Injections per dose | Dose (mg) |
|---|---|---|---|---|---|---|
| 1 | GLS-5700 | 0-4-12 weeks | 20 | ID | 1 | 1 |
| 2 | GLS-5700 | 0-4-12 weeks | 20 | ID | 2 | 2 |
| | TOTAL | | 40 | | | |

To assess safety participants are monitored for adverse events utilizing the "Toxicity Grading Scale for Healthy Adult and Adolescent Volunteers Enrolled in Preventive Vaccine Clinical Trials (Appendix B)" with labs assessed as per site normal values. Pain is assessed immediately after EP and at 30 minutes post-EP. Laboratory safety assessments will be obtained at screening, 1 week following the 1$^{st}$ vaccination, and 2 weeks following the 2$^{nd}$ and 3$^{rd}$ vaccinations. Adverse events, including assessment of injection site reactions, are monitored through 12 months after the final vaccination.

The criteria for inclusion in the study population are:
a. Age 18-65 years;
b. Able to provide consent to participate and having signed an Informed Consent Form (ICF);
c. Able and willing to comply with all study procedures;
d. Women of child-bearing potential agree to use medically effective contraception (oral contraception, barrier methods, spermicide, etc.) or have a partner who is sterile from enrollment to 3 months following the last injection, or have a partner who is medically unable to induce pregnancy.
e. Sexually active men who are considered sexually fertile must agree to use either a barrier method of contraception during the study, and agree to continue the use for at least 3 months following the last injection, or have a partner who is permanently sterile or is medically unable to become pregnant;
f. Normal screening ECG or screening ECG with no clinically significant findings;
g. Screening laboratory must be within normal limits or have only Grade 0-1 findings;
h. No history of clinically significant immunosuppressive or autoimmune disease.
i. No history of dengue virus vaccination or illness; no history of yellow fever vaccination.
j. Dengue seronegative at baseline by screening laboratory evaluation
k. Not currently or within the previous 4 weeks taking immunosuppressive agents (excluding inhaled, topical skin and/or eye drop-containing corticosteroids, low-dose methotrexate, or prednisone at a dose less than 10 mg/day or steroid dose-equivalent).

The criteria for exclusion in the study population are:
a. Administration of an investigational compound either currently or within 30 days of first dose;
b. Previous receipt of an investigational product for the treatment or prevention of Zika virus except if participant is verified to have received placebo;
c. Administration of any vaccine within 4 weeks of first dose;
d. Administration of any monoclonal or polyclonal antibody product within 4 weeks of the first dose
e. Administration of any blood product within 3 months of first dose;
f. Pregnancy or breast feeding or plans to become pregnant during the course of the study;
g. Positive serologic result for dengue virus (any serotype) or history of receipt of either dengue virus or yellow fever virus vaccination at any time in the past;
h. Positive serologic test for HIV, hepatitis B surface antigen (HBsAg); or any potentially communicable infectious disease as determined by the Principal Investigator or Medical Monitor;
i. Positive serologic test for hepatitis C (exception: successful treatment with confirmation of sustained virologic response);
j. Baseline evidence of kidney disease as measured by creatinine greater than 1.5 (CKD Stage II or greater);
k. Baseline screening lab(s) with Grade 2 or higher abnormality, except for Grade 2 creatinine;
l. Chronic liver disease or cirrhosis;
m. Immunosuppressive illness including hematologic malignancy, history of solid organ or bone marrow transplantation;
n. Current or anticipated concomitant immunosuppressive therapy (excluding inhaled, topical skin and/or eye drop-containing corticosteroids, low-dose methotrexate, or prednisone at a dose greater than 10 mg/day or steroid dose-equivalent);
o. Current or anticipated treatment with TNF-α inhibitors such as infliximab, adalimumab, etanercept;
p. Prior major surgery or any radiation therapy within 4 weeks of group assignment;
q. Any pre-excitation syndromes, e.g., Wolff-Parkinson-White syndrome;
r. Presence of a cardiac pacemaker or automatic implantable cardioverter defibrillator (AICD)
s. Metal implants within 20 cm of the planned site(s) of injection;
t. Presence of keloid scar formation or hypertrophic scar as a clinically significant medical condition at the planned site(s) of injection.
u. Prisoner or participants who are compulsorily detained (involuntary incarceration) for treatment of either a physical or psychiatric illness;
v. Active drug or alcohol use or dependence that, in the opinion of the investigator, would interfere with adherence to study requirements or assessment of immunologic endpoints; or
w. Not willing to allow storage and future use of samples for Zika virus related research
x. Any illness or condition that in the opinion of the investigator may affect the safety of the participant or the evaluation of any study endpoint.

ZIKA-002 Clinical Protocol

A second phase I study was a placebo-controlled, double blind study to evaluate the safety, tolerability, and immunogenicity of GLS-5700, administered ID and followed by electroporation in a dengue-seropositive adults in Puerto Rico. The primary objective of the study was to evaluate the safety and tolerability of GLS-5700 when administered by ID injection followed by EP in dengue seropositive healthy adult subjects to 12 weeks from final vaccine administration.

The primary safety endpoints in this study include: (1) Incidence of adverse events classified by system organ class (SOC), preferred term (PT) severity, and relationship to study treatment and schedule to 12 weeks post-final vaccination; (2) Administration (injection) site reactions (described by frequency and severity grade) and administration site pain to 12 weeks post-final vaccination; and (3) Changes in safety laboratory parameters described by frequency and severity grade (e.g., liver panel tests, vital signs). The secondary safety endpoints in this study include: (1) Evaluate the safety of GLS-5700 through 1 year post-final vaccination in dengue-virus seropositive adults; and (2) Evaluate cellular and humoral responses of GLS-5700 delivered ID and followed by EP in dengue virus-seropositive adults.

The secondary immunologic endpoints include: (1) Binding antibody titers to the Zika envelope (E) measured by ELISA; (2) Neutralizing antibodies against Zika virus as measured in neutralization assay; and (3) Antigen specific cellular immune responses to Zika virus as determined by Interferon-gamma (IFN-γ) ELISpot and/or Intracellular Staining (ICS) assays.

This Phase I clinical trial evaluates whether GLS-5700 administered via ID injection and followed by electroporation (EP) is safe, tolerated, and able to generate an immune response against Zika virus in dengue seropositive adults.

Injections are given intradermally in the deltoid region followed immediately by EP with the CELLECTRA®-3P device.

GLS-5700 contains plasmid pGX7201 that encodes for a consensus sequence of the pre-membrane (prM) and envelope (E) proteins of Zika virus.

Currently there are no approved treatments or prophylactic vaccines for Zika virus. Nor have vaccine candidates for Zika virus advanced into human trials.

Evaluation of ID Administration of GLS-5700:

Subjects (n=80 per group) will be randomized to be administered either GLS-5700 (GLS-5700 is formulated in SSC) at 2 mg DNA/dose or placebo (SSC, compositional buffer for GLS-5700). Vaccine or placebo will be administered as two 0.1 mL ID injections followed by EP with the CELLECTRA®-3P device. Subjects will receive vaccinations into the deltoid region at 0, 4, and 12 weeks (3 vaccination series; Table 2).

TABLE 2

Dosing Arms and Regimens

| Group | Vaccine | Schedule | n | Route | Dose (mg) |
|---|---|---|---|---|---|
| 1 | Placebo | 0-4-12 weeks | 80 | ID | 0 |
| 2 | GLS-5700 | 0-4-12 weeks | 80 | ID | 2 |
| | TOTAL | | 160 | | |

To assess safety subjects are monitored for adverse events utilizing the "Toxicity Grading Scale for Healthy Adult and Adolescent Volunteers Enrolled in Preventive Vaccine Clinical Trials (Appendix B)" with labs assessed as per site normal values. Pain is assessed at 30 minutes post-EP. Laboratory safety assessments will be obtained at screening, 1 week following the $1^{st}$ vaccination, and 2 weeks following the $2^{nd}$ and $3^{rd}$ vaccinations as applicable. Adverse events, including assessment of injection site reactions, will be monitored through 12 months after the final vaccination.

The criteria for inclusion in the study population are:
a. Age 18-65 years;
b. Able to provide consent to participate and having signed an Informed Consent Form (ICF);
c. Able and willing to comply with all study procedures;
d. Women of child-bearing potential agree to use medically effective contraception (oral contraception, barrier methods, spermicide, etc.) or have a partner who is sterile from enrollment to 3 months following the last injection, or have a partner who is medically unable to induce pregnancy.
e. Sexually active men who are considered sexually fertile must agree to use either a barrier method of contraception during the study, and agree to continue the use for at least 3 months following the last injection, or have a partner who is permanently sterile or is medically unable to become pregnant;
f Dengue virus seropositive at screening;
g. Normal screening ECG or screening ECG with no clinically significant findings;
h. Screening laboratory must be within normal limits or have only Grade 0-1 findings;
i. No history of clinically significant immunosuppressive or autoimmune disease.
j. No history of dengue virus vaccination; no history of yellow fever vaccination.
k. Not currently or within the previous 4 weeks taking immunosuppressive agents (excluding inhaled, topical skin and/or eye drop-containing corticosteroids, low-dose methotrexate, or prednisone at a dose less than 10 mg/day, or a steroid equivalent).

The criteria for exclusion in the study population are:
a. Administration of an investigational compound either currently or within 30 days of first dose;
b. Previous receipt of an investigational product for the treatment or prevention of Zika virus except if subject is verified to have received placebo;
c. Administration of any vaccine within 4 weeks of first dose;
d. Administration of any monoclonal or polyclonal antibody product within 4 weeks of the first dose
e. Administration of any blood product within 3 months of first dose;
f Pregnancy or breast feeding or plans to become pregnant during the course of the study;
g. Negative serologic result for dengue virus
h. History of receipt of either dengue virus or yellow fever virus vaccination at any time in the past;
i. History of positive serologic test for HIV, hepatitis B surface antigen (HBsAg); or any potentially communicable infectious disease as determined by the Principal Investigator or Medical Monitor;
j. Positive serologic test for hepatitis C (exception: successful treatment with confirmation of sustained virologic response);
k. Baseline evidence of kidney disease as measured by creatinine greater than 1.5 (CKD Stage II or greater);
l. Baseline screening lab(s) with Grade 2 or higher abnormality, except for Grade 2 creatinine;
m. Chronic liver disease or cirrhosis;
n. Immunosuppressive illness including hematologic malignancy, history of solid organ or bone marrow transplantation;
o. Current or anticipated concomitant immunosuppressive therapy (excluding inhaled, topical skin and/or eye drop-containing corticosteroids, low-dose methotrexate, or prednisone at a dose equal to or greater than 10 mg/day, or steroid equivalent);
p. Current or anticipated treatment with TNF-α inhibitors such as infliximab, adalimumab, etanercept;
q. Prior major surgery or any radiation therapy within 4 weeks of group assignment;
r. Any pre-excitation syndromes, e.g., Wolff-Parkinson-White syndrome;
s. Presence of a cardiac pacemaker or automatic implantable cardioverter defibrillator (AICD)
t. Metal implants within 20 cm of the planned site(s) of injection;
u. Presence of keloid scar formation or hypertrophic scar as a clinically significant medical condition at the planned site(s) of injection.
v. Prisoner or subjects who are compulsorily detained (involuntary incarceration) for treatment of either a physical or psychiatric illness;
w. Active drug or alcohol use or dependence that, in the opinion of the investigator, would interfere with adherence to study requirements or assessment of immunologic endpoints; or
x. Not willing to allow storage and future use of samples for Zika virus related research
y. Any illness or condition that in the opinion of the investigator may affect the safety of the subject or the evaluation of any study endpoint.

Clinical Results

Patients were immunized at Day 0 and week 4 with pZV-prME DNA (FIG. 39-42). To determine the percentage of binding responders, sera were incubated at indicated dilution in plates coated with Zika Env protein and a secondary antibody detected total IgG responses.

Vero cells infected with Zika virus, 3 days later cells are fixed, then incubated with 1:100 dilution of sera from Day 0 and Wk 6.

Neutralizing studies were carried out by determining the $IC_{50}$ of patient sera (dilution of sera that neutralizes ZIKV PR209 infection of Vero cells by 50%).

FIG. 39A provides the results of a binding ELISA assay. FIG. 39B provides experimental results demonstrating passive transfer and protection.

FIG. 40 provides exemplary immunofluorescence data showing an increase in Anti-human IgG-AF488 staining post dose 2.

FIG. 41 provides data demonstrating the characterization of the binding responders.

Figure 42:
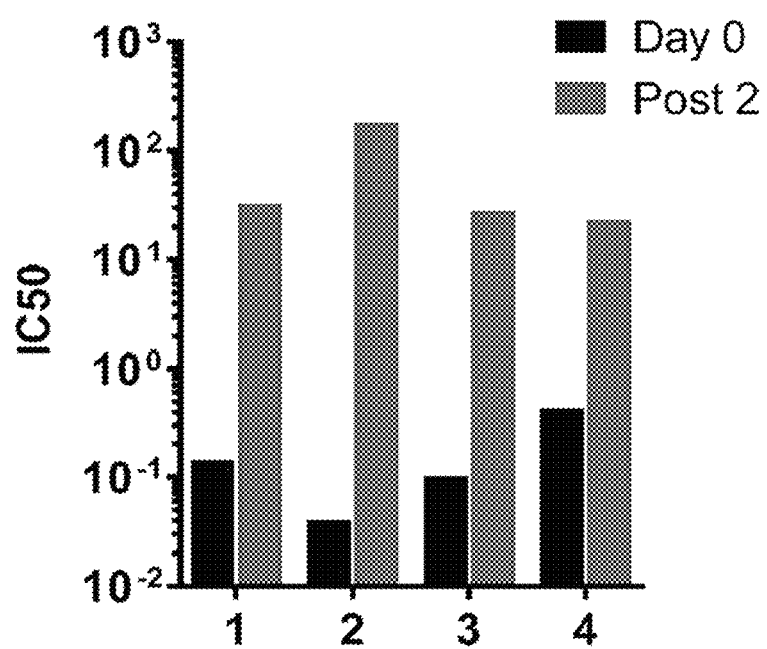
FIG. 42 depicts experimental results demonstrating neutralization post dose 2.

FIG. 42 provides data demonstrating that there was an increase in neutralization post dose 2.

We claim:

1. A synthetic consensus Zika antigen, wherein the amino acid of the synthetic consensus Zika antigen is selected from the group consisting of:

SEQ ID NO:1, an amino acid sequence that is at least 97% homologous to SEQ ID NO:1, a fragment of SEQ ID NO:1 lacking an IgE signal peptide, an amino acid sequence that is at least 97% homologous to a fragment of SEQ ID NO:1 lacking an IgE signal peptide, SEQ ID NO:3, an amino acid sequence that is at least 98% homologous to SEQ ID NO:3, a fragment of SEQ ID NO:3 lacking an IgE signal peptide, an amino acid sequence that is at least 98% homologous to a fragment of SEQ ID NO:3 lacking an IgE signal peptide, SEQ ID NO:5, an amino acid sequence that is at least 95% homologous to SEQ ID NO:5, a fragment of SEQ ID NO:5 lacking an IgE signal peptide, an amino acid sequence that is at least 95% homologous to a fragment of SEQ ID NO:5 lacking an IgE signal peptide, SEQ ID NO:7, an amino acid sequence that is at least 90% homologous to SEQ ID NO:7, a fragment of SEQ ID NO:7 lacking an IgE signal peptide, and an amino acid sequence that is at least 90% homologous to a fragment of SEQ ID NO:7 lacking an IgE signal peptide.

2. A method of inducing an immune response against a Zika virus comprising administering the antigen of claim 1 to an individual in an amount effective to induce an immune response in said individual.

3. A method of treating an individual who has been diagnosed with Zika virus comprising administering a therapeutically effective amount of the antigen of claim 1 to an individual.

4. A pharmaceutical composition comprising a plasmid, wherein the plasmid comprises a nucleic acid molecule encoding a consensus Zika antigen selected from the group consisting of:

SEQ ID NO:1, an amino acid sequence that is at least 97% homologous to SEQ ID NO:1, a fragment of SEQ ID NO:1 lacking an IgE signal peptide, an amino acid sequence that is at least 97% homologous to a fragment of SEQ ID NO:1 lacking an IgE signal peptide, SEQ ID NO:3, an amino acid sequence that is at least 98% homologous to SEQ ID NO:3, a fragment of SEQ ID NO:3 lacking an IgE signal peptide, an amino acid sequence that is at least 98% homologous to a fragment of SEQ ID NO:3 lacking an IgE signal peptide, SEQ ID NO:5, an amino acid sequence that is at least 95% homologous to SEQ ID NO:5, a fragment of SEQ ID NO:5 lacking an IgE signal peptide, an amino acid sequence that is at least 95% homologous to a fragment of SEQ ID NO:5 lacking an IgE signal peptide, SEQ ID NO:7, an amino acid sequence that is at least 90% homologous to SEQ ID NO:7, a fragment of SEQ ID NO:7 lacking an IgE signal peptide, and an amino acid sequence that is at least 90% homologous to a fragment of SEQ ID NO:7 lacking an IgE signal peptide, wherein the composition is formulated for administration of the nucleic acid molecule at a dosage selected from the group consisting of 1 mg of plasmid and 2 mg of plasmid.

5. The composition of claim 4, wherein the amino acid of the consensus Zika antigen is selected from the group consisting of: SEQ ID NO:1, an amino acid sequence that is at least 97% homologous to SEQ ID NO:1, a fragment of SEQ ID NO: 1 lacking an IgE signal peptide, and an amino acid sequence that is at least 97% homologous to a fragment of SEQ ID NO:1 lacking an IgE signal peptide.

6. The composition of claim 4, wherein the amino acid of the consensus Zika antigen selected from the group consisting of: SEQ ID NO:3, an amino acid sequence that is at least 98% homologous to SEQ ID NO:3, a fragment of SEQ ID NO:3 lacking an IgE signal peptide, and an amino acid sequence that is at least 98% homologous to a fragment of SEQ ID NO:3 lacking an IgE signal peptide.

7. The composition of claim 4, wherein the amino acid of the consensus Zika antigen selected from the group consisting of: SEQ ID NO:5, an amino acid sequence that is at least 95% homologous to SEQ ID NO:5, a fragment of SEQ ID NO:5 lacking an IgE signal peptide, and an amino acid sequence that is at least 95% homologous to a fragment of SEQ ID NO:5 lacking an IgE signal peptide.

8. The composition of claim 4, wherein the amino acid of the consensus Zika antigen selected from the group consisting of: SEQ ID NO:7, an amino acid sequence that is at least 90% homologous to SEQ ID NO:7, a fragment of SEQ ID NO:7 lacking an IgE signal peptide, and an amino acid sequence that is at least 90% homologous to a fragment of SEQ ID NO:7 lacking an IgE signal peptide.

9. The composition of claim 4 formulated for delivery to an individual using electroporation.

10. The composition of claim 4 further comprising nucleic acid sequences that encode one or more proteins selected from the group consisting of: IL-12, IL-15 and IL-28.

11. A method of inducing an immune response against a Zika virus comprising administering the composition of claim 4 to an individual in an amount effective to induce an immune response in said individual.

12. A method of treating an individual who has been diagnosed with Zika virus comprising administering a therapeutically effective amount of the composition of claim 4 to an individual.

13. A synthetic nucleic acid molecule encoding one or more Zika virus antigen, wherein the synthetic nucleic acid molecule comprises a sequence selected from the group consisting of:

a nucleotide sequence encoding SEQ ID NO:9, a nucleotide sequence encoding an amino acid sequence that is at least 98% homologous to SEQ ID NO:9, a nucleotide sequence encoding a fragment of SEQ ID NO: 9 lacking an IgE signal peptide, an amino acid sequence that is at least 98% homologous to a fragment of SEQ ID NO:9 lacking an IgE signal peptide, a nucleotide sequence encoding SEQ ID NO: 11, a nucleotide sequence encoding an amino acid sequence that is at least 98% homologous to SEQ ID NO: 11, a nucleotide sequence encoding a fragment of SEQ ID NO:11 lacking an IgE signal peptide, an amino acid sequence that is at least 98% homologous to a fragment of SEQ ID NO:11 lacking an IgE signal peptide, a nucleotide sequence encoding SEQ ID NO:18, a nucleotide sequence encoding an amino acid sequence that is at least 99% homologous to SEQ ID NO:18, a nucleotide sequence encoding a fragment of SEQ ID NO:18 lacking an IgE signal peptide, an amino acid sequence that is at least 99% homologous to a fragment of SEQ ID NO:18 lacking an IgE signal peptide, a nucleotide sequence encoding SEQ ID NO: 19, a nucleotide sequence encoding an amino acid sequence that is at least 90% homologous to SEQ ID NO:19, a nucleotide sequence encoding a fragment of SEQ ID NO:19 lacking an IgE signal peptide, and an amino acid sequence that is at least 90% homologous to a fragment of SEQ ID NO:19 lacking an IgE signal peptide.

14. The synthetic nucleic acid molecule of claim 13, wherein the nucleic acid molecule comprises a nucleotide sequence selected from the group consisting of SEQ ID NO:8, a sequence that is at least 90% identical to SEQ ID NO:8, a fragment of SEQ ID NO:8 lacking the nucleotide sequence encoding the IgE leader sequence, a nucleotide sequence at least 90% identical to a fragment of SEQ ID NO:8 lacking the nucleotide sequence encoding the IgE signal peptide, SEQ ID NO:16, a sequence that is at least 90% identical to SEQ ID NO:16, a fragment of SEQ ID NO:16 lacking the nucleotide sequence encoding the IgE leader sequence, and a nucleotide sequence at least 90% identical to a fragment of SEQ ID NO: 16 lacking the nucleotide sequence encoding the IgE signal peptide.

15. The synthetic nucleic acid molecule of claim 13, wherein the nucleic acid molecule comprises a nucleotide sequence selected from the group consisting of SEQ ID NO:10, a sequence that is at least 90% identical to SEQ ID NO:10, a fragment of SEQ ID NO:10 lacking the nucleotide sequence encoding the IgE leader sequence, and a nucleotide sequence at least 90% identical to a fragment of SEQ ID NO:10 lacking the nucleotide sequence encoding the IgE signal peptide, SEQ ID NO:15, a sequence that is at least 90% identical to SEQ ID NO:15, a fragment of SEQ ID NO:15 lacking the nucleotide sequence encoding the IgE leader sequence, and a nucleotide sequence at least 90% identical to a fragment of SEQ ID NO:15 lacking the nucleotide sequence encoding the IgE signal peptide.

16. The synthetic nucleic acid molecule of claim 13, wherein the nucleic acid molecule comprises a nucleotide sequence selected from the group consisting of SEQ ID NO:17, a sequence that is at least 90% identical to SEQ ID NO:17, a fragment of SEQ ID NO:17 lacking the nucleotide sequence encoding the IgE leader sequence, and a nucleotide sequence at least 90% identical to a fragment of SEQ ID NO:17 lacking the nucleotide sequence encoding the IgE signal peptide.

17. The composition of claim 4, wherein the nucleic acid molecule encoding a consensus Zika antigen comprises a nucleotide sequence selected from the group consisting of SEQ ID NO:13, a sequence that is at least 90% identical to SEQ ID NO:13,a fragment of SEQ ID NO:13 lacking the nucleotide sequence encoding the IgE leader sequence, a nucleotide sequence at least 90% identical to a fragment of SEQ ID NO:13lacking the nucleotide sequence encoding the IgE signal peptide, SEQ ID NO:14, a sequence that is at least 90% identical to SEQ ID NO:14, a fragment of SEQ ID NO:14 lacking the nucleotide sequence encoding the IgE leader sequence, a nucleotide sequence at least 90% identical to a fragment of SEQ ID NO:14 lacking the nucleotide sequence encoding the IgE signal peptide.

* * * * *